(12) United States Patent
Blaschuk et al.

(10) Patent No.: US 7,481,999 B2
(45) Date of Patent: Jan. 27, 2009

(54) COMPOUNDS AND METHODS FOR MODULATING OB-CADHERIN-MEDIATED FUNCTION

(75) Inventors: Orest W. Blaschuk, Westmont (CA); Barbara J. Gour, Kemptville (CA); James Matthew Symonds, Durham, NC (US); Stephen Byers, Washington, DC (US)

(73) Assignee: Adherex Technologies, Inc., Ottawa (CA)

( * ) Notice: Subject to any disclaimer, the term of this patent is extended or adjusted under 35 U.S.C. 154(b) by 177 days.

(21) Appl. No.: 11/003,150

(22) Filed: Dec. 3, 2004

(65) Prior Publication Data
US 2005/0215482 A1   Sep. 29, 2005

Related U.S. Application Data

(60) Continuation-in-part of application No. 10/759,379, filed on Jan. 16, 2004, now abandoned, which is a continuation of application No. 09/305,928, filed on May 5, 1999, now Pat. No. 6,682,901, which is a continuation-in-part of application No. 09/234,395, filed on Jan. 20, 1999, now Pat. No. 6,680,175, which is a continuation-in-part of application No. 09/187,859, filed on Nov. 6, 1998, now Pat. No. 6,358,920, which is a continuation-in-part of application No. 09/073,040, filed on May 5, 1998, now Pat. No. 6,472,367, application No. 11/003,150, which is a continuation-in-part of application No. 10/759,507, filed on Jan. 16, 2004, now abandoned, which is a continuation of application No. 09/234,395, filed on Jan. 20, 1999, now Pat. No. 6,680,175, which is a continuation-in-part of application No. 09/187,859, filed on Nov. 6, 1998, now Pat. No. 6,358,920, which is a continuation-in-part of application No. 09/073,040, filed on May 5, 1998, now Pat. No. 6,472,367, application No. 11/003,150, which is a continuation-in-part of application No. 10/654,578, filed on Sep. 3, 2003, now abandoned, which is a continuation of application No. 09/535,852, filed on Mar. 27, 2000, now Pat. No. 6,638,911, which is a continuation-in-part of application No. 09/187,859, filed on Nov. 6, 1998, now Pat. No. 6,358,920, which is a continuation-in-part of application No. 09/073,040, filed on May 5, 1998, now Pat. No. 6,472,367, application No. 11/003,150, which is a continuation-in-part of application No. 10/395,032, filed on Mar. 21, 2003, now abandoned, which is a continuation of application No. 09/839,542, filed on Apr. 20, 2001, now Pat. No. 6,569,996, which is a division of application No. 09/187,859, filed on Nov. 6, 1998, now Pat. No. 6,358,920, which is a continuation-in-part of application No. 09/073,040, filed on May 5, 1998, now Pat. No. 6,472,367, application No. 11/003,150, which is a continuation-in-part of application No. 10/141,357, filed on May 7, 2002, now abandoned, which is a continuation of application No. 09/305,927, filed on May 5, 1999, now Pat. No. 6,433,149, which is a continuation-in-part of application No. 09/264,516, filed on Mar. 8, 1999, now Pat. No. 6,593,297, which is a continuation-in-part of application No. 09/234,395, filed on Jan. 20, 1999, now Pat. No. 6,680,175, which is a continuation-in-part of application No. 09/187,859, filed on Nov. 6, 1998, now Pat. No. 6,358,920, which is a continuation-in-part of application No. 09/073,040, filed on May 5, 1998, now Pat. No. 6,472,367, application No. 11/003,150, which is a continuation-in-part of application No. 10/006,869, filed on Dec. 3, 2001, now Pat. No. 6,962,969, which is a continuation of application No. 09/187,859, filed on Nov. 6, 1998, now Pat. No. 6,358,920, which is a continuation-in-part of application No. 09/073,040, filed on May 5, 1998, now Pat. No. 6,472,367.

(51) Int. Cl.
*A61K 39/395* (2006.01)
*C07K 16/18* (2006.01)

(52) U.S. Cl. .............. 424/130.1; 424/139.1; 530/387.1; 530/387.9; 530/388.1

(58) Field of Classification Search ...................... None
See application file for complete search history.

(56) References Cited

U.S. PATENT DOCUMENTS 5,585,351 A   12/1996   Ranscht ....................... 514/12

(Continued)

FOREIGN PATENT DOCUMENTS

EP   1074618   2/2001

(Continued)

OTHER PUBLICATIONS

Feltes et al., Cancer Research, 63:6688-6697, Nov. 15, 2002.*

(Continued)

*Primary Examiner*—Marianne P Allen
(74) *Attorney, Agent, or Firm*—Seed IP Law Group PLLC

(57) ABSTRACT

Compositions and methods for modulating OB-cadherin-mediated functions are provided. The compositions and methods employ OB-cadherin modulating agents which generally comprise one or more of: (a) a peptide sequence that is at least 50% identical to an OB-cadherin CAR sequence; (b) a non-peptide mimetic of an OB-cadherin CAR sequence; (c) a substance, such as an antibody or antigen-binding fragment thereof, that specifically binds an OB-cadherin CAR sequence; and/or (d) a polynucleotide encoding a polypeptide that comprises an OB-cadherin CAR sequence or analogue thereof.

3 Claims, 12 Drawing Sheets

U.S. PATENT DOCUMENTS

| | | | | |
|---|---|---|---|---|
| 5,597,725 | A | 1/1997 | Suzuki | 435/328 |
| 5,610,281 | A | 3/1997 | Brenner et al. | 530/388.85 |
| 5,639,634 | A | 6/1997 | Suzuki | 435/69.1 |
| 5,643,781 | A | 7/1997 | Suzuki | 435/325 |
| 5,646,250 | A | 7/1997 | Suzuki | 530/350 |
| 5,663,300 | A | 9/1997 | Suzuki | 530/350 |
| 5,708,143 | A | 1/1998 | Suzuki | 530/350 |
| 5,811,514 | A | 9/1998 | Bard et al. | 530/324 |
| 5,869,638 | A | 2/1999 | Takeshita et al. | 536/23.5 |
| 5,895,748 | A | 4/1999 | Johnson et al. | 435/7.23 |
| 5,916,771 | A | 6/1999 | Hori et al. | 435/69.6 |
| 5,997,866 | A | 12/1999 | Johnson et al. | 434/138.1 |
| 6,031,072 | A | 2/2000 | Blaschuk et al. | 430/317 |
| 6,060,595 | A | 5/2000 | Scaglioni et al. | 536/23.72 |
| 6,083,713 | A | 7/2000 | Manly et al. | 435/69.1 |
| 6,169,071 | B1 | 1/2001 | Blaschuk et al. | 514/4 |
| 6,358,920 | B1 | 3/2002 | Blaschuk et al. | 514/9 |
| 6,417,325 | B1 | 7/2002 | Blaschuk et al. | 530/317 |
| 6,472,367 | B1 | 10/2002 | Blaschuk et al. | 514/9 |
| 6,638,911 | B1 | 10/2003 | Blaschuk et al. | 514/15 |

FOREIGN PATENT DOCUMENTS

| | | |
|---|---|---|
| GB | 2 282 379 A | 4/1995 |
| WO | WO 91/04745 | 4/1991 |
| WO | WO 94/11401 | 5/1994 |
| WO | WO 96/27387 | 9/1996 |
| WO | WO 97/10258 | 3/1997 |
| WO | WO 97/18236 | 5/1997 |
| WO | WO 97/38011 | 10/1997 |
| WO | WO 97/41149 | 11/1997 |
| WO | WO 98/02452 | 1/1998 |
| WO | WO 98/25946 | 6/1998 |
| WO | WO 99/16791 | 4/1999 |
| WO | WO 99/33875 | 7/1999 |
| WO | WO 00/02917 | 1/2000 |
| WO | WO 01/049713 | 7/2001 |
| WO | WO 01/072829 | 10/2001 |
| WO | WO 01/72956 | 10/2001 |
| WO | WO 01/75109 | 10/2001 |

OTHER PUBLICATIONS

Albelda et al., "Adhesion molecules and inflammatory injury," *The FASEB Journal* 8(8):504-512, 1994.

Bangma et al., "The Value of Screening Tests in the Detection of Prostate Cancer. Part I: Results of a Retrospective Evaluation of 1726 Men," *Urology* 46(6): 773-778, 1995.

Berndorff et al., "Liver-Intestine Cadherin: Molecular Cloning and Characterization of a Novel $Ca^{2+}$ -dependent Cell Adhesion Molecule Expressed in Liver and Intestine," *The Journal of Cell Biology* 125(6): 1353-1369, 1994.

Blaschuk and Farookhi, "Estradiol Stimulates Cadherin Expression in Rat Granulosa Cells," *Developmental Biology* 136: 564-567, 1989.

Blaschuk et al., "E-cadherin, estrogens and cancer: is there a connection?," *The Canadian Journal of Oncology* 4(4): 291-301, Nov. 1994.

Breier et al., "Molecular Cloning and Expression of Murine Vascular Endothelial-Cadherin in Early Stage Development of Cardiovascular System," *Blood* 87(2): 630-641, Jan. 15, 1996.

Bussemakers et al., "The role of OB-cadherin in human prostate cancer," *Proceedings of the American Association for Cancer Research* vol. 39, No. 3405, New Orleans, LA, Mar. 28-Apr. 1, 1998.

Caveda, L. et al., "Inhibition of Cultured Cell Growth by Vascular Endothelial Cadherin (Cadherin-5/VE-Cadherin)," *Journal of Clinical Investigation* 98(4): 886-893, Aug. 1996.

Doherty and Walsh, "CAM-FGF Receptor Interactions: A Model for Axonal Growth," *Molecular and Cellular Neuroscience* 8: 99-111, 1996.

Doherty and Walsh, "Signal tranduction events underlying neurite outgrowth stimulated by cell adhesion molecules," *Current Opinion in Neurobiology* 4: 49-55, 1994.

Edgington, "How Sweet It Is: Selectin-Mediating Drugs," *Bio/Technology* 10(4): 383-389. Apr. 1992.

Fredette and Ranscht, "T-Cadherin Expression Delineates Specific Regions of the Developing Motor Axon-Hindlimb Projection Pathway,"*The Journal of Neuroscience* 14(12): 7331-7346, Dec. 1994.

Genbank Accession No. AB008178, Feb. 13, 1999.
Genbank Accession No. AB008180, Feb 13, 1999.
Genbank Accession No. AB008181, Feb. 13, 1999.
Genbank Accession No. AB008182, Feb. 13, 1999.
Genbank Accession No. AB008183, Feb. 13, 1999.
Genbank Accession No. AF029343, Nov. 10, 1997.
Genbank Accession No. D17427, Feb. 1, 2000.
Genbank Accession No. D31784, Jul. 7, 1997.
Genbank Accession No. D42150, Feb. 9, 1999.
Genbank Accession No. D83348, Feb. 6, 1999.
Genbank Accession No. D83542, Oct. 28, 2000.
Genbank Accession No. D86916, Feb. 7, 1999.
Genbank Accession No. D86917, Feb. 7, 1999.
Genbank Accession No. D88349, Feb. 7, 1999.
Genbank Accession No. L11373, Sep. 14, 1995.
Genbank Accession No. L34056, Jun. 29, 1994.
Genbank Accession No. L34057, Jun. 29, 1994.
Genbank Accession No. L34058, Jun. 29, 1994.
Genbank Accession No. L34060, Jun. 29, 1994.
Genbank Accession No. U59325, Jun. 27, 1996.
Genbank Accession No. X56654, Aug. 3, 1993.
Genbank Accession No. X56807, Apr. 5, 1995.
Genbank Accession No. X59796, Jan. 24, 1995.
Genbank Accession No. X72925, Feb. 24, 1999.
Genbank Accession No. X83228, Jun. 1, 1995.
Genbank Accession No. X83929, Dec. 14, 1995.
Genbank Accession No. Z26317, May 15, 2001.

Getsios et al., "Regulated Expression of Cadherin-6 and Cadherin-11 in the Glandular Epithelial and Stromal Cells of the Human Endometrium," *Developmental Dynamics* 211: 238-247, 1998.

Griffiths et al., "Cell adhesion molecules in bladder cancer: soluble serum E-cadherin correlates with predictors of recurrence," *Br. J. Cancer* 74:579-584, 1996.

Grillner and Matsushima, "The Neural Network Underlying Locomotion Lamprey—Synaptic and Cellular Mechanisms,"*Neuron* 7: Jul. 1-15, 1991.

Hall et al., "Review: A Role for the FGF Receptor in the Axonal Growth Response Stimulated by Cell Adhesion Molecules?," *Cell Adhesion and Communication* 3: 441-450, 1996.

Hanahan, D., "Signaling Vascular Morphogenesis and Maintenance," *Science* 277: 48-50, Jul. 4, 1997.

Hazan, R.B. et al., "N-Cadherin Promotes Adhesion Between Invasive Breast Cancer Cells and the Stroma," *Cell Adhesion and Communication* 4(6): 399-411, 1997.

Huber, P. et al., "Genomic Structure and Chromosomal Mapping of the Mouse VE-Cadherin Gene (*Cdh5*)," *Genomics* 32: 21-28, 1996.

Inoue et al., "Cadherin-6 in the Developing Mouse Brain: Expression Along Restricted Connection Systems and Synaptic Localization Suggest a Potential Role in Neuronal Circuitry," *Developmental Dynamics* 211: 338-351, Apr. 1998.

Iruela-Aripse et al., "Expression of SPARC during Development of the Chicken Chorioallantoic Membrane: Evidence for Regulated Proteolysis In Vivo," *Molecular Biology of the Cell* 6: 327-343, Mar. 1995.

Kahan, "Immunosuppressive Therapy," *Current Opinion in Immunology* 4(5): 553-560, Oct. 1992.

Katayama et al., "Soluble E-cadherin fragments increased in circulation of cancer patients," *Br. J. Cancer* 69: 580-585, 1994.

Kawamura et al., "cDNA Cloning and Expression of a Novel Human Desmocollin," *The Journal Of Biological Chemistry* 269(42): 26295-26302, Oct. 21, 1994.

Kido et al., "Molecular Properties and Chromosomal Location of Cadherin-8," *Genomics* 48: 186-194, 1998.

Kimura, Y. et al., "Cadherin-11 Expressed in Association with Mesenchymal Morphogenesis in the Head, Somite, and Limb Bud of Early Mouse Embryos," *Developmental Biology 169*: 347-358, 1995.

King et al., "Cloning of the cDNA (DSCI) Coding for Human Type 1 Desmocollin and Its Assignment to Chromosome 18," *Genomics 18*: 185-194, 1993.

King et al., "The Desmocollins of Human Foreskin Epidermis: Identification and Chromosomal Assignment of a Third Gene and Expression Patterns of the Three Isoforms," *J Invest Dermatol 105*: 314-321, 1995.

Klopfenstein et al., "Increased N-cadherin mediated adhesion does not reduce invasion of Rous sarcoma virus-transformed astrocycle-like WC5 cells," *Proceedings of the American Association for Cancer Research 34*: 33, #195, Mar. 1993.

Knudsen et al., "Interaction of alpha-actinin with the cadherin/catenin cell-cell adhesion complex via alpha-catenin," *J. Cell Biol.* 130(1):67-77, Jul. 1995.

Koch et al., "Complete amino acid sequence of the epidermal desmoglein precursor polypeptide and identification of a second type of desmoglein gene," *European Journal of Cell Biology 55*: 200-208, 1991.

Kogan et al., "A Single Amino Acid Residue Can Determine the Ligand Specificity of E-selectin," *The Journal of Biological Chemistry 270*(23):14047-14055, Jun. 9, 1995.

Kohmura et al., "Diversity Revealed by a Novel Family of Cadherins Expressed in Neurons at a Synaptic Complex," *Neuron 20*: 1137-1151, Jun. 1998.

Kools, P.F.J. et al., "Expression in mesenchymal tumors of alternative cadherin-11 transcripts encoding truncated adhesion molecules: a mechanism for acquiring invasive properties?" *Clinical & Experimental Metastasis 14*(Suppl.1): 52-53, Sep. 1996.

Kreft et al., "L1-Cadherin-mediated Cell-Cell Adhesion Does Not Require Cytoplasmic Interactions," *The Journal of Cell Biology 136*(5): 1109-1121, Mar. 10, 1997.

Lindahl et al., "Pericyte Loss and Microaneurysm Formation in PDGF-B—Deficient Mice," *Science 277*: 242-245. Jul. 11,1997.

Loric et al., "Enhanced Detection of Hematogenous Circulating Prostatic Cells in Patients with Prostate Adenocarcinoma by Using Nested Reverse Transcription Polymerase Chain Reaction Assay Based on Prostate-Specific Membrane Antigen," *Clin. Chem. 41*(12): 1698-1704, 1995.

Lutz et al., "Antibody Recognition of Peptide Sequences from the Cell-Cell Adhesion Proteins: N- and E-cadherins," *Peptide Research 9*(5): 233-239, 1996.

Marcozzi et al., "Coexpression of both types of desmosomal cadherin and plakoglobin confers strong intercellular adhesion," *Journal of Cell Science 111*: 495-509, 1998.

Matsuoka et al., "Recognition of Ovarian Cencer Antigen CA 125 by Murine Monoclonal Antibody Produced by Immunization of Lung Cancer Cells," *Cancer Res. 47*: 6335-6340, Dec. 1, 1987.

Matsuyoshi and Imamura, "Multiple Cadherins Are Expressd in Human Fibroblasts," *Biochemical and Biophysical Research Communications 235*: 355-358, 1997.

Mbalaviele et al., "Cadherin-6 Mediates the Heterotypic Interactions between the Hemopoietic Osteoclast Cell Lineage and Stromal Cells in a Murine Model of Osteoclast Differentiation," *The Journal of Cell Biology 141*(6): 1467-1476, Jun. 15, 1998.

Mulders et al., "Prostate-specific antigen (PSA). A tissue-specific and sensitive tumor marker," *Eur. J. Surg. Oncol. 16*: 37-41, 1990.

Munro and Blaschuk, "A Comprehensive Survey of the Cadherins Expressed in the Testes of Fetal, Immature, and Adult Mice Utilizing the Polymerase Chain Reaction," *Biology Of Reproduction 55*: 822-827, 1996.

Munro and Blashcuk, *In: Cell Adhesion and Invasion in Cancer Metastasis*, P. Brodt (ed.), RG Landes Co., Austin, Texas, 1996, Chapter 3, "The Structure, Function and Regulation of Cadherins," pp. 17-34.

Munro et al., "Characterization of Cadherins Expressed by Murine Thymocytes," *Cellular Immunology 169*: 309-312, 1996.

Munro, S.B. et al., "E-Cadherin and OB-Cadherin mRNA in Normal Human Colon and Colon Carcinoma," *Experimental and Molecular Pathology 62*(2): 118-122, Apr. 1995.

Nagafuchi et al., "Transformation of cell adhesion properties by exogenously introduced E-cadherin cDNA," *Nature 329*: 341-343, Sep. 1987.

Nagashima et al., "Invasion properties in malignant gliomas—Expression of N-cadherin mRNA in gliomas," *Proceedings of the American Association for Cancer Proceedings 37*: 38, #473, Mar. 1996.

Nakagawa and Takeichi, "Neural crest cell-cell adhesion controlled by sequential and subpopulation-specific expression of novel cadherins," *Development 121*: 1321-1332, 1995.

Navarro et al., "Differential Localization of VE- and N-Cadherins in Human Endothelial Cells: VE-Cadherin Competes with N-Cadherin for Junctional Localization," *The Journal of Cell Biology 140*(6): 1475-1484, Mar. 23, 1998.

Ngo et al., "Computational Complexity, Protein Structure Prediction, and the Levinthal Paradox," *The Protein Folding Problem and Tertiary Structure Prediction*, K. Merz, Jr. and S. Le Grand (eds.), Birkhäuser, Boston, pp. 491-495, 1994.

Okazaki et al., "Molecular Cloning and Characterization of OB-cadherin, a New Member of Cadherin Family Expressed in Osteoblasts," *The Journal of Biological Chemistry 269*(16): 12092-12098, Apr. 22, 1994.

Parker et al., "Desmosomal Glycoproteins II and III. Cadherin-Like Junctional Molecules Generated By Alternative Splicing" *The Journal of Biological Chemistry 266*(16): 10438-10445, Jan. 1991.

Pishvaian, M.J., et al., "Cadherin-11 Is Expressed in Invasive Breast Cancer Cell Lines," *Cancer Research 59*: 947-952, Feb. 15, 1999.

Pouliot et al., "Developmental Regulation of A Cadherin during the Differentiation of Skeletal Myoblasts," *Developmental Biology 141*: 292-298, 1990.

Ranscht and Bronner-Fraser, "T-cadherin expression alternates with migrating neural crest cells in the trunk of the avian embryo," *Development 111*: Jan. 15-22, 1991.

Ranscht and Dours-Zimmermann, "T-Cadherin, A Novel Cadherin Cell Adhesion Molecule in the Nervous System Lacks the Conserved Cytoplasmic Region," *Neruon 7*: 391-402, Sep. 1991.

Redies and Takechi, "Cadherins in the Developing Central Nervous System: An Adhesive Code for Segmental and Functional Subdivisions," *Developmental Biology 180*: 413-423, 1996.

Rozdzinski et al., Antiinflammatory Effects in Experimental Meningitis of Prokaryotic Peptides that Mimic Selectins, *J. Infect. Dis. 168*:1422-1428, 1993.

Rustin et al., "Defining Response of Ovarian Carcinoma to Initial Chemotherapy According to Serum CA 125," *J. Clin. Oncol. 14*(5): 1545-1551, May 1996.

Sacristán et al., "T-Cadherin 2: Molecular Characterization, Function in Cell Adhesion, and Coexpression With T-Cadherin and N-Cadherin," *Journal of Neuroscience Research 34*: 664-680, 1993.

Saffell et al., "Expression of a Dominant Negative FGF Receptor Inhibits Axonal Growth and FGF Receptor Phosphorylation Stimulated by CAMS," *Neuron 18*: 231-242, 1997.

Sano et al., "Protcadherins: a large family of cadherin-related molecules in central nervous system," *The EMBO Journal 12*(6): 2249-2256, 1993.

Shibata et al., "Identification of Human Cadherin-14, a Novel Neurally Specific Type II Cadherin, by Protein Interaction Cloning," *The Journal Of Biological Chemistry 272*(8): 5236-5240, Feb. 21, 1997.

Shibata et al., "Simultaneous expression of cadherin-11 in signet-ring cell carcinoma and stormal cells of diffuse-type gastric cancer,"*Cancer Letters 99*: 147-153, 1996.

Shimazui et al., "Complex Cadherin Expression in Renal Cell Carcinoma," *Cancer Research 56*: 3234-3237, Jul. 15, 1996.

Shimoyama et al., "Isolation and Sequence Analysis of Human Cadherin-6 Complementary DNA for the Full Coding Sequence and Its Expression in Human Carcinoma Cells," *Cancer Research 55*: 2206-2211, May 15, 1995.

Shimoyama et al., "Molecular Cloning and Charcterization of a Novel Human Classic Cadherin Homolgous with Mouse Muscle Cadherin," *The Journal of Biological Chemistry 273*(16): 10011-10018, Apr. 17, 1998.

Simmonneau et al., "Caherin 11 Expression Marks the Mesenchymal Phenotype: Towards New Functions for Cadherins?," *Cell Adhesion and Communication 3*: 115-130, 1995.

Slootstra et al., "Structural Aspects of Antibody-Antigen Interaction Revealed Through Small Random Peptide Libraries," *Molecular Diversity 1*: 87-96, 1995.

Sugimoto et al., "Molecular Cloning and Characterization of a Newly Identified Member of the Cadherin Family, PB-cadherin," *The Journal Of Biological Chemistry 271*(19): 11548-11556, May 10, 1996.

Suzuki et al., "Diversity of the cadherin family: evidence for eight new cadherins in nervous tissue," *Cell Regulation 2*: 261-270, Apr. 1991.

Taber's Cyclopedic Medical Dictionary, 17th Ed., F.A. Davis Company, Philadelphia, 1993, p. 1016.

Tanihara et al., "Cloning of Five Human Cadherins Clarifies Characteristic Features of Cadherin Extracellular Domain and Provides Further Evidence for Two Structurally Different Types of Cadherin," *Cell Adhesion and Communication 2*: 15-26, 1994.

The Merck Manual of Diagnosis and Therapy, 16th ED., Berkow, R. et al. (eds.), Merck Research Laboratories, Rahway, NJ, 1992, pp. 1264-1265.

Tkachuk et al., "Identification of an atypical lipoprotein-binding protein from human aortic smooth muscle as T-cadherin," *FEBS Letter 421*: 208-212, 1998.

Tsutsui et al., "Expression of Cadherin-Catenin Complexes in Human Leukemia Cell Lines," *Journal of Biochemistry 120*(5): 1034-1039, Nov. 1996.

Vallin, J. et al., "*Xenopus* cadherin-11 is expressed in different populations of migrating neural crest cells," *Mechanisms of Development 75*(1-2): 171-174, Jul. 1998.

Van Den Brüle et al., "Genes Involved in Tumor Invasion and Metastasis are Differentially Modulated by Estradiol and Progestin in Human Breast-Cancer Cells," *Int. J. Cancer 52*: 653-657, Oct. 1992.

Vestal and Ranscht, "Glycosyl Phosphatidylinositol-anchored T-Cadherin Mediates Calcium-dependent, Homophilic Cell Adhesion," *The Journal of Cell Biology 119*(2): 451-461, Oct. 1992.

Ward and Mulligan, "Blocking of Adhesion Molecules In Vivo as Anti-Inflammatory Therapy," *Therapeutic Immunology 1*: 165-171, 1994.

Wheeler et al., "Desmosomal glycoprotein DGI, a component of intercellular desmosome junctions, is related to the cadherin family of cell adhesion molecules," *Proc. Natl. Acad. Sci. USA 88*: 4796-4800, Jun. 1991.

Wheelock, M.J. et al., "Soluble 80-kd Fragment of Cell-CAM 120/80 Disrupts Cell-Cell Adhesion," *Journal of Cellular Biochemistry 34*: 187-202, 1987.

Williams et al., "Activation of the FGF Receptor Underlies Neurite Outgrowth Stimulated by L1, N-CAM, and N-Cadherin," *Neuron 13*: 583-594, Sep. 1994.

Alexander, J.S. et al., "An N-cadherin-like protein contributes to solute barrier maintenance in cultured endothelium," *J. Cell Physiol. 156*(3): 610-618, Sep. 1993.

Blaschuk, O.W. et al., "Identification of a conserved region common to cadherins and influenza strain A hemagglutinins," *J. Mol. Biol. 211*(4): 679-682, Feb. 1990.

Cardarelli, P.M. et al., "The Collagen Receptor $\alpha 2\beta 1$, from MG-63 and HT1080 Cells, Interacts wtih a Cyclic RGD Peptide," *The Journal of Biological Chemistry 267*(15): 23159-23164, Nov. 15, 1992.

Carmeliet, P. et al., "Angiogenesis in cancer and other diseases," *Nature 407*: 249-257, Sep. 14, 2000.

Carmeliet, P. et al., "Targeted deficiency of cytosolic truncation of the VE-cadherin gene in mice impairs VEGF-mediated endothelial survival and angiogenesis," *Cell 98*(2): 147-157, Jul. 1999.

Dvorak, H.F., "Vascular Permeabiligy Factor/Vascular Endothelial Growth Factor: A Critical Cytokine in Tumor Angiogenesis and a Potential Target for Diagnosis and Therapy," *Journal of Clinical Oncology 20*(21): 4368-4380, Nov. 1, 2002.

Erez, N. et al., "Induction of apoptosis in cultured endothelial cells by a cadherin antagonist peptide: Involvement of fibroblast growth factor receptor-mediated signalling," *Experimental Cell Research 294*(2): 366-378, Apr. 2004.

Feltes, C.M. et al., "An Alternatively Spliced Cadherin-11 Enhances Human Breast Cancer Cell Invasion," *Cancer Research 62*: 6688-6697, Nov. 15, 2002.

Garrod, D.R. et al., "Desmosomal cadherins," *Current Opinion in Cell Biology 14*: 537-545, 2002.

Genbank Database, Accession No. AB03502, Aug. 8, 2000.
Genbank Database, Accession No. AF039747, Jul. 17, 1999.
Genbank Database, Accession No. AF217289, Oct. 17, 2000.
Genbank Database, Accession No. AJ007607, Jan. 16, 2001.
Genbank Database, Accession No. AY192158, Jun. 7, 2003.
Genbank Database, Accession No. AY192159, Jun. 7, 2003.
Genbank Database, Accession No. AY227349, Jun. 5, 2003.
Genbank Database, Accession No. AY227350, Jun. 5, 2003.
Genbank Database, Accession No. P55287, Oct. 1, 1996.
Genbank Database, Accession No. Q02413, Oct. 1, 1993.
Genbank Database, Accession No. S64273, Jul. 19, 1993.
Genbank Database, Accession No. Z34522, Jun. 22, 1994.

Kashima, T. et al., "Anomalous Cadherin Expression in Osterosarcoma. Possible Relationships to Metastasis and Morphogenesis," *Amerincan Journal of Pathology 155*(5): 1549-1555, Nov. 1999.

Kawaguchi, J. et al., "Targeted disruption of cadherin-11 leads to a reduction of bone density in calvaria and long bone metaphyses," *J. Bone Mineral Research 16*(7): 1265-1271, Jul. 2001.

Kools, P. et al., "Characterization of three novel human cadherin genes (CDH7, CHD19, CDH20) clustered on chromosome 18q22-q23 and with high homology to chicken cadherin-7," *Genomics 68*(3): 283-295, Sep. 15, 2000.

Kools, P. et al., "The human cadherin-10 gene: complete coding sequence, predominant expression in the brain, and mapping on chromosome 5p13-14," *FEBS Letters 452*: 328-334, 1999.

Lampugnani, M.G. et al., "The Molecular Organization of Endothelial Cell to Cell Junctions: Differential Association of Plakoglobin, $\beta$-catenin, and $\alpha$-catenin with Vascular Endothelial Cadherin (VE-cadherin)," *The Journal of Cell Biology 129*(1): 203-217, Apr. 1995.

Makrigiannakis, A. et al., "N-Cadherin-Mediated Human Granulosa Cell Adhesion Prevents Apoptosis. A Role in Follicular Atresia and Luteolysis?" *American Journal of Pathology 154*(5): 1391-1406, May 1999.

Manabe, T. et al., "Loss of cadherin-11 adhesion receptor enhances plastic changes in hippocampal synapses and modifies behavioral responses," *Mol. Cell Neurosci 15*(6): 534-546, Jun. 2000.

Martin-Padura, I. et al., "Junctional Adhesion Moleculem, a Novel Member of the Immunoglobulin Superfamily That Distributes at Intercellular Junctions and Modulates Monocyte Transmigration," *The Journal of Cell Biology 142*(1): 117-127, Jul. 13, 1998.

Mundy, G.R., "Metastasis to bone: causes, consequences and therapeutic opportunities," *Nature Reviews. Cancer 2*(8): 584-593, Aug. 2002.

Nieman, M.T. et al., "N-Cadherin Promotes Motility in Human Breast Cancer Cells Regardless of their E-Cadherin Expression," *The Journal of Cell Biology 147*(3): 631-643, Nov. 1, 1999.

Nollet, F. et al., "Phylogenetic analysis of the cadherin superfamily allows identification of six major subfamilies besides several solitary members," *J. Mol. Biol. 299*(3): 551-572, Jun. 2000.

Orlandini, M. et al., "In Fibroblast *Vegf-D* Expression Is Induced by Cell-Cell Contact Mediated by Cadherin-11," *The Journal of Biological Chemistry 276*(9): 6576-6581, Mar. 2, 2001.

Pertz, O. et al., "A new crystal structure, $Ca^{2+}$ dependence and mutational analysis reveal molecular details of E-cadherin homoassociation," *The EMBO Journal 18*(7): 1738-1747, 1999.

Rowlands, T.M. et al., "Cadherins: crucial regulators of structure and function in reproductive tissues," *Reviews of Reproduction 5*: 53-61, 2000.

Schnädelbach, O. et al., "N-cadherin influences migration of oligodendrocytes on astrocyte monolayers," *Mol. Cell Neurosci. 15*(3): 288-302, Mar. 2000.

Schnädelbach, O. et al., "N-cadherin is involved in axon-oligodendrocyte contact and myelination," *Mol. Cell Neurosci. 17*(6): 1084-1093, Jun. 2001.

Shapiro, L. et al., "Structural basis of cell-cell adhesion by cadherins," *Nature 374*: 327-337, Mar. 23, 1995.

Shimoyama, Y. et al., "Identification of threee human type-II classic cadherins and frequent heterophilic interactions between different subclasses of type-II classic cadherins," *Biochemical Journal 349*: 159-167, 2000.

Tselepis, C. et al., "Desmosomal adhesion inhibits invasive behavior," *Proc. Natl. Acad. Sci.* USA 95: 8064-8069, Jul. 1998.

Wilby, M.J. et al., "N-Cadherin inhibits Schwann cell migration on astrocytes," *Mol. Cell Neurosci.* 14(1): 66-84, Jul. 1999.

Zanetti, A. et al., "Vascular Endothelial Growth Factor Induces Shc Association With Vascular Endothelial Cadherin. A Potential Feedback Mechanism to Control Vasculr Endothelial Growth Factor Receptor-2 Signaling," *Arterioscler. Thromb. Vasc. Biol. 22*: 617-622, Apr. 2002.

Tam, J.P. et al., "Thia Zip Reaction for Synthesis of Large Cyclic Peptides: Mechanisms and Applications," *Journal of the American Chemical Society*, 121:4316-4324, 1999.

Yu, Q. et al., "Engineered Salt-insensitive α-Defensins with End-to-end Circularized Structures," *The Journal of Biological Chemistry*, 275(6):3943-3949, Feb. 11, 2000.

\* cited by examiner

```
Human   G W V W N Q F F V I E E Y T G P D P V L V G R L H S D I D S G D G N I K Y I L S G E G A G
Mouse   G W V W N Q F F V I E E Y T G P D P V L V G R L H S D I D S G D G N I K Y I L S G E G A G
Chicken G W V W N Q F F V I E E Y T G P D P V L V G R L H S D I D S G D G N I K Y I L S G E G A G Human   T I F V I D D K S G N I H A T K T L D R E E R A Q Y T L M A Q A V D R D T N R P L E P P S
Mouse   T I F V I D D K S G N I H A T K T L D R E E R A Q Y T L M A Q A V D R D T N R P L E P P S
Chicken I I F V I D D K S G N I H A T K T L D R E E R A Q Y T L T A Q A V D R N T N R P L E P P S Human   E F I V K V Q D I N D N P P E F
Mouse   E F I V K V Q D I N D N P P E F
Chicken E F I V K V Q D I N D N P P E F
```

*FIG. 1*

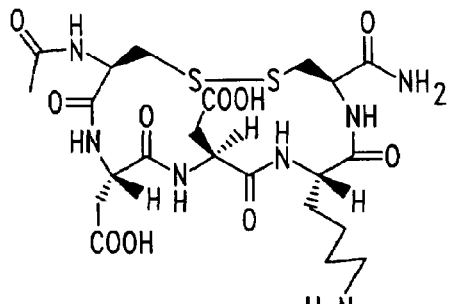
N-Ac-CDDKC-NH$_2$
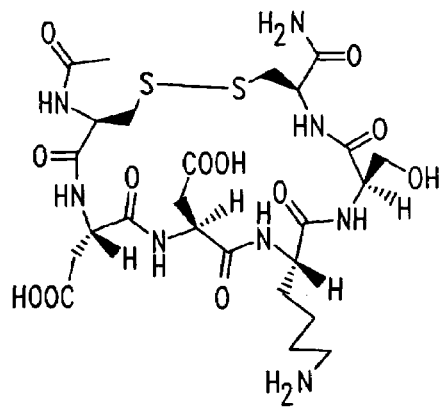
N-Ac-CDDKSC-NH$_2$
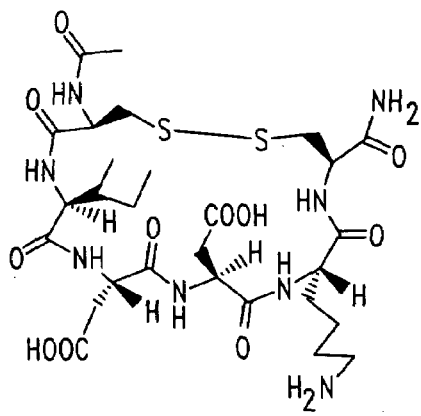
N-Ac-CIDDKC-NH$_2$
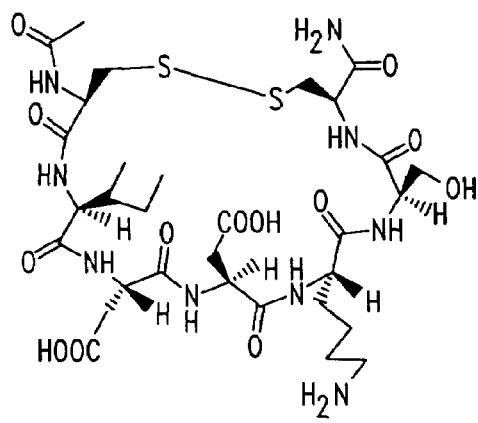
N-Ac-CIDDKSC-NH$_2$
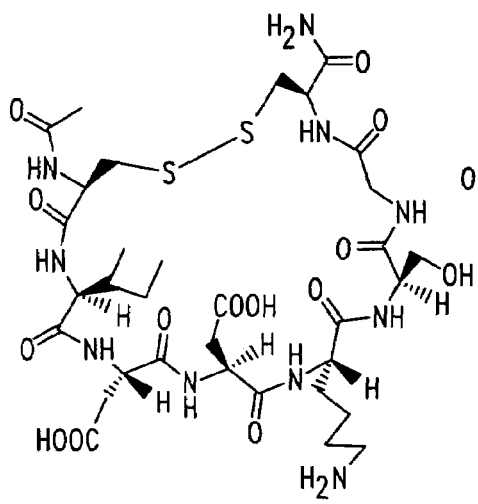
N-Ac-CIDDKSGC-NH$_2$
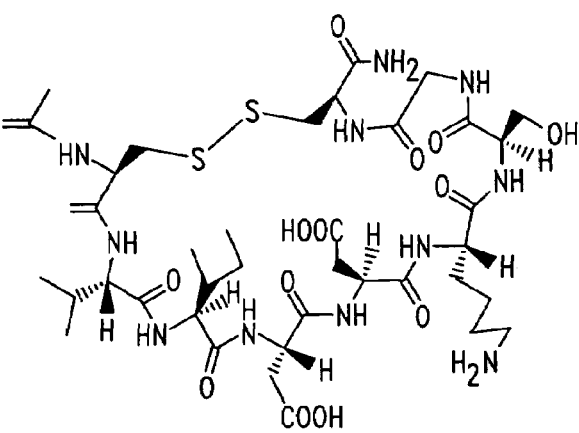
N-Ac-CVIDDKSGC-NH$_2$
FIG. 2B

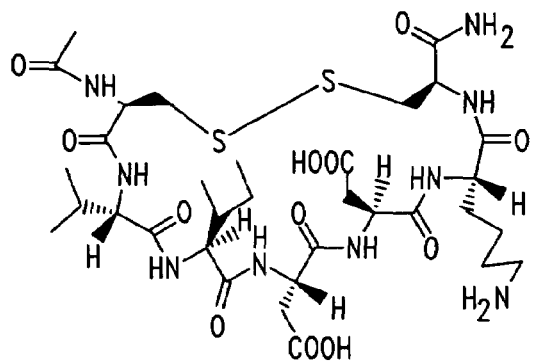
N-Ac-CVIDDKC-NH$_2$
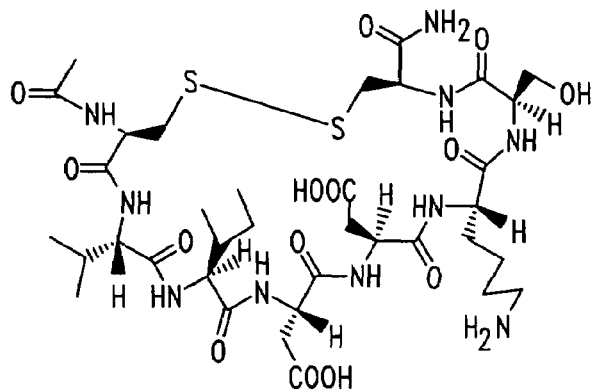
N-Ac-CVIDDKSC-NH$_2$
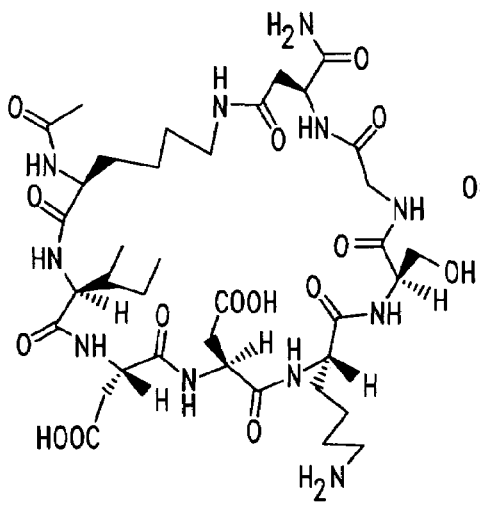
N-Ac-KIDDKSGD-NH$_2$
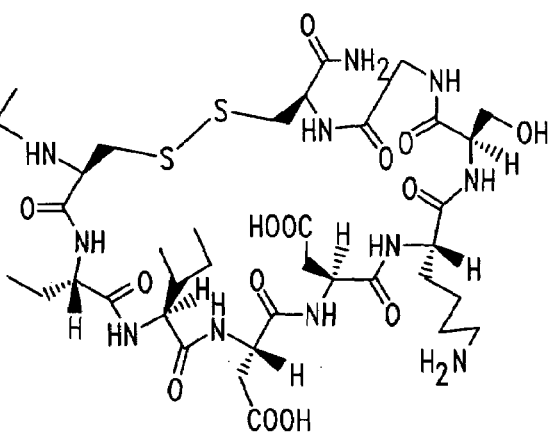
N-Ac-CVIDDKSGC-NH$_2$
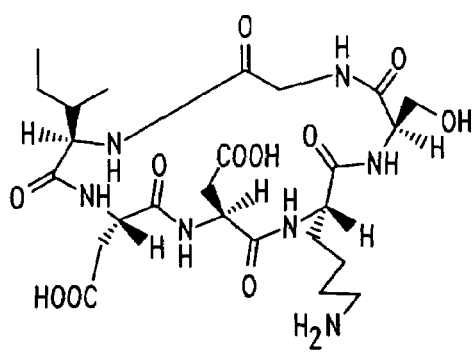
N-Ac-IDDKSG-NH$_2$
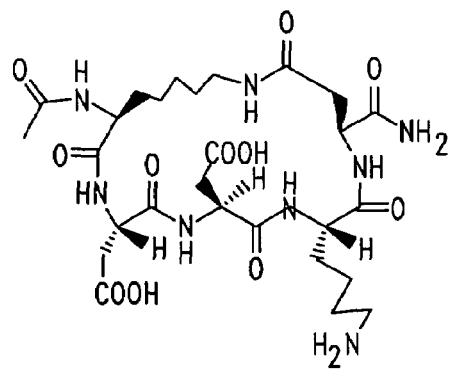
N-Ac-KDDKD-NH$_2$
*FIG. 2C*

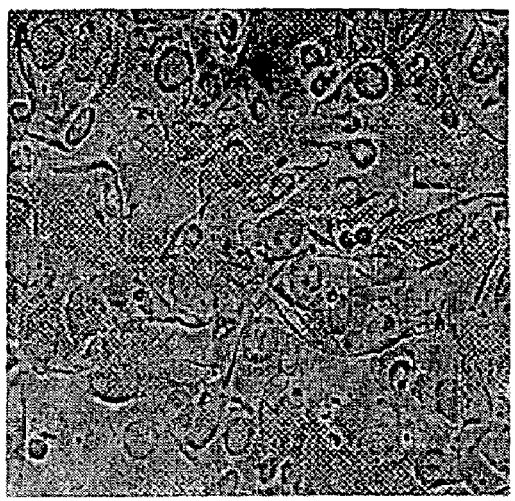 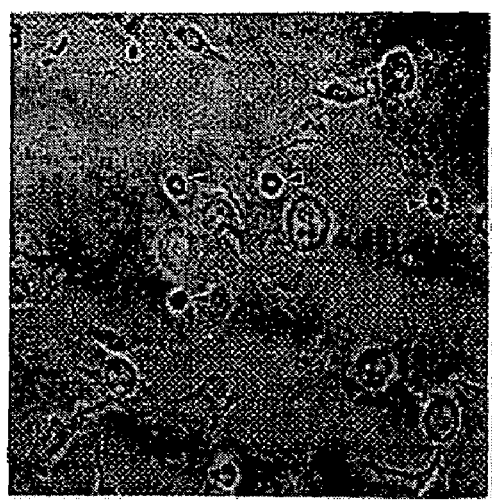
*FIG. 3A*   *FIG. 3B*
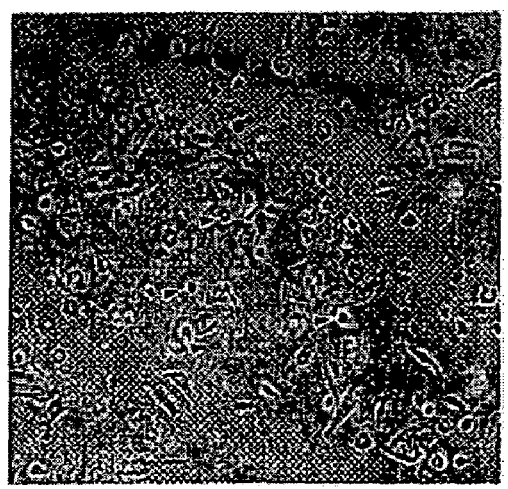
*FIG. 3C*

SEQUENCE LISTING

<160> NUMBER OF SEQ ID NOS: 322

<210> SEQ ID NO 1
<211> LENGTH: 5
<212> TYPE: PRT
<213> ORGANISM: Unknown
<220> FEATURE:
<223> OTHER INFORMATION: Calcium binding motif
<220> FEATURE:
<221> NAME/KEY: VARIANT
<222> LOCATION: 2
<223> OTHER INFORMATION: Xaa = Any Amino Acid

<400> SEQUENCE: 1

Asp Xaa Asn Asp Asn
 1               5

<210> SEQ ID NO 2
<211> LENGTH: 4
<212> TYPE: PRT
<213> ORGANISM: unknown
<220> FEATURE:
<223> OTHER INFORMATION: Calcium binding motif

<400> SEQUENCE: 2

Leu Asp Arg Glu
 1

<210> SEQ ID NO 3
<211> LENGTH: 9
<212> TYPE: PRT
<213> ORGANISM: Artificial Sequence
<220> FEATURE:
<223> OTHER INFORMATION: OB-cadherin modulating agent
<220> FEATURE:
<221> NAME/KEY: VARIANT
<222> LOCATION: 1,3,6,7
<223> OTHER INFORMATION: Xaa = any amino acid
<220> FEATURE:
<221> NAME/KEY: VARIANT
<222> LOCATION: 4
<223> OTHER INFORMATION: Xaa = Ile, Leu or Val
<220> FEATURE:
<221> NAME/KEY: VARIANT
<222> LOCATION: 5
<223> OTHER INFORMATION: Xaa = Asp, Asn or Glu
<220> FEATURE:
<221> NAME/KEY: VARIANT
<222> LOCATION: 8
<223> OTHER INFORMATION: Xaa = Ser, Thr or Asn

<400> SEQUENCE: 3

Xaa Phe Xaa Xaa Xaa Xaa Xaa Xaa Gly
 1               5

<210> SEQ ID NO 4
<211> LENGTH: 4
<212> TYPE: PRT
<213> ORGANISM: Unknown
<220> FEATURE:
<223> OTHER INFORMATION: Preferred OB-cadherin cell adhesion
      recognition sequence for inclusion within modulating agent

<400> SEQUENCE: 4

Ile Asp Asp Lys
 1

<210> SEQ ID NO 5

```
<211> LENGTH: 4
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 5

Asp Asp Lys Ser
 1

<210> SEQ ID NO 6
<211> LENGTH: 5
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 6

Val Ile Asp Asp Lys
 1               5

<210> SEQ ID NO 7
<211> LENGTH: 5
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 7

Ile Asp Asp Lys Ser
 1               5

<210> SEQ ID NO 8
<211> LENGTH: 6
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 8

Val Ile Asp Asp Lys Ser
 1               5

<210> SEQ ID NO 9
<211> LENGTH: 5
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 9

Asp Asp Lys Ser Gly
 1               5

<210> SEQ ID NO 10
<211> LENGTH: 6
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 10
```

```
<210> SEQ ID NO 11
<211> LENGTH: 7
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 11

Val Ile Asp Asp Lys Ser Gly
 1               5

<210> SEQ ID NO 12
<211> LENGTH: 6
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 12

Phe Val Ile Asp Asp Lys
 1               5

<210> SEQ ID NO 13
<211> LENGTH: 7
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 13

Phe Val Ile Asp Asp Lys Ser
 1               5

<210> SEQ ID NO 14
<211> LENGTH: 8
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 14

Phe Val Ile Asp Asp Lys Ser Gly
 1               5

<210> SEQ ID NO 15
<211> LENGTH: 7
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 15

Ile Phe Val Ile Asp Asp Lys
 1               5

<210> SEQ ID NO 16
<211> LENGTH: 8
<212> TYPE: PRT
<213> ORGANISM: unknown
<220> FEATURE:
```

(continued from previous page)

```
Ile Asp Asp Lys Ser Gly
 1               5
```

```
<223> OTHER INFORMATION: Preferred  OB-cadherin cell adhesion
      recognition sequence for inclusion within modulating agent

<400> SEQUENCE: 16

Ile Phe Val Ile Asp Asp Lys Ser
1               5

<210> SEQ ID NO 17
<211> LENGTH: 9
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 17

Ile Phe Val Ile Asp Asp Lys Ser Gly
1               5

<210> SEQ ID NO 18
<211> LENGTH: 4
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 18

Ile Glu Glu Tyr
1

<210> SEQ ID NO 19
<211> LENGTH: 4
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 19

Glu Glu Tyr Thr
1

<210> SEQ ID NO 20
<211> LENGTH: 5
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 20

Val Ile Glu Glu Tyr
1               5

<210> SEQ ID NO 21
<211> LENGTH: 5
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 21

Ile Glu Glu Tyr Thr
1               5
```

```
<210> SEQ ID NO 22
<211> LENGTH: 6
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 22

Val Ile Glu Glu Tyr Thr
1               5

<210> SEQ ID NO 23
<211> LENGTH: 5
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 23

Glu Glu Tyr Thr Gly
1               5

<210> SEQ ID NO 24
<211> LENGTH: 6
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 24

Ile Glu Glu Tyr Thr Gly
1               5

<210> SEQ ID NO 25
<211> LENGTH: 7
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 25

Val Ile Glu Glu Tyr Thr Gly
1               5

<210> SEQ ID NO 26
<211> LENGTH: 6
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 26

Phe Val Ile Glu Glu Tyr
1               5

<210> SEQ ID NO 27
<211> LENGTH: 7
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 27
```

```
Phe Val Ile Glu Glu Tyr Thr
1               5

<210> SEQ ID NO 28
<211> LENGTH: 8
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 28

Phe Val Ile Glu Glu Tyr Thr Gly
1               5

<210> SEQ ID NO 29
<211> LENGTH: 7
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 29

Phe Phe Val Ile Glu Glu Tyr
1               5

<210> SEQ ID NO 30
<211> LENGTH: 8
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 30

Phe Phe Val Ile Glu Glu Tyr Thr
1               5

<210> SEQ ID NO 31
<211> LENGTH: 9
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 31

Phe Phe Val Ile Glu Glu Tyr Thr Gly
1               5

<210> SEQ ID NO 32
<211> LENGTH: 4
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 32

Val Glu Ala Gln
1

<210> SEQ ID NO 33
<211> LENGTH: 4
<212> TYPE: PRT
<213> ORGANISM: unknown
```

```
<220> FEATURE:
<223> OTHER INFORMATION: Preferred  OB-cadherin cell adhesion
      recognition sequence for inclusion within modulating agent

<400> SEQUENCE: 33

Glu Ala Gln Thr
1

<210> SEQ ID NO 34
<211> LENGTH: 5
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 34

Ser Val Glu Ala Gln
1               5

<210> SEQ ID NO 35
<211> LENGTH: 5
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 35

Val Glu Ala Gln Thr
1               5

<210> SEQ ID NO 36
<211> LENGTH: 6
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 36

Ser Val Glu Ala Gln Thr
1               5

<210> SEQ ID NO 37
<211> LENGTH: 5
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 37

Glu Ala Gln Thr Gly
1               5

<210> SEQ ID NO 38
<211> LENGTH: 6
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 38

Val Glu Ala Gln Thr Gly
1               5
```

```
<210> SEQ ID NO 39
<211> LENGTH: 7
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 39

Ser Val Glu Ala Gln Thr Gly
 1               5

<210> SEQ ID NO 40
<211> LENGTH: 6
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 40

Phe Ser Val Glu Ala Gln
 1               5

<210> SEQ ID NO 41
<211> LENGTH: 7
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 41

Phe Ser Val Glu Ala Gln Thr
 1               5

<210> SEQ ID NO 42
<211> LENGTH: 8
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 42

Phe Ser Val Glu Ala Gln Thr Gly
 1               5

<210> SEQ ID NO 43
<211> LENGTH: 7
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 43

Tyr Phe Ser Val Glu Ala Gln
 1               5

<210> SEQ ID NO 44
<211> LENGTH: 8
<212> TYPE: PRT
<213> ORGANISM: unknown
<220> FEATURE:
<223> OTHER INFORMATION: Preferred  OB-cadherin cell adhesion
      recognition sequence for inclusion within modulating agent
```

-continued

```
<400> SEQUENCE: 44

Tyr Phe Ser Val Glu Ala Gln Thr
 1               5

<210> SEQ ID NO 45
<211> LENGTH: 9
<212> TYPE: PRT
<213> ORGANISM: unknown
<220> FEATURE:
<223> OTHER INFORMATION: Preferred  OB-cadherin cell adhesion
      recognition sequence for inclusion within modulating agent

<400> SEQUENCE: 45

Tyr Phe Ser Val Glu Ala Gln Thr Gly
 1               5

<210> SEQ ID NO 46
<211> LENGTH: 10
<212> TYPE: PRT
<213> ORGANISM: UNKNOWN
<220> FEATURE:
<223> OTHER INFORMATION: Preferred  OB-cadherin cell adhesion
      recognition sequence for inclusion within modulating agent

<400> SEQUENCE: 46

Leu Met Ala Gln Ala Val Asp Arg Asp Thr
 1               5                  10

<210> SEQ ID NO 47
<211> LENGTH: 4
<212> TYPE: PRT
<213> ORGANISM: UNKNOWN
<220> FEATURE:
<223> OTHER INFORMATION: Calcium binding motif
<220> FEATURE:
<221> NAME/KEY: VARIANT
<222> LOCATION: 1, 3
<223> OTHER INFORMATION: Xaa = Any Amino Acid

<400> SEQUENCE: 47

Xaa Asp Xaa Glu
 1

<210> SEQ ID NO 48
<211> LENGTH: 5
<212> TYPE: PRT
<213> ORGANISM: Unknown
<220> FEATURE:
<223> OTHER INFORMATION: Calcium binding motif
<220> FEATURE:
<221> NAME/KEY: VARIANT
<222> LOCATION: 2, 3, 5
<223> OTHER INFORMATION: Xaa = Any Amino Acid

<400> SEQUENCE: 48

Asp Xaa Xaa Asp Xaa
 1               5

<210> SEQ ID NO 49
<211> LENGTH: 4
<212> TYPE: PRT
<213> ORGANISM: unknown
<220> FEATURE:
<223> OTHER INFORMATION: Calcium binding motif

<400> SEQUENCE: 49

Met Asp Arg Glu
 1
```

<210> SEQ ID NO 50
<211> LENGTH: 4
<212> TYPE: PRT
<213> ORGANISM: unknown
<220> FEATURE:
<223> OTHER INFORMATION: Calcium binding motif

<400> SEQUENCE: 50

Leu Asp Phe Glu
 1

<210> SEQ ID NO 51
<211> LENGTH: 4
<212> TYPE: PRT
<213> ORGANISM: unknown
<220> FEATURE:
<223> OTHER INFORMATION: Calcium binding motif

<400> SEQUENCE: 51

Leu Asp Tyr Glu
 1

<210> SEQ ID NO 52
<211> LENGTH: 4
<212> TYPE: PRT
<213> ORGANISM: unknown
<220> FEATURE:
<223> OTHER INFORMATION: Calcium binding motif

<400> SEQUENCE: 52

Ile Asp Arg Glu
 1

<210> SEQ ID NO 53
<211> LENGTH: 4
<212> TYPE: PRT
<213> ORGANISM: unknown
<220> FEATURE:
<223> OTHER INFORMATION: Calcium binding motif

<400> SEQUENCE: 53

Val Asp Arg Glu
 1

<210> SEQ ID NO 54
<211> LENGTH: 4
<212> TYPE: PRT
<213> ORGANISM: unknown
<220> FEATURE:
<223> OTHER INFORMATION: Calcium binding motif

<400> SEQUENCE: 54

Ile Asp Phe Glu
 1

<210> SEQ ID NO 55
<211> LENGTH: 11
<212> TYPE: PRT
<213> ORGANISM: unknown
<220> FEATURE:
<223> OTHER INFORMATION: Third calcium binding motif
<220> FEATURE:
<221> NAME/KEY: VARIANT
<222> LOCATION: 1
<223> OTHER INFORMATION: Xaa = Leu, Ile or Val
<220> FEATURE:
<221> NAME/KEY: VARIANT

```
<222> LOCATION: 2,4,6,10
<223> OTHER INFORMATION: Xaa = any amino acid
<220> FEATURE:
<221> NAME/KEY: VARIANT
<222> LOCATION: 3
<223> OTHER INFORMATION: Xaa = Leu, Ile of Val
<220> FEATURE:
<221> NAME/KEY: VARIANT
<222> LOCATION: 9
<223> OTHER INFORMATION: Xaa = Asn or His
<220> FEATURE:
<221> NAME/KEY: VARIANT

<400> SEQUENCE: 55

Xaa Xaa Xaa Xaa Asp Xaa Asn Asp Xaa Xaa Pro
 1               5                  10

<210> SEQ ID NO 56
<211> LENGTH: 12
<212> TYPE: PRT
<213> ORGANISM: unknown
<220> FEATURE:
<223> OTHER INFORMATION: OB-cadherin consensus sequence
<220> FEATURE:
<221> NAME/KEY: VARIANT
<222> LOCATION: 2
<223> OTHER INFORMATION: Xaa = Thr, Ile or Val
<220> FEATURE:
<221> NAME/KEY: VARIANT
<222> LOCATION: 4
<223> OTHER INFORMATION: Xaa = Met, Thr, Arg or Leu
<220> FEATURE:
<221> NAME/KEY: VARIANT
<222> LOCATION: 9
<223> OTHER INFORMATION: Xaa = Asp or Asn
<220> FEATURE:
<221> NAME/KEY: VARIANT
<222> LOCATION: 10
<223> OTHER INFORMATION: Xaa = Arg, Phe, Trp or Ile
<220> FEATURE:
<221> NAME/KEY: VARIANT
<222> LOCATION: 11
<223> OTHER INFORMATION: Xaa = Asp, Asn Glu, Arg or Ala
<220> FEATURE:
<221> NAME/KEY: VARIANT
<222> LOCATION: 12
<223> OTHER INFORMATION: Xaa = Thr or Ser

<400> SEQUENCE: 56

Tyr Xaa Leu Xaa Ala Gln Ala Val Xaa Xaa Xaa Xaa
 1               5                  10

<210> SEQ ID NO 57
<211> LENGTH: 5
<212> TYPE: PRT
<213> ORGANISM: Artificial Sequence
<220> FEATURE:
<223> OTHER INFORMATION: Cyclic peptides that may be used as modulating
      agents without modification or may be incorporated
      into a modulating agent.

<400> SEQUENCE: 57

Cys Asp Asp Lys Cys
 1               5

<210> SEQ ID NO 58
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
```

```
<400> SEQUENCE: 58

Cys Ile Asp Asp Lys Cys
1               5

<210> SEQ ID NO 59
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 59

Cys Asp Asp Lys Ser Cys
1               5

<210> SEQ ID NO 60
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 60

Cys Val Ile Asp Asp Lys Cys
1               5

<210> SEQ ID NO 61
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 61

Cys Ile Asp Asp Lys Ser Cys
1               5

<210> SEQ ID NO 62
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 62

Cys Val Ile Asp Asp Lys Ser Cys
1               5

<210> SEQ ID NO 63
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 63

Cys Asp Asp Lys Ser Gly Cys
```

-continued

```
<210> SEQ ID NO 64
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 64

Cys Ile Asp Asp Lys Ser Gly Cys
1               5

<210> SEQ ID NO 65
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 65

Cys Val Ile Asp Asp Lys Ser Gly Cys
1               5

<210> SEQ ID NO 66
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 66

Cys Phe Val Ile Asp Asp Lys Cys
1               5

<210> SEQ ID NO 67
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 67

Cys Phe Val Ile Asp Asp Lys Ser Cys
1               5

<210> SEQ ID NO 68
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 68

Cys Phe Val Ile Asp Asp Lys Ser Gly Cys
1               5                   10

<210> SEQ ID NO 69
```

```
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 69

Cys Ile Phe Val Ile Asp Asp Lys Cys
 1               5

<210> SEQ ID NO 70
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 70

Cys Ile Phe Val Ile Asp Asp Lys Ser Cys
 1               5                  10

<210> SEQ ID NO 71
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 71

Cys Ile Phe Val Ile Asp Asp Lys Ser Gly Cys
 1               5                  10

<210> SEQ ID NO 72
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 72

Asp Asp Asp Lys Lys
 1               5

<210> SEQ ID NO 73
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 73

Asp Ile Asp Asp Lys Lys
 1               5

<210> SEQ ID NO 74
<211> LENGTH: 7
<212> TYPE: PRT
<213> ORGANISM: Artificial Sequence
<220> FEATURE:
```

```
<223> OTHER INFORMATION: Cyclic peptide that may be used as a modulating
      agent without modification or may be incorporated
      into a modulating agent.

<400> SEQUENCE: 74

Asp Val Ile Asp Asp Lys Lys
1               5

<210> SEQ ID NO 75
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 75

Asp Phe Val Ile Asp Asp Lys Lys
1               5

<210> SEQ ID NO 76
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 76

Asp Ile Phe Val Ile Asp Asp Lys Lys
1               5

<210> SEQ ID NO 77
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 77

Glu Asp Asp Lys Lys
1               5

<210> SEQ ID NO 78
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 78

Glu Ile Asp Asp Lys Lys
1               5

<210> SEQ ID NO 79
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
```

```
<400> SEQUENCE: 79

Glu Val Ile Asp Asp Lys Lys
 1               5

<210> SEQ ID NO 80
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 80

Glu Phe Val Ile Asp Asp Lys Lys
 1               5

<210> SEQ ID NO 81
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 81

Glu Ile Phe Val Ile Asp Asp Lys Lys
 1               5

<210> SEQ ID NO 82
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 82

Phe Val Ile Asp Asp Lys
 1               5

<210> SEQ ID NO 83
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 83

Phe Val Ile Asp Asp Lys Ser
 1               5

<210> SEQ ID NO 84
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 84

Phe Val Ile Asp Asp Lys Ser Gly
 1               5
```

```
<210> SEQ ID NO 85
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 85

Lys Asp Asp Lys Asp
 1               5

<210> SEQ ID NO 86
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 86

Lys Ile Asp Asp Lys Asp
 1               5

<210> SEQ ID NO 87
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 87

Lys Asp Asp Lys Ser Asp
 1               5

<210> SEQ ID NO 88
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 88

Lys Val Ile Asp Asp Lys Asp
 1               5

<210> SEQ ID NO 89
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 89

Lys Ile Asp Asp Lys Ser Asp
 1               5

<210> SEQ ID NO 90
<211> LENGTH: 8
```

```
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 90

Lys Val Ile Asp Asp Lys Ser Asp
 1               5

<210> SEQ ID NO 91
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 91

Lys Asp Asp Lys Ser Gly Asp
 1               5

<210> SEQ ID NO 92
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 92

Lys Ile Asp Asp Lys Ser Gly Asp
 1               5

<210> SEQ ID NO 93
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 93

Lys Val Ile Asp Asp Lys Ser Gly Asp
 1               5

<210> SEQ ID NO 94
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 94

Lys Phe Val Ile Asp Asp Lys Asp
 1               5

<210> SEQ ID NO 95
<211> LENGTH: 9
<212> TYPE: PRT
<213> ORGANISM: Artificial Sequence
<220> FEATURE:
<223> OTHER INFORMATION: Cyclic peptide that may be used as a modulating
```

-continued agent without modification or may be incorporated
into a modulating agent.

<400> SEQUENCE: 95

Lys Phe Val Ile Asp Asp Lys Ser Asp
 1               5

<210> SEQ ID NO 96
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 96

Lys Phe Val Ile Asp Asp Lys Ser Gly Asp
 1               5                  10

<210> SEQ ID NO 97
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 97

Lys Ile Phe Val Ile Asp Asp Lys Asp
 1               5

<210> SEQ ID NO 98
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 98

Lys Ile Phe Val Ile Asp Asp Lys Ser Asp
 1               5                  10

<210> SEQ ID NO 99
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 99

Lys Ile Phe Val Ile Asp Asp Lys Ser Gly Asp
 1               5                  10

<210> SEQ ID NO 100
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 100

Val Ile Asp Asp Lys
1               5

<210> SEQ ID NO 101
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 101

Ile Asp Asp Lys Ser
1               5

<210> SEQ ID NO 102
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 102

Val Ile Asp Asp Lys Ser
1               5

<210> SEQ ID NO 103
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 103

Val Ile Asp Asp Lys Ser Gly
1               5

<210> SEQ ID NO 104
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 104

Asp Asp Lys Ser Gly
1               5

<210> SEQ ID NO 105
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 105

Ile Asp Asp Lys Ser Gly
1               5

```
<210> SEQ ID NO 106
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 106

Ile Phe Val Ile Asp Asp Lys
1               5

<210> SEQ ID NO 107
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 107

Ile Phe Val Ile Asp Asp Lys Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 108

Ile Phe Val Ile Asp Asp Lys Ser Gly
1               5

<210> SEQ ID NO 109
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 109

Lys Asp Asp Lys Glu
1               5

<210> SEQ ID NO 110
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 110

Lys Ile Asp Asp Lys Glu
1               5

<210> SEQ ID NO 111
<211> LENGTH: 6
<212> TYPE: PRT
```

```
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 111

Lys Asp Asp Lys Ser Glu
1               5

<210> SEQ ID NO 112
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 112

Lys Val Ile Asp Asp Lys Glu
1               5

<210> SEQ ID NO 113
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 113

Lys Ile Asp Asp Lys Ser Glu
1               5

<210> SEQ ID NO 114
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 114

Lys Val Ile Asp Asp Lys Ser Glu
1               5

<210> SEQ ID NO 115
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 115

Lys Asp Asp Lys Ser Gly Glu
1               5

<210> SEQ ID NO 116
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
```

-continued into a modulating agent.

<400> SEQUENCE: 116

Lys Ile Asp Asp Lys Ser Gly Glu
  1               5

<210> SEQ ID NO 117
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 117

Lys Val Ile Asp Asp Lys Ser Gly Glu
  1               5

<210> SEQ ID NO 118
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 118

Lys Phe Val Ile Asp Asp Lys Glu
  1               5

<210> SEQ ID NO 119
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 119

Lys Phe Val Ile Asp Asp Lys Ser Glu
  1               5

<210> SEQ ID NO 120
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 120

Lys Phe Val Ile Asp Asp Lys Ser Gly Glu
  1               5                  10

<210> SEQ ID NO 121
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 121

```
Lys Ile Phe Val Ile Asp Asp Lys Glu
1               5
```

<210> SEQ ID NO 122
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 122

```
Lys Ile Phe Val Ile Asp Asp Lys Ser Glu
1               5                   10
```

<210> SEQ ID NO 123
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 123

```
Lys Ile Phe Val Ile Asp Asp Lys Ser Gly Glu
1               5                   10
```

<210> SEQ ID NO 124
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 124

```
Cys Glu Glu Tyr Cys
1               5
```

<210> SEQ ID NO 125
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 125

```
Cys Ile Glu Glu Tyr Cys
1               5
```

<210> SEQ ID NO 126
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 126

```
Cys Glu Glu Tyr Thr Cys
1               5
```

```
<210> SEQ ID NO 127
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 127

Cys Val Ile Glu Glu Tyr Cys
 1               5

<210> SEQ ID NO 128
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 128

Cys Ile Glu Glu Tyr Thr Cys
 1               5

<210> SEQ ID NO 129
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 129

Cys Val Ile Glu Glu Tyr Thr Cys
 1               5

<210> SEQ ID NO 130
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 130

Cys Glu Glu Tyr Thr Gly Cys
 1               5

<210> SEQ ID NO 131
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 131

Cys Ile Glu Glu Tyr Thr Gly Cys
 1               5

<210> SEQ ID NO 132
<211> LENGTH: 9
<212> TYPE: PRT
<213> ORGANISM: Artificial Sequence
```

-continued

```
<220> FEATURE:
<223> OTHER INFORMATION: Cyclic peptide that may be used as a modulating
      agent without modification or may be incorporated
      into a modulating agent.

<400> SEQUENCE: 132

Cys Val Ile Glu Glu Tyr Thr Gly Cys
1               5

<210> SEQ ID NO 133
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 133

Cys Phe Val Ile Glu Glu Tyr Cys
1               5

<210> SEQ ID NO 134
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 134

Cys Phe Val Ile Glu Glu Tyr Thr Cys
1               5

<210> SEQ ID NO 135
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 135

Cys Phe Val Ile Glu Glu Tyr Thr Gly Cys
1               5                   10

<210> SEQ ID NO 136
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 136

Cys Phe Phe Val Ile Glu Glu Tyr Cys
1               5

<210> SEQ ID NO 137
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
```

```
<400> SEQUENCE: 137

Cys Phe Phe Val Ile Glu Glu Tyr Thr Cys
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 138

Cys Phe Phe Val Ile Glu Glu Tyr Thr Gly Cys
1               5                   10

<210> SEQ ID NO 139
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 139

Lys Glu Glu Tyr Asp
1               5

<210> SEQ ID NO 140
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 140

Lys Ile Glu Glu Tyr Asp
1               5

<210> SEQ ID NO 141
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 141

Lys Glu Glu Tyr Thr Asp
1               5

<210> SEQ ID NO 142
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 142

Lys Val Ile Glu Glu Tyr Asp
```

-continued

```
<210> SEQ ID NO 143
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 143

Lys Ile Glu Glu Tyr Thr Asp
1               5

<210> SEQ ID NO 144
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 144

Lys Val Ile Glu Glu Tyr Thr Asp
1               5

<210> SEQ ID NO 145
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 145

Lys Glu Glu Tyr Thr Gly Cys Asp
1               5

<210> SEQ ID NO 146
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 146

Lys Ile Glu Glu Tyr Thr Gly Asp
1               5

<210> SEQ ID NO 147
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 147

Lys Val Ile Glu Glu Tyr Thr Gly Asp
1               5

<210> SEQ ID NO 148
```

```
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 148

Lys Phe Val Ile Glu Glu Tyr Asp
  1               5

<210> SEQ ID NO 149
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 149

Lys Phe Val Ile Glu Glu Tyr Thr Asp
  1               5

<210> SEQ ID NO 150
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 150

Lys Phe Val Ile Glu Glu Tyr Thr Gly Asp
  1               5                  10

<210> SEQ ID NO 151
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 151

Lys Phe Phe Val Ile Glu Glu Tyr Asp
  1               5

<210> SEQ ID NO 152
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 152

Lys Phe Phe Val Ile Glu Glu Tyr Thr Asp
  1               5                  10

<210> SEQ ID NO 153
<211> LENGTH: 11
<212> TYPE: PRT
<213> ORGANISM: Artificial Sequence
<220> FEATURE:
```

```
<223> OTHER INFORMATION: Cyclic peptide that may be used as a modulating
      agent without modification or may be incorporated
      into a modulating agent.

<400> SEQUENCE: 153

Lys Phe Phe Val Ile Glu Glu Tyr Thr Gly Asp
1               5                   10

<210> SEQ ID NO 154
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 154

Glu Glu Glu Tyr Lys
1               5

<210> SEQ ID NO 155
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 155

Glu Ile Glu Glu Tyr Lys
1               5

<210> SEQ ID NO 156
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 156

Glu Glu Glu Tyr Thr Lys
1               5

<210> SEQ ID NO 157
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 157

Glu Val Ile Glu Glu Tyr Lys
1               5

<210> SEQ ID NO 158
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
```

```
<400> SEQUENCE: 158

Glu Ile Glu Glu Tyr Thr Lys
1               5

<210> SEQ ID NO 159
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 159

Glu Val Ile Glu Glu Tyr Thr Lys
1               5

<210> SEQ ID NO 160
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 160

Glu Glu Glu Tyr Thr Gly Lys
1               5

<210> SEQ ID NO 161
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 161

Glu Ile Glu Glu Tyr Thr Gly Lys
1               5

<210> SEQ ID NO 162
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 162

Glu Val Ile Glu Glu Tyr Thr Gly Lys
1               5

<210> SEQ ID NO 163
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 163

Glu Phe Val Ile Glu Glu Tyr Lys
1               5
```

```
<210> SEQ ID NO 164
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 164

Glu Phe Val Ile Glu Glu Tyr Thr Lys
 1               5

<210> SEQ ID NO 165
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 165

Glu Phe Val Ile Glu Glu Tyr Thr Gly Lys
 1               5                  10

<210> SEQ ID NO 166
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 166

Glu Phe Phe Val Ile Glu Glu Tyr Lys
 1               5

<210> SEQ ID NO 167
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 167

Glu Phe Phe Val Ile Glu Glu Tyr Thr Lys
 1               5                  10

<210> SEQ ID NO 168
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 168

Glu Phe Phe Val Ile Glu Glu Tyr Thr Gly Lys
 1               5                  10

<210> SEQ ID NO 169
<211> LENGTH: 6
```

```
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 169

Asp Cys Glu Glu Tyr Lys
 1               5

<210> SEQ ID NO 170
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 170

Asp Ile Glu Glu Tyr Cys Lys
 1               5

<210> SEQ ID NO 171
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 171

Asp Glu Glu Tyr Thr Lys
 1               5

<210> SEQ ID NO 172
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 172

Asp Val Ile Glu Glu Tyr Lys
 1               5

<210> SEQ ID NO 173
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 173

Asp Ile Glu Glu Tyr Thr Lys
 1               5

<210> SEQ ID NO 174
<211> LENGTH: 8
<212> TYPE: PRT
<213> ORGANISM: Artificial Sequence
<220> FEATURE:
<223> OTHER INFORMATION: Cyclic peptide that may be used as a modulating
```

```
        agent without modification or may be incorporated
        into a modulating agent.

<400> SEQUENCE: 174

Asp Val Ile Glu Glu Tyr Thr Lys
1               5

<210> SEQ ID NO 175
<211> LENGTH: 7
<212> TYPE: PRT
<213> ORGANISM: Artificial Sequence
<220> FEATURE:
<223> OTHER INFORMATION: Cyclic peptide that may be used as a modulating
        agent without modification or may be incorporated
        into a modulating agent.

<400> SEQUENCE: 175

Asp Glu Glu Tyr Thr Gly Lys
1               5

<210> SEQ ID NO 176
<211> LENGTH: 8
<212> TYPE: PRT
<213> ORGANISM: Artificial Sequence
<220> FEATURE:
<223> OTHER INFORMATION: Cyclic peptide that may be used as a modulating
        agent without modification or may be incorporated
        into a modulating agent.

<400> SEQUENCE: 176

Asp Ile Glu Glu Tyr Thr Gly Lys
1               5

<210> SEQ ID NO 177
<211> LENGTH: 9
<212> TYPE: PRT
<213> ORGANISM: Artificial Sequence
<220> FEATURE:
<223> OTHER INFORMATION: Cyclic peptide that may be used as a modulating
        agent without modification or may be incorporated
        into a modulating agent.

<400> SEQUENCE: 177

Asp Val Ile Glu Glu Tyr Thr Gly Lys
1               5

<210> SEQ ID NO 178
<211> LENGTH: 8
<212> TYPE: PRT
<213> ORGANISM: Artificial Sequence
<220> FEATURE:
<223> OTHER INFORMATION: Cyclic peptide that may be used as a modulating
        agent without modification or may be incorporated
        into a modulating agent.

<400> SEQUENCE: 178

Asp Phe Val Ile Glu Glu Tyr Lys
1               5

<210> SEQ ID NO 179
<211> LENGTH: 9
<212> TYPE: PRT
<213> ORGANISM: Artificial Sequence
<220> FEATURE:
<223> OTHER INFORMATION: Cyclic peptide that may be used as a modulating
        agent without modification or may be incorporated
        into a modulating agent.

<400> SEQUENCE: 179
```

```
Asp Phe Val Ile Glu Glu Tyr Thr Lys
1               5
```

<210> SEQ ID NO 180
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 180

```
Asp Phe Val Ile Glu Glu Tyr Thr Gly Lys
1               5                   10
```

<210> SEQ ID NO 181
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 181

```
Asp Phe Phe Val Ile Glu Glu Tyr Lys
1               5
```

<210> SEQ ID NO 182
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 182

```
Asp Phe Phe Val Ile Glu Glu Tyr Thr Lys
1               5                   10
```

<210> SEQ ID NO 183
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 183

```
Asp Phe Phe Val Ile Glu Glu Tyr Thr Gly Lys
1               5                   10
```

<210> SEQ ID NO 184
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 184

```
Lys Glu Glu Tyr Glu
1               5
```

<210> SEQ ID NO 185
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 185

Lys Ile Glu Glu Tyr Glu
 1               5

<210> SEQ ID NO 186
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 186

Lys Glu Glu Tyr Thr Glu
 1               5

<210> SEQ ID NO 187
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 187

Lys Val Ile Glu Glu Tyr Glu
 1               5

<210> SEQ ID NO 188
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 188

Lys Ile Glu Glu Tyr Thr Glu
 1               5

<210> SEQ ID NO 189
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 189

Lys Val Ile Glu Glu Tyr Thr Glu
 1               5

<210> SEQ ID NO 190
<211> LENGTH: 7
<212> TYPE: PRT

```
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 190

Lys Glu Glu Tyr Thr Gly Glu
1               5

<210> SEQ ID NO 191
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 191

Lys Ile Glu Glu Tyr Thr Gly Glu
1               5

<210> SEQ ID NO 192
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 192

Lys Val Ile Glu Glu Tyr Thr Gly Glu
1               5

<210> SEQ ID NO 193
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 193

Lys Phe Val Ile Glu Glu Tyr Glu
1               5

<210> SEQ ID NO 194
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 194

Lys Phe Val Ile Glu Glu Tyr Thr Glu
1               5

<210> SEQ ID NO 195
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
```

-continued into a modulating agent.

<400> SEQUENCE: 195

Lys Phe Val Ile Glu Glu Tyr Thr Gly Glu
 1               5                  10

<210> SEQ ID NO 196
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 196

Lys Phe Phe Val Ile Glu Glu Tyr Glu
 1               5

<210> SEQ ID NO 197
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 197

Lys Phe Phe Val Ile Glu Glu Tyr Thr Glu
 1               5                  10

<210> SEQ ID NO 198
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 198

Lys Phe Phe Val Ile Glu Glu Tyr Thr Gly Glu
 1               5                  10

<210> SEQ ID NO 199
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 199

Val Ile Glu Glu Tyr
 1               5

<210> SEQ ID NO 200
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 200

```
Ile Glu Glu Tyr Thr
1               5
```

<210> SEQ ID NO 201
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 201

```
Val Ile Glu Glu Tyr Thr
1               5
```

<210> SEQ ID NO 202
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 202

```
Glu Glu Tyr Thr Gly
1               5
```

<210> SEQ ID NO 203
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 203

```
Ile Glu Glu Tyr Thr Gly
1               5
```

<210> SEQ ID NO 204
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 204

```
Val Ile Glu Glu Tyr Thr Gly
1               5
```

<210> SEQ ID NO 205
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 205

```
Phe Val Ile Glu Glu Tyr
1               5
```

```
<210> SEQ ID NO 206
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 206

Phe Val Ile Glu Glu Tyr Thr
 1               5

<210> SEQ ID NO 207
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 207

Phe Val Ile Glu Glu Tyr Thr Gly
 1               5

<210> SEQ ID NO 208
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 208

Phe Phe Val Ile Glu Glu Tyr
 1               5

<210> SEQ ID NO 209
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 209

Phe Phe Val Ile Glu Glu Tyr Thr
 1               5

<210> SEQ ID NO 210
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 210

Phe Phe Val Ile Glu Glu Tyr Thr Gly
 1               5

<210> SEQ ID NO 211
<211> LENGTH: 5
<212> TYPE: PRT
<213> ORGANISM: Artificial Sequence
```

```
<220> FEATURE:
<223> OTHER INFORMATION: Cyclic peptide that may be used as a modulating
      agent without modification or may be incorporated
      into a modulating agent.

<400> SEQUENCE: 211

Cys Glu Ala Gln Cys
1               5

<210> SEQ ID NO 212
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 212

Cys Val Glu Ala Gln Cys
1               5

<210> SEQ ID NO 213
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 213

Cys Glu Ala Gln Thr Cys
1               5

<210> SEQ ID NO 214
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 214

Cys Ser Val Glu Ala Gln Cys
1               5

<210> SEQ ID NO 215
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 215

Cys Val Glu Ala Gln Thr Cys
1               5

<210> SEQ ID NO 216
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
```

```
<400> SEQUENCE: 216

Cys Ser Val Glu Ala Gln Thr Cys
1               5

<210> SEQ ID NO 217
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 217

Cys Glu Ala Gln Thr Gly Cys
1               5

<210> SEQ ID NO 218
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 218

Cys Val Glu Ala Gln Thr Gly Cys
1               5

<210> SEQ ID NO 219
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 219

Cys Ser Val Glu Ala Gln Thr Gly Cys
1               5

<210> SEQ ID NO 220
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 220

Cys Phe Ser Val Glu Ala Gln Cys
1               5

<210> SEQ ID NO 221
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 221

Cys Phe Ser Val Glu Ala Gln Thr Cys
```

```
<210> SEQ ID NO 222
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 222

Cys Phe Ser Val Glu Ala Gln Thr Gly Cys
1               5                   10

<210> SEQ ID NO 223
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 223

Cys Tyr Phe Ser Val Glu Ala Gln Cys
1               5

<210> SEQ ID NO 224
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 224

Cys Tyr Phe Ser Val Glu Ala Gln Thr Cys
1               5                   10

<210> SEQ ID NO 225
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 225

Cys Tyr Phe Ser Val Glu Ala Gln Thr Gly Cys
1               5                   10

<210> SEQ ID NO 226
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 226

Lys Glu Ala Gln Asp
1               5

<210> SEQ ID NO 227
```

```
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 227

Lys Val Glu Ala Gln Asp
 1               5

<210> SEQ ID NO 228
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 228

Lys Glu Ala Gln Thr Asp
 1               5

<210> SEQ ID NO 229
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 229

Lys Ser Val Glu Ala Gln Asp
 1               5

<210> SEQ ID NO 230
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 230

Lys Val Glu Ala Gln Thr Asp
 1               5

<210> SEQ ID NO 231
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 231

Lys Ser Val Glu Ala Gln Thr Asp
 1               5

<210> SEQ ID NO 232
<211> LENGTH: 7
<212> TYPE: PRT
<213> ORGANISM: Artificial Sequence
<220> FEATURE:
```

```
<223> OTHER INFORMATION: Cyclic peptide that may be used as a modulating
      agent without modification or may be incorporated
      into a modulating agent.

<400> SEQUENCE: 232

Lys Glu Ala Gln Thr Gly Asp
1               5

<210> SEQ ID NO 233
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 233

Lys Val Glu Ala Gln Thr Gly Asp
1               5

<210> SEQ ID NO 234
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 234

Lys Ser Val Glu Ala Gln Thr Gly Asp
1               5

<210> SEQ ID NO 235
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 235

Lys Phe Ser Val Glu Ala Gln Asp
1               5

<210> SEQ ID NO 236
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 236

Lys Phe Ser Val Glu Ala Gln Thr Asp
1               5

<210> SEQ ID NO 237
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
```

-continued

```
<400> SEQUENCE: 237

Lys Phe Ser Val Glu Ala Gln Thr Gly Asp
1               5                   10

<210> SEQ ID NO 238
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 238

Lys Tyr Phe Ser Val Glu Ala Gln Asp
1               5

<210> SEQ ID NO 239
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 239

Lys Tyr Phe Ser Val Glu Ala Gln Thr Asp
1               5                   10

<210> SEQ ID NO 240
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 240

Lys Tyr Phe Ser Val Glu Ala Gln Thr Gly Asp
1               5                   10

<210> SEQ ID NO 241
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 241

Glu Glu Ala Gln Lys
1               5

<210> SEQ ID NO 242
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 242

Glu Val Glu Ala Gln Lys
1               5
```

```
<210> SEQ ID NO 243
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 243

Glu Glu Ala Gln Thr Lys
 1               5

<210> SEQ ID NO 244
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 244

Glu Ser Val Glu Ala Gln Lys
 1               5

<210> SEQ ID NO 245
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 245

Glu Val Glu Ala Gln Thr Lys
 1               5

<210> SEQ ID NO 246
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 246

Glu Ser Val Glu Ala Gln Thr Lys
 1               5

<210> SEQ ID NO 247
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 247

Glu Glu Ala Gln Thr Gly Lys
 1               5

<210> SEQ ID NO 248
<211> LENGTH: 8
```

```
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 248

Glu Val Glu Ala Gln Thr Gly Lys
 1               5

<210> SEQ ID NO 249
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 249

Glu Ser Val Glu Ala Gln Thr Gly Lys
 1               5

<210> SEQ ID NO 250
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 250

Glu Phe Ser Val Glu Ala Gln Lys
 1               5

<210> SEQ ID NO 251
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 251

Glu Phe Ser Val Glu Ala Gln Thr Lys
 1               5

<210> SEQ ID NO 252
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 252

Glu Phe Ser Val Glu Ala Gln Thr Gly Lys
 1               5                   10

<210> SEQ ID NO 253
<211> LENGTH: 9
<212> TYPE: PRT
<213> ORGANISM: Artificial Sequence
<220> FEATURE:
<223> OTHER INFORMATION: Cyclic peptide that may be used as a modulating
```

-continued agent without modification or may be incorporated
into a modulating agent.

<400> SEQUENCE: 253

Glu Tyr Phe Ser Val Glu Ala Gln Lys
 1               5

<210> SEQ ID NO 254
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 254

Glu Tyr Phe Ser Val Glu Ala Gln Thr Lys
 1               5                  10

<210> SEQ ID NO 255
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 255

Glu Tyr Phe Ser Val Glu Ala Gln Thr Gly Lys
 1               5                  10

<210> SEQ ID NO 256
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 256

Asp Glu Ala Gln Lys
 1               5

<210> SEQ ID NO 257
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 257

Asp Val Glu Ala Gln Lys
 1               5

<210> SEQ ID NO 258
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 258

Asp Glu Ala Gln Thr Lys
 1               5

<210> SEQ ID NO 259
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 259

Asp Ser Val Glu Ala Gln Lys
 1               5

<210> SEQ ID NO 260
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 260

Asp Val Glu Ala Gln Thr Lys
 1               5

<210> SEQ ID NO 261
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 261

Asp Ser Val Glu Ala Gln Thr Lys
 1               5

<210> SEQ ID NO 262
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 262

Asp Glu Ala Gln Thr Gly Lys
 1               5

<210> SEQ ID NO 263
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 263

Asp Val Glu Ala Gln Thr Gly Lys
 1               5

```
<210> SEQ ID NO 264
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 264

Asp Ser Val Glu Ala Gln Thr Gly Lys
 1               5

<210> SEQ ID NO 265
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 265

Asp Phe Ser Val Glu Ala Gln Lys
 1               5

<210> SEQ ID NO 266
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 266

Asp Phe Ser Val Glu Ala Gln Thr Lys
 1               5

<210> SEQ ID NO 267
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 267

Asp Phe Ser Val Glu Ala Gln Thr Gly Lys
 1               5                  10

<210> SEQ ID NO 268
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 268

Asp Tyr Phe Ser Val Glu Ala Gln Lys
 1               5

<210> SEQ ID NO 269
<211> LENGTH: 10
<212> TYPE: PRT
```

```
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 269

Asp Tyr Phe Ser Val Glu Ala Gln Thr Lys
1               5                   10

<210> SEQ ID NO 270
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 270

Asp Tyr Phe Ser Val Glu Ala Gln Thr Gly Lys
1               5                   10

<210> SEQ ID NO 271
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 271

Lys Glu Ala Gln Glu
1               5

<210> SEQ ID NO 272
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 272

Lys Val Glu Ala Gln Glu
1               5

<210> SEQ ID NO 273
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 273

Lys Glu Ala Gln Thr Glu
1               5

<210> SEQ ID NO 274
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
```

```
        into a modulating agent.

<400> SEQUENCE: 274

Lys Ser Val Glu Ala Gln Glu
1               5

<210> SEQ ID NO 275
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 275

Lys Val Glu Ala Gln Thr Glu
1               5

<210> SEQ ID NO 276
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 276

Lys Ser Val Glu Ala Gln Thr Glu
1               5

<210> SEQ ID NO 277
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 277

Lys Glu Ala Gln Thr Gly Glu
1               5

<210> SEQ ID NO 278
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 278

Lys Val Glu Ala Gln Thr Gly Glu
1               5

<210> SEQ ID NO 279
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 279
```

```
Lys Ser Val Glu Ala Gln Thr Gly Glu
 1               5
```

```
<210> SEQ ID NO 280
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 280

Lys Phe Ser Val Glu Ala Gln Glu
 1               5
```

```
<210> SEQ ID NO 281
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 281

Lys Phe Ser Val Glu Ala Gln Thr Glu
 1               5
```

```
<210> SEQ ID NO 282
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 282

Lys Phe Ser Val Glu Ala Gln Thr Gly Glu
 1               5                  10
```

```
<210> SEQ ID NO 283
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 283

Lys Tyr Phe Ser Val Glu Ala Gln Glu
 1               5
```

```
<210> SEQ ID NO 284
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 284

Lys Tyr Phe Ser Val Glu Ala Gln Thr Glu
 1               5                  10
```

```
<210> SEQ ID NO 285
<211> LENGTH: 11
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 285

Lys Tyr Phe Ser Val Glu Ala Gln Thr Gly Glu
1               5                   10

<210> SEQ ID NO 286
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 286

Ser Val Glu Ala Gln
1               5

<210> SEQ ID NO 287
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 287

Val Glu Ala Gln Thr
1               5

<210> SEQ ID NO 288
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 288

Ser Val Glu Ala Gln Thr
1               5

<210> SEQ ID NO 289
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 289

Glu Ala Gln Thr Gly
1               5

<210> SEQ ID NO 290
<211> LENGTH: 6
<212> TYPE: PRT
<213> ORGANISM: Artificial Sequence
```

```
<220> FEATURE:
<223> OTHER INFORMATION: Cyclic peptide that may be used as a modulating
      agent without modification or may be incorporated
      into a modulating agent.

<400> SEQUENCE: 290

Val Glu Ala Gln Thr Gly
1               5

<210> SEQ ID NO 291
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 291

Ser Val Glu Ala Gln Thr Gly
1               5

<210> SEQ ID NO 292
<211> LENGTH: 6
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 292

Phe Ser Val Glu Ala Gln
1               5

<210> SEQ ID NO 293
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 293

Phe Ser Val Glu Ala Gln Thr
1               5

<210> SEQ ID NO 294
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 294

Phe Ser Val Glu Ala Gln Thr Gly
1               5

<210> SEQ ID NO 295
<211> LENGTH: 7
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
```

```
<400> SEQUENCE: 295

Tyr Phe Ser Val Glu Ala Gln
1               5

<210> SEQ ID NO 296
<211> LENGTH: 8
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 296

Tyr Phe Ser Val Glu Ala Gln Thr
1               5

<210> SEQ ID NO 297
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.

<400> SEQUENCE: 297

Tyr Phe Ser Val Glu Ala Gln Thr Gly
1               5

<210> SEQ ID NO 298
<211> LENGTH: 5
<212> TYPE: PRT
<213> ORGANISM: Artificial Sequence
<220> FEATURE:
<223> OTHER INFORMATION: Preferred CAR sequence for inclusion with a
      modulating agent.

<400> SEQUENCE: 298

Tyr Ile Gly Ser Arg
1               5

<210> SEQ ID NO 299
<211> LENGTH: 10
<212> TYPE: PRT
<213> ORGANISM: Artificial Sequence
<220> FEATURE:
<223> OTHER INFORMATION: Preferred CAR sequence for inclusion with a
      modulating agent.

<400> SEQUENCE: 299

Lys Tyr Ser Phe Asn Tyr Asp Gly Ser Glu
1               5                   10

<210> SEQ ID NO 300
<211> LENGTH: 17
<212> TYPE: PRT
<213> ORGANISM: Artificial Sequence
<220> FEATURE:
<223> OTHER INFORMATION: Preferred CAR sequence for inclusion with a
      modulating agent.

<400> SEQUENCE: 300

Ile Trp Lys His Lys Gly Arg Asp Val Ile Leu Lys Lys Asp Val Arg
1               5                   10                  15

Phe
```

```
<210> SEQ ID NO 301
<211> LENGTH: 4
<212> TYPE: PRT
<213> ORGANISM: Artificial Sequence
<220> FEATURE:
<223> OTHER INFORMATION: Preferred CAR sequence for inclusion with a
      modulating agent.

<400> SEQUENCE: 301

Leu Tyr His Tyr
 1

<210> SEQ ID NO 302
<211> LENGTH: 8
<212> TYPE: PRT
<213> ORGANISM: Artificial Sequence
<220> FEATURE:
<223> OTHER INFORMATION: Preferred CAR sequence for inclusion with a
      modulating agent.
<220> FEATURE:
<221> NAME/KEY: VARIANT
<222> LOCATION: 2
<223> OTHER INFORMATION: Xaa = Lys or Arg
<220> FEATURE:
<221> NAME/KEY: VARIANT
<222> LOCATION: 3,4
<223> OTHER INFORMATION: Xaa= any amino acid
<220> FEATURE:
<221> NAME/KEY: VARIANT
<222> LOCATION: 5
<223> OTHER INFORMATION: Xaa = Ser or Ala
<220> FEATURE:
<221> NAME/KEY: VARIANT
<222> LOCATION: 6
<223> OTHER INFORMATION: Xaa = Tyr or Phe
<220> FEATURE:
<221> NAME/KEY: VARIANT
<222> LOCATION: 7
<223> OTHER INFORMATION: Xaa = any amino acid

<400> SEQUENCE: 302

Trp Xaa Xaa Xaa Xaa Xaa Xaa Gly
 1               5

<210> SEQ ID NO 303
<211> LENGTH: 4
<212> TYPE: PRT
<213> ORGANISM: unknown
<220> FEATURE:
<223> OTHER INFORMATION: Representative claudin CAR sequence

<400> SEQUENCE: 303

Ile Tyr Ser Tyr
 1

<210> SEQ ID NO 304
<211> LENGTH: 4
<212> TYPE: PRT
<213> ORGANISM: unknown
<220> FEATURE:
<223> OTHER INFORMATION: Representative claudin CAR sequence

<400> SEQUENCE: 304

Thr Ser Ser Tyr
 1

<210> SEQ ID NO 305
<211> LENGTH: 4
<212> TYPE: PRT
```

```
<213> ORGANISM: unknown
<220> FEATURE:
<223> OTHER INFORMATION: Representative claudin CAR sequence

<400> SEQUENCE: 305

Val Thr Ala Phe
 1

<210> SEQ ID NO 306
<211> LENGTH: 4
<212> TYPE: PRT
<213> ORGANISM: unknown
<220> FEATURE:
<223> OTHER INFORMATION: Representative claudin CAR sequence

<400> SEQUENCE: 306

Val Ser Ala Phe
 1

<210> SEQ ID NO 307
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
<220> FEATURE:
<221> NAME/KEY: VARIANT
<222> LOCATION: 5
<223> OTHER INFORMATION: Xaa = Penicillamine

<400> SEQUENCE: 307

Cys Asp Asp Lys Xaa
 1               5

<210> SEQ ID NO 308
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
<220> FEATURE:
<221> NAME/KEY: VARIANT
<222> LOCATION: 2
<223> OTHER INFORMATION: Xaa = beta, beta-tetramethylene cysteine

<400> SEQUENCE: 308

Ile Xaa Val Ile Asp Asp Lys Ser Cys Glu
 1               5                  10

<210> SEQ ID NO 309
<211> LENGTH: 10
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
<220> FEATURE:
<221> NAME/KEY: VARIANT
<222> LOCATION: 2
<223> OTHER INFORMATION: Xaa = beta,beta-pentamethylene cysteine

<400> SEQUENCE: 309

Ile Xaa Val Ile Asp Asp Lys Ser Gly Cys
 1               5                  10
```

```
<210> SEQ ID NO 310
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
<220> FEATURE:
<221> NAME/KEY: VARIANT
<222> LOCATION: 1
<223> OTHER INFORMATION: Xaa = beta-mercaptopropionic acid

<400> SEQUENCE: 310

Xaa Val Ile Asp Asp Lys Ser Gly Cys
 1               5

<210> SEQ ID NO 311
<211> LENGTH: 9
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
<220> FEATURE:
<221> NAME/KEY: VARIANT
<222> LOCATION: 1
<223> OTHER INFORMATION: Xaa =
      beta,betapentamethylene-beta-mercaptopropionic
      acid

<400> SEQUENCE: 311

Xaa Val Ile Asp Asp Lys Ser Gly Cys
 1               5

<210> SEQ ID NO 312
<211> LENGTH: 5
<212> TYPE: PRT
<213> ORGANISM: Artificial Sequence
<220> FEATURE:
<223> OTHER INFORMATION: Cyclic peptide that may be used as a modulating
      agent without modification or may be incorporated
      into a modulating agent.
<220> FEATURE:
<221> NAME/KEY: MOD_RES
<222> LOCATION: 4
<223> OTHER INFORMATION: D-Ser

<400> SEQUENCE: 312

Asp Asp Lys Ser Ser
 1               5

<210> SEQ ID NO 313
<211> LENGTH: 4
<212> TYPE: PRT
<213> ORGANISM: Artificial Sequence
<220> FEATURE:
<223> OTHER INFORMATION: Cyclization may be achieved using this peptide

<400> SEQUENCE: 313

Trp Gly Gly Trp
 1

<210> SEQ ID NO 314
<211> LENGTH: 6
<212> TYPE: PRT
<213> ORGANISM: Artificial Sequence
<220> FEATURE:
<223> OTHER INFORMATION: CAR sequence administered in combination with
``` modulating agents

<400> SEQUENCE: 314

Ser His Ala Val Ser Ser
1               5

<210> SEQ ID NO 315
<211> LENGTH: 6
<212> TYPE: PRT
<213> ORGANISM: Artificial Sequence
<220> FEATURE:
<223> OTHER INFORMATION: CAR sequence administered in combination with
      modulating agents

<400> SEQUENCE: 315

Ala His Ala Val Asp Ile
1               5

<210> SEQ ID NO 316
<211> LENGTH: 19
<212> TYPE: DNA
<213> ORGANISM: Artificial Sequence
<220> FEATURE:
<223> OTHER INFORMATION: Forward OB-cadherin-specific primer

<400> SEQUENCE: 316
accagatgtc tgtatcaga                                                  19

<210> SEQ ID NO 317
<211> LENGTH: 21
<212> TYPE: DNA
<213> ORGANISM: Artificial Sequence
<220> FEATURE:
<223> OTHER INFORMATION: Reverse OB-cadherin-specific primer

<400> SEQUENCE: 317
gtctcctggt catcatctgc a                                               21

<210> SEQ ID NO 318
<211> LENGTH: 25
<212> TYPE: DNA
<213> ORGANISM: Artificial Sequence
<220> FEATURE:
<223> OTHER INFORMATION: Forward HPRT-specific primer

<400> SEQUENCE: 318
cctgctggat tacattaaag cactg                                           25

<210> SEQ ID NO 319
<211> LENGTH: 25
<212> TYPE: DNA
<213> ORGANISM: Artificial Sequence
<220> FEATURE:
<223> OTHER INFORMATION: Reverse HPRT-specific primer

<400> SEQUENCE: 319
gtcaagggca tatccaacaa caaac                                           25

<210> SEQ ID NO 320
<211> LENGTH: 106
<212> TYPE: PRT
<213> ORGANISM: Homo sapiens

<400> SEQUENCE: 320

Gly Trp Val Trp Asn Gln Phe Phe Val Ile Glu Glu Tyr Thr Gly Pro
1               5                   10                  15

```
-continued

Asp Pro Val Leu Val Gly Arg Leu His Ser Asp Ile Asp Ser Gly Asp
            20                      25                  30
Gly Asn Ile Lys Tyr Ile Leu Ser Gly Glu Gly Ala Gly Thr Ile Phe
            35                  40                  45
Val Ile Asp Asp Lys Ser Gly Asn Ile His Ala Thr Lys Thr Leu Asp
        50                  55                  60
Arg Glu Glu Arg Ala Gln Tyr Thr Leu Met Ala Gln Ala Val Asp Arg
65                      70                  75                  80
Asp Thr Asn Arg Pro Leu Glu Pro Pro Ser Glu Phe Ile Val Lys Val
                85                      90                  95
Gln Asp Ile Asn Asp Asn Pro Pro Glu Phe
                100                     105

<210> SEQ ID NO 321
<211> LENGTH: 106
<212> TYPE: PRT
<213> ORGANISM: Mus musculus

<400> SEQUENCE: 321

Gly Trp Val Trp Asn Gln Phe Phe Val Ile Glu Glu Tyr Thr Gly Pro
1               5                       10                  15
Asp Pro Val Leu Val Gly Arg Leu His Ser Asp Ile Asp Ser Gly Asp
            20                      25                  30
Gly Asn Ile Lys Tyr Ile Leu Ser Gly Glu Gly Ala Gly Thr Ile Phe
            35                  40                  45
Val Ile Asp Asp Lys Ser Gly Asn Ile His Ala Thr Lys Thr Leu Asp
        50                  55                  60
Arg Glu Glu Arg Ala Gln Tyr Thr Leu Met Ala Gln Ala Val Asp Arg
65                      70                  75                  80
Asp Thr Asn Arg Pro Leu Glu Pro Pro Ser Glu Phe Ile Val Lys Val
                85                      90                  95
Gln Asp Ile Asn Asp Asn Pro Pro Glu Phe
                100                     105

<210> SEQ ID NO 322
<211> LENGTH: 106
<212> TYPE: PRT
<213> ORGANISM: Gallus gallus

<400> SEQUENCE: 322

Gly Trp Val Trp Asn Gln Phe Phe Val Ile Glu Glu Tyr Thr Gly Pro
1               5                       10                  15
Asp Pro Val Leu Val Gly Arg Leu His Ser Asp Ile Asp Ser Gly Asp
            20                      25                  30
Gly Asn Ile Lys Tyr Ile Leu Ser Gly Glu Gly Ala Gly Ile Ile Phe
            35                  40                  45
Val Ile Asp Asp Lys Ser Gly Asn Ile His Ala Thr Lys Thr Leu Asp
        50                  55                  60
Arg Glu Glu Arg Ala Gln Tyr Thr Leu Thr Ala Gln Ala Val Asp Arg
65                      70                  75                  80
Asn Thr Asn Arg Pro Leu Glu Pro Pro Ser Glu Phe Ile Val Lys Val
                85                      90                  95
Gln Asp Ile Asn Asp Asn Pro Pro Glu Phe
                100                     105
```

COMPOUNDS AND METHODS FOR MODULATING OB-CADHERIN-MEDIATED FUNCTION

TECHNICAL FIELD

The present invention relates generally to methods for modulating OB-cadherin-mediated functions, and more particularly to the use of modulating agents derived from OB-cadherin cell adhesion recognition (CAR) sequences for inhibiting or enhancing functions mediated by OB-cadherin.

BACKGROUND OF THE INVENTION

Cadherins are a superfamily of calcium-dependent cell adhesion molecules (CAMs) (for review, see Munro et al., *In: Cell Adhesion and Invasion in Cancer Metastasis*, P. Brodt, ed., pp. 17-34, R G Landes Co., Austin Tex., 1996; Rowlands T M. et al (2000) Rev. Reprod. 5: 53-61, Nollet F. et al (2000) J. Mol. Biol. 299: 551-572). All cadherins appear to be membrane glycoproteins that generally promote cell adhesion through homophilic interactions (a cadherin on the surface of one cell binds to an identical cadherin on the surface of another cell), although cadherins also appear to be capable of forming heterotypic complexes with one another under certain circumstances and with lower affinity.

There are many different types of cadherins. The most extensively studied group of cadherins is known as the classical, or type I, cadherins. Classical cadherins have been shown to regulate epithelial, endothelial, neural and cancer cell adhesion, with different cadherins expressed on different cell types. All classical cadherins have a similar structure. Classical cadherins are composed of five extracellular domains (EC1-EC5), a single hydrophobic domain (TM) that transverses the plasma membrane (PM), and two cytoplasmic domains (CP1 and CP2). The calcium binding motifs DXNDN (SEQ ID NO:1), DXD and LDRE (SEQ ID NO:2) are interspersed throughout the extracellular domains, and each 110 amino acid region that contains such motifs is considered a cadherin repeat. The first extracellular domain (EC1) contains the cell adhesion recognition (CAR) sequence, HAV (His-Ala-Val), along with flanking sequences on either side of the CAR sequence that play a role in conferring specificity. Synthetic peptides containing the HAV sequence and antibodies directed against such peptides have been shown to inhibit classical cadherin-dependent processes (Munro et al., supra; Blaschuk et al., *J. Mol. Biol.* 211:679-82, 1990; Blaschuk et al., *Develop. Biol.* 139:227-29, 1990; Alexander et al., *J. Cell. Physiol.* 156:610-18, 1993; Makrigiannakis. et al. (1999) Am. J. Pathol. 154: 1391-1406; Wilby et al. (1999) Mol. Cell. Neurosci. 14: 66-84; Schnädelbach et al (2000) Mol. Cell. Neurosci. 15: 288-302; Williams et al. (2000) J. Biol. Chem. 275: 4007-4012; Schnädelbach et al. (2001) Mol. Cell. Neurosci. 17: 1084-1093; Erez et al. Exp. Cell Res. 294: 366-78; see also U.S. Pat. Nos. 6,031,072; 6,169,071; 6,417,325).

Cadherins that contain calcium binding motifs within extracellular domain cadherin repeats, but do not contain an HAV CAR sequence, are considered to be nonclassical cadherins. At least six groups of nonclassical cadherins have been identified as well several other cadherins that are not classified within the six groups These cadherins are also membrane glycoproteins. Type II, or atypical, cadherins include OB-cadherin (cadherin-11; see Getsios et al., *Developmental Dynamics* 211:238-247, 1998; Simonneau et al., *Cell Adhesion and Communication* 3:115-130, 1995; Okazaki et al., *J. Biological Chemistry* 269:12092-12098, 1994), cadherin-5 (VE-cadherin; see Navarro et al., *J. Cell Biology* 140:1475-1484, 1998), cadherin-6 (K-cadherin; see Shimoyama et al., *Cancer Research* 55:2206-2211, 1995; Shimazui et al., *Cancer Research* 56:3234-3237, 1996; Inoue et al., *Developmental Dynamics* 211:338-351, 1998; Getsios et al., *Developmental Dynamics* 211:238-247, 1998), cadherin-7 (see Nakagawa et al., *Development* 121:1321-1332, 1995), cadherin-8 (see Suzuki et al., *Cell Regulation* 2:261-270, 1991), cadherin-12 (Br-cadherin; see Tanihara et al., *Cell Adhesion and Communication* 2:15-26, 1994), cadherin-14 (see Shibata et al., *J. Biological Chemistry* 272:5236-5240, 1997), cadherin-15 (M-cadherin; see Shimoyama et al., *J. Biological Chemistry* 273:10011-10018, 1998), and PB-cadherin (see Sugimoto et al., *J. Biological Chemistry* 271:11548-11556, 1996). For a general review of atypical cadherins, see Redies and Takeichi, *Developmental Biology* 180:413-423, 1996; Suzuki et al., *Cell Regulation* 2:261-270, 1991; Nollet F. et al, (2000) J. Mol. Biol. 299: 551-572.

Other examples of nonclassical cadherins include LI-cadherin (see Berndorff et al., *J. Cell Biology* 125:1353-1369, 1994), T-cadherin (; see Ranscht, U.S. Pat. No. 5,585,351; Tkachuk et al., *FEBS Lett.* 421:208-212, 1998; Ranscht et al., *Neuron* 7:391-402, 1991; Sacristan et al., *J. Neuroscience Research* 34:664-680, 1993; Vestal and Ranscht, *J. Cell Biology* 119:451461, 1992; Fredette and Ranscht, *J. Neuroscience* 14:7331-7346, 1994; Ranscht and Bronner-Fraser, *Development* 111:15-22, 1991), protocadherins (; e.g., protocadherins 42, 43 and 68; see Sano et al., *EMBO J.* 12:2249-2256, 1993; GenBank Accession Number AF029343), desmocollins (e.g., desmocollins 1, 2, 3 and 4; see King et al., *Genomics* 18:185-194, 1993; Parker et al., *J. Biol. Chem.* 266:10438-10445, 1991; King et al., *J. Invest. Dermatol.* 105:314-321, 1995; Kawamura et al., *J. Biol. Chem.* 269: 26295-26302, 1994), desmogleins (e.g., desmogleins 1 and 2; see Wheeler et al., *Proc. Natl. Acad. Sci. USA* 88:4796-4800; Koch et al., *Eur. J. Cell. Biol.* 55:200-208, 1991), and cadherin-related neuronal receptors (see Kohmura et al., *Neuron* 20:1137-1151, 1998).

Most studies of nonclassical cadherins have focused on atypical or type II cadherins. The structure of these cadherins is similar to that of the type I cadherins, but they do not contain the CAR sequence, HAV. Furthermore, functions mediated by the atypical cadherins may be diverse. For example, cadherin-5 (also referred to as VE-cadherin) appears to be involved in endothelial cell adhesion and cadherin-6 (also referred to as K-cadherin) may be involved in embryonic kidney cell adhesion and is up-regulated in kidney cancer. Cadherin-15 also appears to play a role in the terminal differentiation of muscle cells.

OB-cadherin, which is also known as cadherin-11, is another atypical cadherin (Getsios et al., Developmental Dynamics 211:238-247, 1998; Okazaki et al., J. Biol. Chem. 269:12092-98, 1994; Suzuki et al., Cell Regulation 2:261-70, 1991; Munro et al., supra). This cadherin can promote cell adhesion through homophilic interactions. OB-cadherin does not contain the classical cadherin cell adhesion recognition sequence, HAV. A unique feature of OB-cadherin is the existence of two alternatively spliced isoforms: a full-length form with a cytoplasmic domain that interacts with catenins; and a truncated form that lacks most of the cytoplasmic domain (Feltes et al., Cancer Research 62:6688-6697, 2002). The truncated OB-cadherin variant is also shed from the cell surface and can be found deposited in the extracellular matrix surrounding the cells.

The acquisition of OB-cadherin expression by invasive cancer cells may confer invasive and migratory properties on such cells, thus facilitating metastatic dissemination (Pishvaian et al (1999) Cancer Res. 59: 947-952; Nieman et al (1999) J. Cell Biol. 147: 631-643). Highly migratory cancer cells also express the truncated form of OB-cadherin (Feltes et al An alternatively spliced cadherin-11 enhances human breast cancer cell invasion. Cancer Res. 2002 Nov. 15; 62(22):6688-97.). OB-cadherin levels are also high in stromal cells and osteoblasts (Shibata et al., Cancer Letters 99:147-53, 1996; Simonneau et al., Cell Adhes. Commun. 3:115-30, 1995; Matsuyoshi and Imamura, Biochem. Biophys. Res. Commun. 23:355-58, 1997; Okazaki et al., J. Biol. Chem. 269: 12092-98, 1994). High levels of OB-cadherin expression in osteoblasts and stromal cells, as well as in cancer cells, may promote adhesion of cancer cells to secondary sites i.e. may promote homing of metastases.

OB-cadherin mediates adhesion between osteoblasts and lack of OB-cadherin (e.g., in OB-cadherin null mice) causes reduced bone density (Kawaguchi et al., Journal of Bone and Mineral Research 16:1265-1271, 2001). These findings indicate that OB-cadherin is important for the activity of osteoblasts, and in this way may be important for regulating bone turnover. In the context of bone metastasis, the normal balance of osteoblast and osteoclast activity that constitutes bone turnover is subverted by the cancer cells, leading to bone destruction accompanied by cancer growth (Mundy, Nature Reviews Cancer, 2:584-593, 2002). Disruption of bone turnover is also a feature of other bone diseases such as osteoporosis, Pagets disease and the like. OB-cadherin-mediated interactions may be important for the maintenance of proper bone turnover, and may be instrumental in the promotion of bone destruction in bone disease and metastasis. In cancers derived from bone cells, OB-cadherin levels may be altered, suggesting a role for this cadherin in the progression of cancers such as osteosarcoma (Kashima et al., American Journal of Pathology 155:1549-1555, 1999). OB-cadherin-mediated cell-cell contact stimulates expression of vascular endothelial growth factor (VEGF) members (Orlandini and Oliviero, Journal of Biological Chemistry 276:6576-6581, 2001). VEGFs are a family of secreted growth factors that function as stimulators of angiogenesis and lymphangiogenesis, processes that are important for the growth of primary tumors and their metastatic spread. The VEGF family includes VEGF-A (also known as VEGF and vascular permeability factor), VEGF-B, VEGF-C, VEGF-D and other related proteins (for review see Dvorak (2002) J. Clin. Oncol. 20:4368-4380). In some invasive cancer cells, OB-cadherin is not only found at sites of cell-cell contact, but also in lamellopodia-like projections which do not interact with other cells. These observations suggest that OB-cadherin may also play a role in modulating cell-extracellular matrix interactions.

OB-cadherin is also expressed in other specific cell types. A role for OB-cadherin in neuronal function was indicated by the observation that OB-cadherin-deficient mice have modified behavioral responses (Manabe et al., Molecular and Cellular Neurosciences 15:534-546, 2000). In adipocytes, OB-cadherin is the only known expressed cadherin. OB-cadherin is therefore likely to mediate adhesion between adipocytes, and it is likely to be an important regulator of adipogenesis. Cells of the related lineages encompassing pericytes (also known as the peri-endothelial cell), vascular smooth muscle cells and myofibroblasts also express OB-cadherin. Pericytes are contractile cells which are similar to smooth muscle cells. They encircle the endothelial cells of blood vessels. Pericytes are involved in maintaining the structural integrity of blood vessels (Hanahan, Science 277:48-50, 1997; Lindahl et al., Science 277:242-245, 1997). Loss of pericytes causes blood vessels to regress. Vascular smooth muscle cells encircle larger blood vessels and regulate blood flow. Myofibroblasts are cells that play important roles in the wound healing process. OB-cadherin is also expressed by cells of the immune system such as CD4+CD8+ thymocytes (Munro et al., Cellular Immunology 169:309-312, 1996). Collectively, these and other observations underscore the importance of OB-cadherin as a target for the development of novel agents for treating human disease.

Notwithstanding these recent advances, OB-cadherin function remains poorly understood at the biological and molecular levels. Accordingly, there is a need in the art for identifying agents involved in modulating OB-cadherin-dependent functions and processes, such as cell adhesion, cell migration and cell invasion and for the development of further methods employing such sequences to modulate processes having relevance to human disease conditions, such as cancer cell adhesion, invasion and/or metastasis. The present invention fulfills these needs and further provides other related advantages.

SUMMARY OF THE INVENTION

This invention provides compositions and methods for modulating OB-cadherin-mediated functions and processes including, for example, modulating cell adhesion, modulating cancer cell adhesion, modulating cancer cell invasion, modulating cancer metastasis, modulating bone turnover and remodeling, modulating VEGF synthesis, modulating TGF-beta synthesis, and others.

Therefore, within certain aspects of the invention, modulating agents capable of modulating (i.e., inhibiting or enhancing) one or more functions mediated by an OB-cadherin are provided. Such modulating agents generally: (a) comprise a peptide sequence that is at least 50% identical to an OB-cadherin CAR sequence; and (b) modulate a function or process mediated by an OB-cadherin, such that the modulating agent: (i) detectably inhibits a function that is mediated by the OB-cadherin; or (ii) detectably enhances a function that is mediated by the OB-cadherin; and (c) contains no more than 85, and preferably no more than 50, consecutive amino acid residues present within an OB-cadherin, such as a naturally occurring OB-cadherin.

In another aspect of the invention, modulating agents are provided that comprise an OB-cadherin CAR sequence as described herein and contain 3-16 amino acid residues, wherein the OB-cadherin CAR sequence is selected from the group consisting of DDK, EEY and EAQ.

In another aspect of the invention, there are provided OB-cadherin modulating agents having the formula:

Aaa-Phe-Baa-Ile/Leu/Val-Asp/Asn/Glu-Caa-Daa-Ser/
    Thr/Asn-Gly                                    (SEQ ID NO: 3)

wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. For other modulating agents as described above, the OB-cadherin CAR sequence consists of at least three consecutive amino acid residues, and preferably at least five consecutive amino acid residues, of an OB-cadherin, wherein the consecutive amino acids are present within a region of the OB-cadherin having the formula recited above. Other modulating agents may comprise at least nine consecutive amino acid residues of an OB-cadherin, wherein the nine consecutive amino acid residues comprise a region having a formula as recited above.

Within certain specific embodiments, a modulating agent as described above is a peptide ranging in size from 3 to 50, preferably from 4 to 16, amino acid residues.

Within certain other embodiments, modulating agents of the invention comprise an OB-cadherin CAR sequence that is present within a cyclic peptide. Such cyclic peptides generally have the formula:

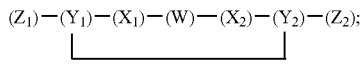

wherein W is a tripeptide selected from the group consisting of EEY, DDK and EAQ; wherein $X_1$, and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds.

Within other aspects, the present invention provides modulating agents comprising polynucleotides encoding an OB-cadherin CAR sequence as described herein, along with expression vectors comprising such polynucleotides and host cells transformed or transfected with such expression vectors.

The present invention further provides modulating agents that comprise an antibody or antigen-binding fragment thereof that specifically binds to an OB-cadherin CAR sequence provided herein and which preferably modulates an OB-cadherin-mediated function.

Within other aspects, the present invention provides modulating agents comprising a non-peptide mimetic of any one of the OB-cadherin CAR sequences provided herein.

Within certain specific embodiments, a modulating agent as provided herein may comprise: (a) one or more OB-cadherin CAR sequences selected from the group consisting of DDK, IDDK (SEQ ID NO: 4) DDKS (SEQ ID NO: 5), VIDDK (SEQ ID NO: 6), IDDKS (SEQ ID NO: 7), VIDDKS (SEQ ID NO: 8), DDKSG (SEQ ID NO: 9), IDDKSG (SEQ ID NO: 10), VIDDKSG (SEQ ID NO: 11), FVIDDK (SEQ ID NO: 12), FVIDDKS (SEQ ID NO: 13), FVIDDKSG (SEQ ID NO: 14), IFVIDDK (SEQ ID NO: 15), IFVIDDKS (SEQ ID NO: 16), IFVIDDKSG (SEQ ID NO: 17), EEY, IEEY (SEQ ID NO: 18), EEYT (SEQ ID NO: 19), VIEEY (SEQ ID NO: 20), IEEYT (SEQ ID NO: 21), VIEEYT (SEQ ID NO: 22), EEYTG (SEQ ID NO: 23), IEEYTG (SEQ ID NO: 24), VIEEYTG (SEQ ID NO: 25), FVIEEY (SEQ ID NO: 26), FVIEEYT (SEQ ID NO: 27), FVIEEYTG (SEQ ID NO: 28), FFVIEEY (SEQ ID NO: 29), FFVIEEYT (SEQ ID NO: 30), FFVIEEYTG (SEQ ID NO: 31), EAQ, VEAQ (SEQ ID NO: 32), EAQT (SEQ ID NO: 33), SVEAQ (SEQ ID NO: 34), VEAQT (SEQ ID NO: 35), SVEAQT (SEQ ID NO: 36), EAQTG (SEQ ID NO: 37), VEAQTG (SEQ ID NO: 38), SVEAQTG (SEQ ID NO: 39), FSVEAQ (SEQ ID NO: 40), FSVEAQT (SEQ ID NO: 41), FSVEAQTG (SEQ ID NO: 42), YFSVEAQ (SEQ ID NO: 43), YFSVEAQT (SEQ ID NO: 44) and YFSVEAQTG (SEQ ID NO: 45), or (b) an analogue of any of the foregoing sequences that differs in one or more substitutions, deletions, additions and/or insertions such that that ability of the analogue to modulate an OB-cadherin-mediated function is not substantially diminished. For example, the agent may comprise a linear peptide having the sequence N-Ac-IFVIDDKSG-NH$_2$ (SEQ ID NO: 17), N-Ac-FFVIEEYTG-NH$_2$ (SEQ ID NO: 31), N-Ac-YFS-VEAQTG-NH$_2$ (SEQ ID NO: 45) or N-Ac-LMAQAVDRDT-NH2 (SEQ ID NO: 46). The OB-cadherin CAR sequence may, but need not, be present within a cyclic peptide.

Any of the modulating agents of the present invention may, within certain embodiments, be linked to one or more of a drug, detectable marker, targeting agent or support material. Alternatively, or in addition, a modulating agent as described above, may further comprise one or more of: (a) a CAR sequence that is specifically recognized by an adhesion molecule other than an-OB-cadherin; and/or (b) an antibody or antigen-binding fragment thereof that specifically binds to a CAR sequence that is specifically recognized by an adhesion molecule other than an OB-cadherin. For example, a modulating agent may comprise a CAR sequence from a different non-classical cadherin, such that multiple non-classical cadherin CAR sequences are linked together within the modulating agent.

Within other aspects, the present invention provides pharmaceutical compositions comprising a modulating agent as described above in combination with a physiologically acceptable carrier. Within such compositions, the modulating agent may, but need not, be present within a sustained-release formulation. Such compositions may, within certain embodiments, further comprise a drug and/or a modulator of cell adhesion that comprises one or more of: (a) a CAR sequence that is specifically recognized by an adhesion molecule other than OB-cadherin; and/or (b) an antibody or antigen-binding fragment thereof that specifically binds to a CAR sequence that is specifically recognized by an adhesion molecule other than OB-cadherin.

The present invention further provides, within other aspects, methods for modulating one or more OB-cadherin-mediated functions using the OB-cadherin modulating agents described herein. Such methods generally comprise contacting OB-cadherin-expressing cells with a modulating agent as described herein and thereby modulating a function of OB-cadherin, such as cell adhesion.

Within other aspects, the present invention provides methods for treating, inhibiting or otherwise ameliorating the symptoms of cancer in a mammal, comprising administering to a mammal a modulating agent as described above, wherein the modulating agent inhibits one or more OB-cadherin functions, such as OB-cadherin-mediated cell adhesion. Cancer types which may be treated according to this and other related embodiments include essentially any cancer types which express OB-cadherin or which are otherwise modulated by the agents described herein, including, for example, breast cancers, ovarian cancers, leukemias (e.g., B-cell chronic lymphocyte leukemia), prostate cancers, lung cancers, lymphomas, myelomas, carcinomas, bone cancers (e.g., osteosarcomas), rhabdomyosarcomas, neuroblastomas, signet ring cancers of stomach, sarcomas, thyroid cancers, kidney cancers and other cancers derived from soft tissues and muscle. The modulating agent may be administered to the tumor locally, systemically, or by any other suitable means. Certain preferred modulating agents for use within such methods are those that inhibit cell adhesion mediated by OB-cadherin, as described herein.

Within certain preferred aspects, the present invention provides methods for treating metastatic cancer by administering to a mammal one or more modulating agent of the present invention. Essentially any cancer which expresses OB-cadherin and which has metastasized, or has the propensity to metastasize, may be treated using the inventive modulating agents including, for example, breast cancers, ovarian cancers, leukemias (e.g., B-cell chronic lymphocyte leukemia), prostate cancers, lung cancers, lymphomas, myelomas, carcinomas, bone cancers (e.g., osteosarcomas), rhabdomyosarcomas, neuroblastomas, signet ring cancers of stomach, sarcomas, thyroid cancers, kidney cancers and other cancers derived from soft tissues and muscle. Such agents may be administered to the tumor locally, systemically, or by any other suitable means. Within such methods, the modulating agent may, but need not, be present within a pharmaceutical composition as recited above.

In certain other preferred embodiments, the modulating agents described herein are used in the treatment of cancers that have either originated in the bone or metastasized to the bone. Metastatic bone cancers may be treated using modulating agents described herein, for example by targeting OB-cadherin expressed on the bone cells, and in so doing preventing the growth and/or survival of cancer cells in the bone. Cancers of the bone (e.g., osteosarcomas) and cancers that have a high propensity to metastasize to bone represent preferred targets according to this embodiment, including cancers of the breast, lung, prostate, bladder, thyroid, and kidney. In addition, myelomas and other cancers of the immune system, including lymphomas, may be treated using modulating agents of the invention.

The present invention also provides, in related embodiments, methods for modulating bone turnover and bone remodeling, comprising contacting bone cells with an OB-cadherin modulating agent.

The present invention further provides, in other aspects, methods for modulating TGF-beta synthesis, comprising contacting bone cells with an OB-cadherin modulating agent.

The present invention further provides, in other aspects, methods for modulating VEGF expression and/or synthesis, comprising contacting OB-cadherin-expressing cancer cells with an OB-cadherin modulating agent. In certain preferred embodiments of this aspect of the invention, methods are provided for modulating VEGF-A and VEGF-D expression and/or synthesis by the cancer cells.

Within certain other aspects, methods are provided for inhibiting adhesion of OB-cadherin-expressing cells in a mammal, comprising administering to a mammal a modulating agent as provided above that inhibits cell adhesion mediated by the OB-cadherin.

Within other aspects, methods are provided for inhibiting angiogenesis in a mammal, comprising administering to a mammal a modulating agent as described above, wherein the modulating agent inhibits one or more OB-cadherin-mediated functions, such as cell adhesion, cell migration or regulation of VEGF expression.

The present invention further provides, within other aspects, methods for inducing apoptosis in an OB-cadherin-expressing cell, comprising contacting a OB-cadherin-expressing cell with a modulating agent as described above, wherein the modulating agent inhibits OB-cadherin-mediated functions.

In further aspects, methods are provided for preventing or treating obesity in a mammal, comprising administering to a mammal a modulating agent as described above, wherein the modulating agent inhibits an OB-cadherin function.

Methods are further provided for stimulating blood vessel regression, comprising administering to a mammal a modulating agent as described above, wherein the modulating agent inhibits an OB-cadherin function.

Within other aspects, the present invention provides methods for enhancing adhesion of OB-cadherin-expressing cells, comprising contacting OB-cadherin-expressing cells with a modulating agent as described above, wherein the modulating agent enhances OB-cadherin-mediated cell adhesion, wherein the step of contacting is performed under conditions and for a time sufficient to detectably enhance adhesion of the cells. Within certain embodiments, modulating agents for use within such methods are linked to a support molecule or a solid support.

Within related aspects, the present invention provides methods for facilitating wound healing and/or reducing scar tissue in a mammal, comprising contacting a wound in a mammal with a modulating agent as described above, wherein the modulating agent modulates cadherin-mediated cell adhesion. Preferably, the modulating agent modulates OB-cadherin-mediated cell adhesion. Within certain embodiments, modulating agents for use within such methods are linked to a support molecules or a solid support.

Methods are also provided, within other aspects, for enhancing adhesion of foreign tissue implanted within a mammal, comprising contacting a site of implantation of foreign tissue in a mammal with a modulating agent as described above, wherein the modulating agent enhances OB-cadherin-mediated cell adhesion. Such foreign tissue may be a skin graft or organ implant. Within certain embodiments, the modulating agent is linked to a support material, support molecules or a solid support.

Within other aspects, the present invention provides methods for preventing pregnancy in a mammal, comprising administering to a mammal a modulating agent as described above, wherein the modulating agent inhibits an OB-cadherin mediated function.

The present invention further provides methods for detecting the presence of OB-cadherin-expressing cells in a sample, comprising: (a) contacting a sample with an antibody or antigen-binding fragment thereof that binds to a nonclassical CAR sequence as described above under conditions and for a time sufficient to allow formation of an antibody-cadherin complex; and (b) detecting the level of antibody-cadherin complex, and therefrom detecting the presence of OB-cadherin expressing cells in a sample. The antibody may be linked to a support material or a detectable marker such as a fluorescent marker. In certain embodiments, the step of detecting is performed using fluorescence activated cell sorting.

Kits for detecting the presence of cadherin-expressing cells in a sample are also provided. Such kits may comprise: (a) an antibody or antigen-binding fragment thereof that specifically binds to a OB-cadherin CAR sequence; and (b) a detection reagent.

Within other aspects, the present invention provides methods for identifying a compound capable of modulating a OB-cadherin-mediated function, comprising: (a) contacting an antibody or antigen-binding fragment thereof that specifically binds to a OB-cadherin CAR sequence as described above with a test compound; and (b) detecting the level of antibody or fragment that binds to the test compound, and therefrom identifying a compound capable of modulating cadherin-mediated cell adhesion.

The present invention also provides methods for modulating the immune system of a mammal, comprising administering to a mammal a modulating agent as described above, wherein the modulating agent inhibits a OB-cadherin-mediated function.

These and other aspects of the present invention will become apparent upon reference to the following detailed

BRIEF DESCRIPTION OF THE DRAWINGS

FIG. 1 provides the amino acid sequences of representative mammalian OB-cadherin EC1 domains: human OB-cadherin (SEQ ID NO: 320), mouse OB-cadherin (SEQ ID NO: 321) and chicken OB-cadherin (SEQ ID NO: 322).

FIGS. 2A-2C provide structures of representative modulating agents (SEQ ID NOS: 17, 57-62, 64-65, 71, 85, 92 and 105).

FIGS. 3A-3C are photographs showing cultures of human breast cancer cells in the presence (FIGS. 3B and 3C) and absence (FIG. 3A) of a representative linear peptide modulating agent. FIG. 3A shows the cells 24 hours after exposure to 100 µl water/1 ml culture medium (magnification 200×). FIGS. 3B and 3C show the cells 24 hours after exposure to 100 µL of a solution containing 10 mg/mL N-Ac-IFVID-DKSG-NH$_2$ (SEQ ID NO: 17) per 1 mL culture medium (magnifications of 200× and 100×, respectively). Arrows indicate rounded cells.

DETAILED DESCRIPTION OF THE INVENTION

Figure 2A:
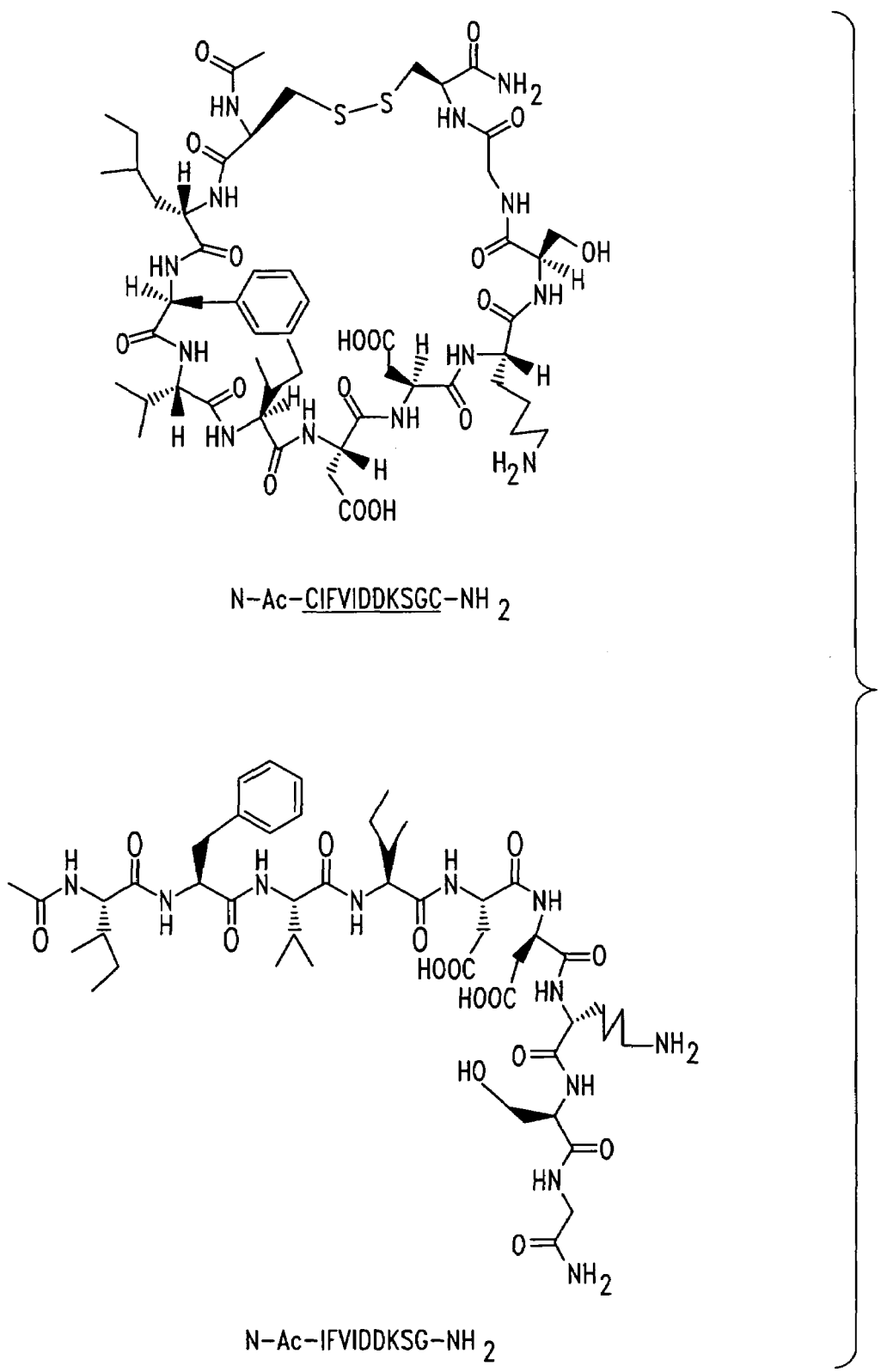

As noted above, the present invention provides methods for modulating OB-cadherin-mediated functions and/or processes, such as cell adhesion. The present invention is based, in part, on the identification of previously unknown OB-cadherin cell adhesion recognition (CAR) sequences present in naturally occurring OB-cadherins. A modulating agent may generally comprise one or more OB-cadherin CAR sequences (or analogues or mimetics thereof), with or without one or more additional CAR sequences, as described below. Peptide CAR sequences may be present within a linear or cyclic peptide. Alternatively, or in addition, a modulating agent may comprise a polynucleotide encoding a peptide comprising one or more OB-cadherin CAR sequences and/or a modulating agent may comprise a substance (such as an antibody or antigen-binding fragment thereof) that specifically binds to an OB-cadherin CAR sequence.

Other aspects of the invention are based, in part, on the discovery that OB-cadherin is expressed by certain metastatic carcinoma cells, but not by highly differentiated, poorly invasive carcinomas. Cancer metastasis may be inhibited (i.e., prevented, diminished in severity or delayed) by the administration of agents that inhibit OB-cadherin mediated cell adhesion. Such modulating agents may be peptides that correspond to an OB-cadherin CAR sequence, or may be binding agents, such as antibodies and fragments thereof, that specifically recognize an OB-cadherin CAR sequence. In general, within the methods provided herein, a modulating agent is administered to a patient in an amount sufficient to inhibit metastasis or to alleviate the symptoms of metastasis such as bone pain.

In general, to modulate an OB-cadherin-mediated function, a cell that expresses an OB-cadherin is contacted with a modulating agent either in vivo or in vitro. Within certain aspects, the methods provided herein inhibit an OB-cadherin-mediated function. Such methods include, for example, methods for treating diseases or other conditions characterized by undesirable cell adhesion, particularly diseases or other conditions associated with OB-cadherin expression, or for facilitating drug delivery to a specific tissue or tumor. Certain methods may inhibit cell adhesion (e.g., cancer cell adhesion), as well as cancer invasion and metastasis. Alternatively, a modulating agent may, such as when linked to a matrix or to another modulating agent via a linker, be used to enhance an OB-cadherin-mediated function, such as cell adhesion. Such conjugates may be used, for example, to facilitate wound healing or the adhesion of implants.

Modulating Agents

As noted above, the term "modulating agent," as used herein, refers to a molecule comprising at least one of the following components:

(a) a linear or cyclic peptide sequence that is at least 50% identical to an OB-cadherin CAR sequence (i.e., an OB-cadherin CAR sequence or an analogue thereof that retains at least 50% sequence identity);

(b) a mimetic (e.g., peptidomimetic or small molecule mimic) of an OB-cadherin CAR sequence;

(c) a substance, such as an antibody or antigen-binding fragment thereof, that specifically binds an OB-cadherin CAR sequence; and/or (d) a polynucleotide encoding a polypeptide that comprises an OB-cadherin CAR sequence or analogue thereof.

A modulating agent may consist entirely of one or more of the above elements, or may additionally comprise further peptide and/or non-peptide regions. Additional peptide regions may be derived from OB-cadherin (preferably an extracellular domain that comprises a CAR sequence) and/or may be heterologous. Within certain preferred embodiments, a modulating agent contains no more than 85 consecutive amino acid residues, and preferably no more than 50 consecutive amino acid residues, present within a naturally occurring OB-cadherin cadherin.

A modulating agent is further capable of modulating a function or process mediated by an OB-cadherin. Such activity may generally be assessed using, for example, representative assays provided herein. Certain modulating agents inhibit an interaction between OB-cadherin molecules and/or between an OB-cadherin and a different adhesion molecule. Alternatively, to enhance adhesion of OB-cadherin-expressing cells, a modulating agent may comprise an antibody or antigen-binding fragment thereof and/or multiple peptides or mimetics linked to a support material. Such modulating agents may function as a biological glue to bind OB-cadherin-expressing cells, and should result in a detectable enhancement of cell adhesion (preferably an enhancement that is at least as great as that observed for immobilized cadherin or antibody directed against the cadherin).

As used herein, the term "OB-cadherin" refers to certain cell adhesion molecules that are expressed by a human or non-human individual, and that are substantially homologous to a known OB-cadherin (also known as cadherin-11; and as discussed, for example, in Munro et al., *In: Cell Adhesion and Invasion in Cancer Metastasis*, P. Brodt, ed., pp. 17-34, RG Landes Co., Austin Tex., 1996; Getsios et al., *Developmental Dynamics* 211:238-247, 1998; Simonneau et al., *Cell Adhesion and Communication* 3:115-130, 1995; Okazaki et al., *J. Biological Chemistry* 269:12092-12098, 1994). Certain OB-cadherin molecules comprise a sequence provided in FIG. 1, but the present invention also contemplates the use of OB-cadherin from other organisms, as well as OB-cadherin variants that may have altered amino acid sequences relative to a naturally occurring OB-cadherin molecule, may contain additional amino acids or may be truncated, as described below, provided the variants retain the abililty to modulate one or more OB-cadherin functions. OB-cadherin sequences may generally be identified based upon similarity to the sequences provided herein and based upon the presence of OB-cadherin activity, using an assay provided herein.

An OB-cadherin (e.g. full-length OB-cadherin or splice variants of OB-cadherin) contains characteristic cadherin repeats, but does not contain the classical cadherin CAR sequence His-Ala-Val (HAV). As used herein, a "cadherin repeat" refers to an amino acid sequence that is approximately 110 amino acid residues in length (generally 100 to 120 residues, preferably 105 to 115 residues), comprises an extracellular domain, and contains three calcium binding motifs (DXD, XDXE and DXXDX; SEQ ID NOs: 47 and 48, respectively) in the same order and in approximately the same position. The presence of an extracellular domain may generally be determined using well known techniques, such as the presence of one or more of: a hydrophilic sequence, a region that is recognized by an antibody, a region that is cleaved by trypsin and/or a potential glycosylation site with the glycosylation motif Asn-X-Ser/Thr. The second calcium binding motif commonly has the sequence LDRE (SEQ ID NO: 2), although variants of this sequence with conservative substitutions are also observed, including MDRE (SEQ ID NO: 49), LDFE (SEQ ID NO:) 50, LDYE (SEQ ID NO: 51), IDRE (SEQ ID NO: 52), VDRE (SEQ ID NO: 53) and IDFE (SEQ ID NO: 54). Within most cadherin repeats, the third calcium binding motif has the sequence [L,I,V]-X-[L,I,V]-X-D-X-N-D-[N,H]-X-P (SEQ ID NO: 55), wherein residues indicated in brackets may be any one of the recited residues. A preferred third calcium binding motif has the sequence DXNDN (SEQ ID NO: 1), although one or both of the D residues may be replaced by an E. Homology among cadherin repeats is generally at least 20%, preferably at least 30%, as determined by the ALIGN algorithm (Myers and Miller, *CABIOS* 4:11-17, 1988). Most OB-cadherins comprise at least five cadherin repeats, along with a hydrophobic domain that transverses the plasma membrane and, optionally, one or more cytoplasmic domains.

In certain embodiments, a modulating agent is preferably capable of inhibiting OB-cadherin mediated functions such as cell adhesion, migration, invasion or regulation of growth factor expression. Such activity may generally be assessed using, for example, representative assays provided herein.

An OB-cadherin CAR sequence, as used herein, is an amino acid sequence that is present in a naturally occurring OB-cadherin and that is capable of detectably modulating an OB-cadherin-mediated function, as described herein. In other words, for example, contacting an OB-cadherin-expressing cell with a peptide comprising a CAR sequence results in a detectable change in OB-cadherin-mediated function such e.g. cell adhesion, migration, invasion or regulation of growth factor expression using at least one of the representative assays provided herein. CAR sequences are generally recognized in vivo by an OB-cadherin or other adhesion molecule (i.e., a molecule that mediates cell adhesion via a receptor on the cell surface), and are necessary for maximal heterophilic and/or homophilic interaction. CAR sequences may be of any length, but generally comprise at least three amino acid residues, preferably 4-16 amino acid residues, and more preferably 5-9 amino acid residues. A peptide modulating agent may comprise any number of amino acid residues, but certain preferred agents comprise about 3-50 residues, while other preferred agents may comprise about 4-16 residues. It will be understood that the number of amino acids present in a modulating agent may very from these illustrative ranges while still being capable of modulating OB-cadherin function and still being suitable for use in the present invention. For example, the agents may comprise 4-50 residues, 5-50 residues, 6-50 residues, etc., and all values there between.

It has been found, within the context of the present invention, that certain OB-cadherin CAR sequences share the consensus sequence:

(SEQ ID NO: 3)
Aaa-Phe-Baa-Ile/Leu/Val-Asp/Asn/Glu-Caa-Daa-Ser/Thr/Asn-Gly

Within the consensus sequence, Aaa, Baa, Caa and Daa indicate independently selected amino acid residues; "Ile/Leu/Val" indicates an amino acid that is isoleucine, leucine or valine; "Asp/Asn/Glu" indicates an amino acid that is aspartic acid, asparagine or glutamic acid; and "Ser/Thr/Asn" indicates an amino acid that is serine, threonine or asparagines. Representative OB-cadherin CAR sequences are provided within Table I. CAR sequences specifically provided herein further include portions of such representative CAR sequences, as well as longer polypeptides that comprise at least a portion of such sequences. Additional OB-cadherin CAR sequences may be identified based on sequence homology to the OB-cadherin CAR sequences provided herein, and based on the ability of a peptide comprising such a sequence to modulate OB-cadherin-mediated function within a representative assay provided herein. Within certain embodiments, a modulating agent comprises at least three consecutive residues, preferably at least five consecutive residues and more preferably at least seven consecutive residues, of an OB-cadherin CAR sequence that satisfies the above consensus sequence.

TABLE I

Representative OB-Cadherin CAR Sequences

| Cadherin | CAR Sequence |
| --- | --- |
| Human OB-cadherin EC1 | FFVIEEYTG (SEQ ID NO: 31) |
| Human OB-cadherin EC1 | IFVIDDKSG (SEQ ID NO: 17) |
| Human OB-cadherin EC2 | YFSVEAQTG (SEQ ID NO: 45) |

OB-cadherin CAR sequences are generally physically located within the cadherin molecule in or near the binding site of an adhesion molecule (i.e., within 10 amino acids, and preferably within 5 amino acids, of such a binding site). The location of a binding site may generally be determined using well known techniques, such as evaluating the ability of a portion of the OB-cadherin to bind to another OB-cadherin molecule or the ability of an OB-cadherin expressing cell to migrate, invade a matrix or regulate VEGF expression. To assess the cell adhesion function of OB-cadherin, any standard binding assay may be employed for such an evaluation. Recognition of a CAR sequence by OB-cadherin results in a measurable effect on cell adhesion. Peptides comprising a CAR sequence generally inhibit such a function.

Certain preferred OB-cadherin CAR sequences comprise 3-9 amino acid residues of a sequence provided in Table I. For example, a CAR sequence may comprise 3, 4 or 5 residues of a 9 amino acid sequence in Table I. In general, an OB-cadherin CAR sequence-comprises at least the sequence EEY, DDK or EAQ. Within certain embodiments, a CAR sequence may include at least residues 5-7 of a sequence in Table I.

Representative OB-cadherin CAR sequences comprise one or more of the peptide sequences DDK, IDDK (SEQ ID NO: 4) DDKS (SEQ ID NO: 5), VIDDK (SEQ ID NO: 6), IDDKS (SEQ ID NO: 7), VIDDKS (SEQ ID NO: 8), DDKSG (SEQ ID NO: 9), IDDKSG (SEQ ID NO: 10), VIDDKSG (SEQ ID NO: 11), FVIDDK (SEQ ID NO: 12), FVIDDKS (SEQ ID NO: 13), FVIDDKSG (SEQ ID NO: 14), IFVIDDK (SEQ ID NO: 15), IFVIDDKS (SEQ ID NO: 16), IFVIDDKSG (SEQ ID NO: 17), EEY, IEEY (SEQ ID NO: 18), EEYT (SEQ ID NO: 19), VIEEY (SEQ ID NO: 20), IEEYT (SEQ ID NO: 21), VIEEYT (SEQ ID NO: 22), EEYTG (SEQ ID NO: 23), IEEYTG (SEQ ID NO: 24), VIEEYTG (SEQ ID NO: 25), FVIEEY (SEQ ID NO: 26), FVIEEYT (SEQ ID NO: 27), FVIEEYTG (SEQ ID NO: 28), FFVIEEY (SEQ ID NO: 29), FFVIEEYT (SEQ ID NO: 30), FFVIEEYTG (SEQ ID NO: 31), EAQ, VEAQ (SEQ ID NO: 32), EAQT (SEQ ID NO: 33), SVEAQ (SEQ ID NO: 34), VEAQT (SEQ ID NO: 35), SVEAQT (SEQ ID NO: 36), EAQTG (SEQ ID NO: 37), VEAQTG (SEQ ID NO: 38), SVEAQTG (SEQ ID NO: 39), FSVEAQ (SEQ ID NO: 40), FSVEAQT (SEQ ID NO: 41), FSVEAQTG (SEQ ID NO: 42), YFSVEAQ (SEQ ID NO: 43), YFSVEAQT (SEQ ID NO: 44) or YFSVEAQTG (SEQ ID NO: 45). Linear peptides having such sequences may be modified at the N- and/or C-termini, as in the peptides N-Ac-IFVIDDKSG-NH$_2$ (SEQ ID NO: 17), N-Ac-FFVIEEYTG-NH$_2$ (SEQ ID NO: 31), N-Ac-YFSVEAQTG-NH$_2$ (SEQ ID NO: 45) and N-Ac-LMAQAVDRDT-NH2 (SEQ ID NO: 46).

To enhance specificity for OB-cadherin a modulating agent may contain a greater number of consecutive residues derived from an OB-cadherin. In addition, further flanking sequences may be included to enhance specificity. Such flanking sequences may be identified based on the sequences provided in FIG. 1, for example, or based on published sequences for OB-cadherin molecules. To achieve specificity (i.e., modulation of OB-cadherin-mediated cell adhesion or other function that is enhanced relative to the modulation of a function mediated by a different cadherin), the addition of 2 to 5 flanking residues (preferably at least one residue on either side of the CAR sequence) is generally sufficient. Specificity may be evaluated using assays for the ability to modulate functions mediated by OB-cadherins, as described herein.

As noted above, modulating agents as described herein may comprise an analogue or mimetic of an OB-cadherin CAR sequence. An analogue generally retains at least 50% identity to a native OB-cadherin CAR sequence, and modulates an OB-cadherin-mediated function, such as cell adhesion as described herein. Such analogues preferably contain at least three consecutive residues of, and more preferably at least five consecutive residues of, an OB-cadherin CAR sequence. An analogue may contain any of a variety of amino acid substitutions, additions, insertions, deletions and/or modifications (e.g., side chain modifications). Preferred amino acid substitutions are conservative. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. The critical determining feature of an OB-cadherin CAR sequence analogue is the ability to modulate an OB-cadherin-mediated function, which may be evaluated using the representative assays provided herein.

A mimetic is a non-peptidyl compound that is conformationally similar to an OB-cadherin CAR sequence, such that it modulates an OB-cadherin-mediated function, such as cell adhesion. Such mimetics may be designed based on techniques that evaluate the three dimensional structure of the peptide. For example, Nuclear Magnetic Resonance spectroscopy (NMR) and computational techniques may be used to determine the conformation of an OB-cadherin CAR sequence. NMR is widely used for structural analyses of both peptidyl and non-peptidyl compounds. Nuclear Overhauser Enhancements (NOE's), coupling constants and chemical shifts depend on the conformation of a compound. NOE data provides the interproton distance between protons through space and can be used to calculate the lowest energy conformation for the OB-cadherin CAR sequence. This information can then be used to design mimetics of the preferred conformation. Linear peptides in solution exist in many conformations. By using conformational restriction techniques it is possible to fix the peptide in the active conformation. Conformational restriction can be achieved by i) introduction of an alkyl group such as a methyl which sterically restricts free bond rotation; ii) introduction of unsaturation which fixes the relative positions of the terminal and geminal substituents; and/or iii) cyclization, which fixes the relative positions of the sidechains. Mimetics may be synthesized where one or more of the amide linkages has been replaced by isosteres, substituents or groups which have the same size or volume such as —CH$_2$NH—, —CSNH—, —CH$_2$S—, —CH=CH—, —CH$_2$CH$_2$—, —CONMe- and others. These backbone amide linkages can also be part of a ring structure (e.g., lactam). Mimetics may be designed where one or more of the side chain functionalities of the OB-cadherin CAR sequence are replaced by groups that do not necessarily have the same size or volume, but have similar chemical and/or physical properties which produce similar biological responses. Other mimetics may be small molecule mimics, which may be readily identified from small molecule libraries, based on the three-dimensional structure of the CAR sequence. It should be understood that, within embodiments described below, an analogue or mimetic may be substituted for an OB-cadherin CAR sequence.

Modulating agents, or peptide portions thereof, may be linear or cyclic peptides. The term "cyclic peptide," as used herein, refers to a peptide or salt thereof that comprises (1) an intramolecular covalent bond between two non-adjacent residues and (2) at least one OB-cadherin CAR sequence or an analogue thereof. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. One or more OB-cadherin CAR sequences, or an analogue or mimetic thereof, may be incorporated into a cyclic peptide, with or without one or more other adhesion molecule binding sites. Additional adhesion molecule binding sites are described in greater detail below.

The size of a cyclic peptide ring generally ranges from 5 to about 15 residues, preferably from 5 to 10 residues. Additional residue(s) may be present on the N-terminal and/or C-terminal side of an OB-cadherin CAR sequence, and may be derived from sequences that flank an OB-cadherin CAR sequence, with or without amino acid substitutions and/or other modifications. Alternatively, additional residues present on one or both sides of the CAR sequence(s) may be unrelated to an endogenous sequence (e.g., residues that facilitate cyclization, purification or other manipulation and/or residues having a targeting or other function).

Within certain embodiments, a modulating agent may comprise a cyclic peptide that contains an OB-cadherin CAR sequence as provided, for example, in Table I (or a portion of such a CAR sequence). Certain illustrative cyclic peptides have the formula:

$$(Z_1)-(Y_1)-(X_1)-(W)-(X_2)-(Y_2)-(Z_2);$$

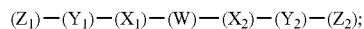

Within this formula, W is a tripeptide selected from the group consisting of EEY, DDK and EAQ; $X_1$ and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; $Y_1$ and $Y_2$ are independently selected from the group consisting of amino acid residues, and wherein a covalent bond is formed between residues $Y_1$ and $Y_2$; and $Z_1$ and $Z_2$ are optional, and if present, are independently selected from the group consisting of amino acid residues and combinations thereof in which the residues are linked by peptide bonds.

Cyclic peptides may comprise any of the above CAR sequence(s). Such cyclic peptides may be used as modulating agents without modification, or may be incorporated into a modulating agent. For example, cyclic peptides may comprise any of the above OB-cadherin CAR sequence(s). Representative cyclic peptides include CDDKC (SEQ ID NO: 57), CIDDKC (SEQ ID NO: 58), CDDKSC (SEQ ID NO: 59), CVIDDKC (SEQ ID NO: 60), CIDDKSC (SEQ ID NO: 61), CVIDDKSC (SEQ ID NO: 62), CDDKSGC (SEQ ID NO: 63), CIDDKSGC (SEQ ID NO: 64), CVIDDKSGC (SEQ ID NO: 65), CFVIDDKC (SEQ ID NO: 66), CFVIDDKSC (SEQ ID NO: 67), CFVIDDKSGC (SEQ ID NO: 68), CIFVIDDKC (SEQ ID NO: 69), CIFVIDDKSC (SEQ ID NO: 70), CIFVIDDKSGC (SEQ ID NO: 71), DDDKK (SEQ ID NO: 72), DIDDKK (SEQ ID NO: 73), DVIDDKK (SEQ ID NO: 74), DFVIDDKK (SEQ ID NO: 75), DIFVIDDKK (SEQ ID NO: 76), EDDKK (SEQ ID NO: 77), EIDDKK (SEQ ID NO: 78), EVIDDKK (SEQ ID NO: 79), EFVIDDKK (SEQ ID NO: 80), EIFVIDDKK (SEQ ID NO: 81), FVIDDK (SEQ ID NO: 82), FVIDDKS (SEQ ID NO: 83), FVIDDKSG (SEQ ID NO: 84), KDDKD (SEQ ID NO: 85), KIDDKD (SEQ ID NO: 86), KDDKSD (SEQ ID NO: 87), KVIDDKD (SEQ ID NO: 88), KIDDKSD (SEQ ID NO: 89), KVIDDKSD (SEQ ID NO: 90), KDDKSGD (SEQ ID NO: 91), KIDDKSGD (SEQ ID NO: 92), KVIDDKSGD (SEQ ID NO: 93), KFVIDDKD (SEQ ID NO: 94), KFVIDDKSD (SEQ ID NO: 95), KFVIDDKSGD (SEQ ID NO: 96), KIFVIDDKD (SEQ ID NO: 97), KIFVIDDKSD (SEQ ID NO: 98), KIFVIDDKSGD (SEQ ID NO: 99), VIDDK (SEQ ID NO: 100), IDDKS (SEQ ID NO: 101), VIDDKS (SEQ ID NO: 102), VIDDKSG (SEQ ID NO: 103), DDKSG (SEQ ID NO: 104), IDDKSG (SEQ ID NO: 105), IFVIDDK (SEQ ID NO: 106), IFVIDDKS (SEQ ID NO: 107), IFVIDDKSG (SEQ ID NO: 108), KDDKE (SEQ ID NO: 109), KIDDKE (SEQ ID NO: 110), KDDKSE (SEQ ID NO: 111), KVIDDKE (SEQ ID NO: 112), KIDDKSE (SEQ ID NO: 113), KVIDDKSE (SEQ ID NO: 114), KDDKSGE (SEQ ID NO: 115), KIDDKSGE (SEQ ID NO: 116), KVIDDKSGE (SEQ ID NO: 117), KFVIDDKE (SEQ ID NO: 118), KFVIDDKSE (SEQ ID NO: 119), KFVIDDKSGE (SEQ ID NO: 120), KIFVIDDKE (SEQ ID NO: 121), KIFVIDDKSE (SEQ ID NO: 122), KIFVIDDKSGE (SEQ ID NO: 123), CEEYC (SEQ ID NO: 124), CIEEYC (SEQ ID NO: 125), CEEYTC (SEQ ID NO: 126), CVIEEYC (SEQ ID NO: 127), CIEEYTC (SEQ ID NO: 128), CVIEEYTC (SEQ ID NO: 129), CEEYTGC (SEQ ID NO: 130), CIEEYTGC (SEQ ID NO: 131), CVIEEYTGC (SEQ ID NO: 132), CFVIEEYC (SEQ ID NO: 133), CFVIEEYTC (SEQ ID NO: 134), CFVIEEYTGC (SEQ ID NO: 135), CFFVIEEYC (SEQ ID NO: 136), CFFVIEEYTC (SEQ ID NO: 137), CFFVIEEYTGC (SEQ ID NO: 138), KEEYD (SEQ ID NO: 139), KIEEYD (SEQ ID NO: 140), KEEYTD (SEQ ID NO: 141), KVIEEYD (SEQ ID NO: 142), KIEEYTD (SEQ ID NO: 143), KVIEEYTD (SEQ ID NO: 144), KEEYTGCD (SEQ ID NO: 145), KIEEYTGD (SEQ ID NO: 146), KVIEEYTGD (SEQ ID NO: 147), KFVIEEYD (SEQ ID NO: 148), KFVIEEYTD (SEQ ID NO: 149), KFVIEEYTGD (SEQ ID NO: 150), KFFVIEEYD (SEQ ID NO: 151), KFFVIEEYTD (SEQ ID NO: 152), KFFVIEEYTGD (SEQ ID NO: 153), EEEYK (SEQ ID NO: 154), EIEEYK (SEQ ID NO: 155), EEEYTK (SEQ ID NO: 156), EVIEEYK (SEQ ID NO: 157), EIEEYTK (SEQ ID NO: 158), EVIEEYTK (SEQ ID NO: 159), EEEYTGK (SEQ ID NO: 160), EIEEYTGK (SEQ ID NO: 161), EVIEEYTGK (SEQ ID NO: 162), EFVIEEYK (SEQ ID NO: 163), EFVIEEYTK (SEQ ID NO: 164), EFVIEEYTGK (SEQ ID NO: 165), EFFVIEEYK (SEQ ID NO: 166), EFFVIEEYTK (SEQ ID NO: 167), EFFVIEEYTGK (SEQ ID NO: 168), DCEEYK (SEQ ID NO: 169), DIEEYCK (SEQ ID NO: 170), DEEYTK (SEQ ID NO: 171), DVIEEYK (SEQ ID NO:172), DIEEYTK (SEQ ID NO: 173), DVIEEYTK (SEQ ID NO: 174), DEEYTGK (SEQ ID NO: 175), DIEEYTGK (SEQ ID NO: 176), DVIEEYTGK (SEQ ID NO: 177), DFVIEEYK (SEQ ID NO: 178), DFVIEEYTK (SEQ ID NO: 179), DFVIEEYTGK (SEQ ID NO: 180), DFFVIEEYK (SEQ ID NO: 181), DFFVIEEYTK (SEQ ID NO: 182), DFFVIEEYTGK (SEQ ID NO: 183), KEEYE (SEQ ID NO: 184), KIEEYE (SEQ ID NO: 185), KEEYTE (SEQ ID NO: 186), KVIEEYE (SEQ ID NO: 187), KIEEYTE (SEQ ID NO: 188), KVIEEYTE (SEQ ID NO: 189), KEEYTGE (SEQ ID NO: 190), KIEEYTGE (SEQ ID NO: 191), KVIEEYTGE (SEQ ID NO: 192), KFVIEEYE (SEQ ID NO: 193), KFVIEEYTE (SEQ ID NO: 194), KFVIEEYTGE (SEQ ID NO: 195), KFFVIEEYE (SEQ ID NO: 196), KFFVIEEYTE (SEQ ID NO: 197), KFFVIEEYTGE (SEQ ID NO: 198), VIEEY (SEQ ID NO: 199), IEEYT (SEQ ID NO: 200), VIEEYT (SEQ ID NO: 201), EEEYTG (SEQ ID NO: 202), IEEYTG (SEQ ID NO: 203), VIEEYTG (SEQ ID NO: 204), FVIEEY (SEQ ID NO: 205), FVIEEYT (SEQ ID NO: 206), FVIEEYTG (SEQ ID NO: 207), FFVIEEY (SEQ ID NO: 208), FFVIEEYT (SEQ ID NO: 209), FFVIEEYTG (SEQ ID NO: 210), CEAQC (SEQ ID NO: 211), CVEAQC (SEQ ID NO: 212), CEAQTC (SEQ ID NO: 213), CSVEAQC (SEQ ID NO: 214), CVEAQTC (SEQ ID NO: 215), CSVEAQTC (SEQ ID NO: 216), CEAQTGC (SEQ ID NO: 217), CVEAQTGC (SEQ ID NO: 218), CSVEAQTGC (SEQ ID NO: 219), CFSVEAQC (SEQ ID NO: 220), CFSVEAQTC (SEQ ID NO: 221), CFSVEAQTGC (SEQ ID NO: 222), CYFSVEAQC (SEQ ID NO: 223), CYFSVEAQTC (SEQ ID NO: 224), CYFSVEAQTGC (SEQ ID NO: 225), KEAOD (SEQ ID NO: 226), KVEAQD (SEQ ID NO: 227), KEAQTD (SEQ ID NO: 228), KSVEAQD (SEQ ID NO: 229), KVEAQTD (SEQ ID NO: 230), KSVEAQTD (SEQ ID NO: 231), KEAQTGD (SEQ ID NO: 232), KVEAQTGD (SEQ ID NO: 233), KSVEAQTGD (SEQ ID NO: 234), KFSVEAQD (SEQ ID NO: 235), KFSVEAQTD (SEQ ID NO: 236), KFSVEAQTGD (SEQ ID NO: 237), KYFSVEAQD (SEQ ID NO: 238), KYFSVEAQTD (SEQ ID NO: 239), KYFSVEAOTGD (SEQ ID NO: 240), EEAQK (SEQ ID NO: 241), EVEAOK (SEQ ID NO: 242), EEAQTK (SEQ ID NO: 243), ESVEAQK (SEQ ID NO: 244), EVEAQTK (SEQ ID NO: 245), ESVEAQTK (SEQ ID NO: 246), EEAQTGK (SEQ ID NO: 247), EVEAQTGK (SEQ ID NO: 248), ESVEAQTGK (SEQ ID NO: 249), EFSVEAOK (SEQ ID NO: 250), EFSVEAQTK (SEQ ID NO: 251), EFSVEAQTGK (SEQ ID NO: 252), EYFSVEAOK (SEQ ID NO: 253), EYFSVEAQTK (SEQ ID NO: 254), EYFSVEAQTGK (SEQ ID NO: 255), DEAQK (SEQ ID NO: 256), DVEAQK (SEQ ID NO: 257), DEAOTK (SEQ ID NO: 258), DSVEAQK (SEQ ID NO: 259), DVEAOTK (SEQ ID NO: 260), DSVEAQTK (SEQ ID NO: 261), DEAQTGK (SEQ ID NO: 262), DVEAQTGK (SEQ ID NO: 263), DSVEAQTGK (SEQ ID NO: 264), DFSVEAQK (SEQ ID NO: 265), DFSVEAQTK (SEQ ID NO: 266), DFSVEAQTGK (SEQ ID NO: 267), DYFSVEAQK (SEQ ID NO: 268), DYFSVEAQTK (SEQ ID NO: 269), DYFSVEAQTGK (SEQ ID NO: 270), KEAOE (SEQ ID NO: 271), KVEAQE (SEQ ID NO: 272), KEAQTE (SEQ ID NO: 273), KSVEAQE (SEQ ID NO: 274), KVEAQTE (SEQ ID NO: 275), KSVEAQTE (SEQ ID NO: 276), KEAQTGE (SEQ ID NO: 277), KVEAQTGE (SEQ ID NO: 278), KSVEAQTGE (SEQ ID NO: 279), KFSVEAQE (SEQ ID NO: 280), KFSVEAQTE (SEQ ID NO: 281), KFSVEAOTGE (SEQ ID NO: 282), KYFSVEAQE (SEQ ID NO: 283), KYFSVEAQTE (SEQ ID NO: 284), KYFSVEAQTGE (SEQ ID NO: 285), SVEAQ (SEQ ID NO: 286), VEAQT (SEQ ID NO: 287), SVEAQT (SEQ ID NO: 288), EAQTG (SEQ ID NO: 289), VEAQTG (SEQ ID NO: 290), SVEAQTG (SEQ ID NO: 291), FSVEAQ (SEQ ID NO: 292), FSVEAQT (SEQ ID NO: 293), FSVEAOTG (SEQ ID NO: 294), YFSVEAQ (SEQ ID NO: 295), YFSVEAQT (SEQ ID NO: 296) and YFSVEAQTG (SEQ ID NO: 297). Within the context of the present invention, underlined sequences are cyclized using any suitable method, as described herein.

As noted above, certain preferred modulating agents comprise a peptide (containing an OB-cadherin CAR sequence or an analogue thereof) in which at least one terminal amino acid residue is modified (e.g., the N-terminal amino group is modified by, for example, acetylation or alkoxybenzylation and/or an amide or ester is formed at the C-terminus). It has been found, within the context of the present invention, that the addition of at least one such group to a linear or cyclic peptide modulating agent may improve the ability of the agent to modulate an OB-cadherin-mediated function. Certain preferred agents contain modifications at the N- and C-terminal residues, such as N-Ac-IFVIDDKSG-NH$_2$ (SEQ ID NO: 17).

The present invention further contemplates OB-cadherin CAR sequences from other organisms. Such CAR sequences may be identified based upon sequence similarity to the CAR sequences provided herein, and the ability to modulate an OB-cadherin-mediated function such as may be confirmed as described herein.

Within certain embodiments, cyclic peptides that contain small CAR sequences (e.g., three residues without significant flanking sequences) may be preferred. Such peptides may contain an N-acetyl group and a C-amide group (e.g., the 5-residue ring N-Ac-CDDKC-NH$_2$ (SEQ ID NO: 57) or N-Ac-KDDKD-NH$_2$ (SEQ ID NO: 85). Small cyclic peptides may generally be used to specifically modulate adhesion of cancer and/or other cell types by topical administration or by systemic administration, with or without linking a targeting agent to the peptide, as discussed below. Certain representative cyclic peptides comprising an OB-cadherin CAR sequence are shown in FIGS. 2A-2C.

A modulating agent may contain one OB-cadherin CAR sequence, or multiple CAR sequences that are adjacent to one another (i.e., without intervening sequences) or in close proximity (i.e., separated by peptide and/or non-peptide linkers to give a distance between the OB-cadherin CAR sequences that ranges from about 0.1 to 400 nm). A linker may be any molecule (including peptide and/or non-peptide sequences) that does not contain a CAR sequence and that can be covalently linked to at least two peptide sequences. Using a linker, CAR sequence-containing peptides and other peptide or protein sequences may be joined end-to-end (i.e., the linker may be covalently attached to the carboxyl or amino group of each peptide sequence), and/or via side chains. One linker that can be used for such purposes is (—H$_2$N(CH$_2$)$_n$CO$_2$H—), or derivatives thereof, where n ranges from 1 to 4.

Other linkers that may be used will be apparent to those of ordinary skill in the art. Peptide and non-peptide linkers may generally be incorporated into a modulating agent using any appropriate method known in the art.

Within embodiments in which enhancement of cell adhesion mediated by an OB-cadherin is desired, a modulating agent may contain multiple OB-cadherin CAR sequences, or antibodies that specifically bind to such sequences, joined by linkers as described above. For enhancers of cadherin function, the linker distance should generally be 400-10,000 nm. One linker that can be used for such purposes is (H2N(CH2)nCO2H)m, or derivatives thereof, where n ranges from 1 to 10 and m ranges from 1 to 4000. For example, if glycine (H2NCH2CO2H) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Enhancement of cell adhesion may also be achieved by attachment of multiple modulating agents to a support material, as discussed further below.

Within related embodiments, modulating agents that enhance cell adhesion preferably contain multiple CAR sequence motifs, provided such sequences are adjacent to one another in spatial orientation relative to one another that is effective for engaging two cadherin molecules, and thereby enhances cadherin-mediated adhesion and other cadherin-dependent processes. For example, dimeric forms of OB-cadherin CAR-containing peptides may be useful in certain embodiments in which enhancement of cadherin-mediated processes is desired. Dimeric forms of OB-cadherin CAR—containing cyclic peptides are also useful in the embodiments described herein. For example, cyclic peptides comprising the sequence CDDK-x-DDKC, wherein X is 4-10 amino acids in length may be particularly preferred in certain embodiments. The spacing between OB-cadherin CAR-containing motifs present within a multimer may vary while still giving rise to a desired level of agonist activity. A spacing of 1-10 amino acid residues, preferably 4-10 amino acid residues, between OB-cadherin CAR motifs in an OB-cadherin CAR multimer, for example, may be desirable in certain embodiments. Moreover, the degree of agonist activity of a given multimer may vary depending upon the concentration of the agent employed relative to the number of cadherin molecules being targeted in a given sample or subject, i.e., the level of saturation of the system being treated. Means for evaluating the agonist activity of a OB-cadherin CAR-containing multimers are provided elsewhere herein. Enhancement of cell adhesion may also be achieved by attachment of a single OB-cadherin CAR motif, multiple CAR motifs and/or multiple modulating agents to a support molecule or material, as discussed herein. Such modulating agents may additionally comprise one or more CAR sequences for one or more different adhesion molecules (including, but not limited to, other CAMs) and/or one or more antibodies or fragments thereof that bind to such sequences, to enhance cell adhesion mediated by multiple adhesion molecules.

Any OB-cadherin modulating agent or composition comprising an OB-cadherin modulating agent of the present invention may further comprise, in addition to one or more OB-cadherin CAR sequence, one or more CAR sequence derived from a different cell adhesion molecules, one or more antibodies or fragments thereof that bind to such sequences, one or more polynucleotides encoding such sequences, and the like. Linkers may, but need not, be used to separate such CAR sequence(s) and/or antibody sequence(s) from the CAR sequence(s) and/or each other. Such modulating agents may generally be used within methods in which it is desirable to simultaneously disrupt a function mediated by multiple adhesion molecules.

As used herein, an "adhesion molecule" is any molecule that mediates cell adhesion via a receptor on the cell's surface. Adhesion molecules include members of the cadherin gene superfamily including classical cadherins (preferably containing an HAV sequence), desmogleins (Dsg) and desmocollins (Dsc); integrins; members of the immunoglobulin supergene family, such as N-CAM; and other uncategorized transmembrane proteins, such as occludin, as well as extracellular matrix proteins such as laminin, fibronectin, collagens, vitronectin, entactin and tenascin.

Preferred CAR sequences for inclusion within a modulating agent include (a) Arg-Gly-Asp (RGD), which is bound by integrins (see Cardarelli et al., *J. Biol. Chem.* 267:23159-64, 1992); (b) Tyr-Ile-Gly-Ser-Arg (YIGSR; SEQ ID NO: 298), which is bound by α6β1 integrin; (c) KYSFNYDGSE (SEQ ID NO: 299), which is bound by N-CAM; (d) the N-CAM heparin sulfate-binding site IWKHKGRDVILKKDVRF (SEQ ID NO: 300); (e) the occludin CAR sequence LYHY (SEQ ID NO: 301); (f) claudin CAR sequences comprising at least four consecutive amino acids present within a claudin region that has the formula: Trp-Lys/Arg-Aaa-Baa-Ser/Ala-Tyr/Phe-Caa-Gly (SEQ ID NO:302), wherein Aaa, Baa and Caa indicate independently selected amino acid residues; Lys/Arg is an amino acid that is lysine or arginine; Ser/Ala is an amino acid that is serine or alanine; and Tyr/Phe is an amino acid that is tyrosine or phenylalanine; and (g) nonclassical cadherin CAR sequences comprising at least three consecutive amino acids present within a nonclassical cadherin region that has the formula: Aaa-Phe-Baa-Ile/Leu/Val-Asp/Asn/Glu-Caa-Daa-Ser/Thr/Asn-Gly (SEQ ID NO: 3), wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. Representative claudin CAR sequences include IYSY (SEQ ID NO:303), TSSY (SEQ ID NO:304), VTAF (SEQ ID NO:305) and VSAF (SEQ ID NO: 306). Representative nonclassical cadherin CAR sequences include the VE-cadherin (cadherin-5) CAR sequence DAE; the cadherin-6 CAR sequences EEY, NEN, ESE and DSG; the cadherin-7 CAR sequences DEN, EPK and DAN; the cadherin-8 CAR sequences EEF and NDV; the cadherin-12 CAR sequences DET and DPK; the cadherin-14 CAR sequences DDT, DPK and DAN; the cadherin-15 CAR sequences DKF and DEL; the PB-cadherin CAR sequences EEY, DEL, DPK and DAD; the protocadherin CAR sequences DLV, NRD, DPK and DPS; the dsg CAR sequences NQK, NRN and NKD; the dsc CAR sequences EKD and ERD and the cadherin-related neuronal receptor CAR sequences DPV, DAD, DSV, DSN, DSS, DEK and NEK.

Using linkers, such modulating agents may form linear or branched structures. For example, bi-functional modulating agents that comprise an OB-cadherin CAR sequence joined via a linker to separate CAR sequence(s) may be preferred for certain embodiments. As noted above, in certain embodiments, linkers preferably produce a distance between CAR sequences ranging from 0.1 to 10,000 nm, more preferably ranging from 0.1-400 nm. A separation distance between recognition sites may generally be determined according to the desired function of the modulating agent.

The total number of CAR sequences (including the OB-cadherin CAR sequence, with or without other CAR sequences derived from one or more different adhesion molecules) present within a modulating agent may range from 1 to a large number, such as 100, preferably from 1 to 10, and more preferably from 1 to 5. Peptide modulating agents comprising multiple CAR sequences typically contain from 6 (e.g., DDK-HAV) to about 1000 amino acid residues, preferably from 6 to 50 residues. When non-peptide linkers are employed, each CAR sequence of the modulating agent is present within a peptide that generally ranges in size from 3 to 50 residues in length, preferably from 4 to 25 residues, and more preferably from 5 to 15 residues.

As noted above, modulating agents may be polypeptides or salts thereof, containing only amino acid residues linked by peptide bonds, or may contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations, and the corresponding D-amino acids are designated by a lower case one letter symbol.

Modulating agents may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present within a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solution or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence-analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N-Ac and C-terminal amide groups are represented by —$NH_2$:

| | | |
|---|---|---|
| i) | N-Ac-<u>Cys-Asp-Asp-Lys-Cys</u>-NH$_2$ | (SEQ ID NO: 57) |
| ii) | N-Ac-<u>Cys-Ile-Asp-Asp-Lys-Ser-Gly-Cys</u>-NH$_2$ | (SEQ ID NO: 64) |
| iii) | N-Ac-<u>Cys-Ile-Asp-Asp-Lys-Cys</u>-NH$_2$ | (SEQ ID NO: 58) |
| iv) | N-Ac-<u>Cys-Asp-Asp-Lys-Ser-Cys</u>-NH$_2$ | (SEQ ID NO: 59) |
| v) | N-Ac-<u>Cys-Ile-Asp-Asp-Lys-Ser-Cys</u>-NH$_2$ | (SEQ ID NO: 61) |
| vi) | N-Ac-<u>Cys-Asp-Asp-Lys-Ser-Cys</u>-OH | (SEQ ID NO: 59) |
| vii) | H-<u>Cys-Ile-Asp-Asp-Lys-Ser-Cys</u>-NH$_2$ | (SEQ ID NO: 61) |
| viii) | N-Ac-<u>Cys-Asp-Asp-Lys-Pen</u>-NH$_2$ | (SEQ ID NO: 307) |
| ix) | N-Ac-<u>Cys-Phe-Val-Ile-Asp-Asp-Lys-Ser-Gly-Cys</u>-NH$_2$ | (SEQ ID NO: 68) |
| x) | N-Ac-<u>Cys-Ile-Phe-Val-Ile-Asn-Asp-Lys-Ser-Gly-Cys</u>-NH$_2$ | (SEQ ID NO: 71) |
| xi) | N-Ac-Ile-<u>Tmc-Val-Ile-Asp-Asp-Lys-Ser-Cys</u>-Gly-NH$_2$ | (SEQ ID NO: 308) |
| xii) | N-Ac-Ile-<u>Pmc-Val-Ile-Asp-Asp-Lys-Ser-Gly-Cys</u>-NH$_2$ | (SEQ ID NO: 309) |
| xiii) | <u>Mpr-Val-Ile-Asp-Asp-Lys-Ser-Gly-Cys</u>-NH$_2$ | (SEQ ID NO: 310) |
| xiv) | <u>Pmp-Val-Ile-Asp-Asp-Lys-Ser-Gly-Cys</u>-NH | (SEQ ID NO: 311) | xv)

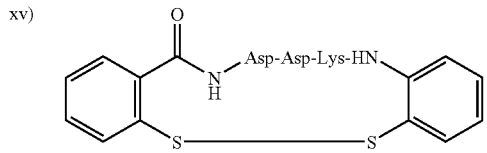

xvi)

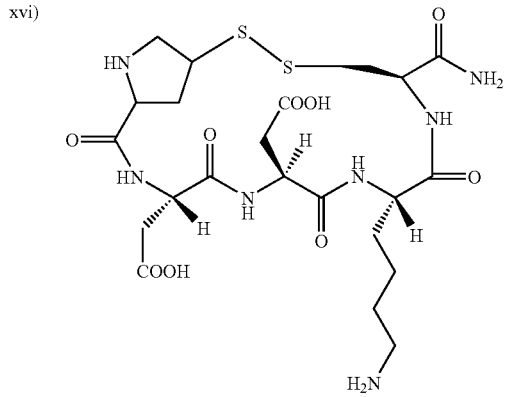

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization).

One such cyclic peptide is IDDKSG (SEQ ID NO: 105) with or without an N-terminal acetyl group and/or a C-terminal amide. Within another such embodiment, the linear peptide comprises a D-amino acid (e.g., DDKsS; SEQ ID NO: 312). Alternatively, cyclization may be accomplished by linking one terminus and a residue side chain or using two side chains, as in KDDKD (SEQ ID NO: 85) or KIDDKSGD (SEQ ID NO: 92), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction byproducts. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino)phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

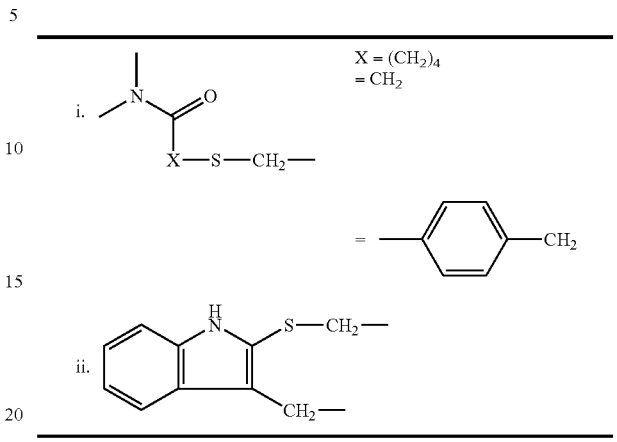

Cyclization may also be achieved using $\delta_1,\delta_{1'}$-Ditryptophan (i.e., Ac-Trp-Gly-Gly-Trp-OMe) (SEQ ID NO: 313), as shown below:

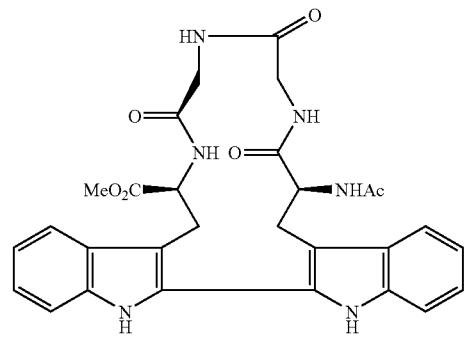

Representative structures of cyclic peptides comprising OB-cadherin CAR sequences are provided in FIGS. 2A-2C. The structures and formulas recited herein are provided solely for the purpose of illustration, and are not intended to limit the scope of the cyclic peptides described herein.

For longer modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an OB-cadherin or other adhesion molecule, or may encode a peptide comprising an OB-cadherin analogue or an antibody fragment that specifically binds to an OB-cadherin CAR sequence. Such DNA sequences may be prepared based on known cDNA or genomic sequences, or from sequences isolated by screening an appropriate library with probes designed based on the sequences of known OB-cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired modulating agent, an endogenous cadherin sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding the modulating agent.

As noted above, polynucleotides may also function as modulating agents. In general, such polynucleotides should be formulated to permit expression of a polypeptide modulating agent following administration to a mammal. Such formulations are particularly useful for therapeutic purposes, as described below. Those of ordinary skill in the art will appreciate that there are many ways to achieve expression of a polynucleotide within a mammal, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transfected cells) and/or a targeting moiety, such as a gene that encodes a ligand for a receptor on a specific target cell, to render the vector target specific. Targeting may also be accomplished using an antibody, by methods known to those of ordinary skill in the art. Other formulations for polynucleotides for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

As noted above, modulating agent may additionally, or alternatively, comprise a substance such as an antibody or antigen-binding fragment thereof, that specifically binds to an OB-cadherin CAR sequence. As used herein, a substance is said to "specifically bind" to an OB-cadherin CAR sequence (with or without flanking amino acids) if it reacts at a detectable level with a peptide containing that sequence, and does not react detectably with peptides containing a different CAR sequence or a sequence in which the order of amino acid residues in the cadherin CAR sequence and/or flanking sequence is altered. Such antibody binding properties may generally be assessed using an ELISA, which may be readily performed by those of ordinary skill in the art and is described, for example, by Newton et al., *Develop. Dynamics* 197:1-13, 1993.

Polyclonal and monoclonal antibodies may be raised against an OB-cadherin CAR sequence using conventional techniques. See, e.g., Harlow and Lane, *Antibodies: A Laboratory Manual*, Cold Spring Harbor Laboratory, 1988. In one such technique, an immunogen comprising the CAR sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the CAR sequence or antigenic portion thereof coupled to a suitable solid support.

Monoclonal antibodies specific for an OB-cadherin sequence may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation and extraction. Antibodies having the desired activity may generally be identified using immunofluorescence analyses of tissue sections, cell or other samples where the target cadherin is localized.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628-29).

Evaluation of Modulating Agent Activity

Modulating agents as described above are capable of modulating one or more OB-cadherin-mediated functions, such as cell adhesion, cell migration, cell invasion or regulation of growth factor expression. An initial screen for such activities may be performed by evaluating the ability of a modulating agent to bind to OB-cadherin using any binding assay known to those of ordinary skill in the art. For example, a Pharmacia Biosensor machine may be used, as discussed in Jonsson et al., *Biotechniques* 11:520-27, 1991. A specific example of a technology that measures the interaction of peptides with molecules can be found in Williams et al., *J. Biol. Chem.* 272, 22349-22354, 1997. Alternatively, real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule or peptide (referred to as the ligand) to the surface of a Biosensor chip, followed by binding of the interacting molecule (referred to as the analyte) to the ligand. Binding to the chip is measured in real-time in arbitrary units of resonance (RU).

By way of example, surface plasmon resonance experiments may be carried out using a BIAcore X™ Biosensor (Pharmacia Ltd., BLAcore, Uppsala, Sweden). Parallel flow cells of CM 5 sensor chips may be derivatized, using the amine coupling method, with streptavidin (200 µg/ml) in 10 mM Sodium Acetate, pH 4.0, according to the manufacturer's protocol. Approximately 2100-2600 resonance units (RU) of ligand may be immobilized, corresponding to a concentration of about 2.1-2.6 ng/mm². The chips may then coated be with OB-cadherin derivatized to biotin. Any non-specifically bound protein is removed.

To determine binding, test analytes (e.g., peptides containing the OB-cadherin CAR sequence) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, a modulating agent binds to OB-cadherin at a detectable level within such as assay. The level of binding is preferably at least that observed for the full length OB-cadherin under similar conditions.

The ability to inhibit OB-cadherin-mediated cell function may be evaluated using any of a variety of in vitro assays. It has been found, within the context of the present invention, that OB-cadherin is associated with adhesion of certain cell types, including many cancer cell types. The ability of an agent to inhibit OB-cadherin mediated function may generally be evaluated in vitro, for example by assaying the effect on adhesion between OB-cadherin-expressing cells (i.e., any type of cell that expresses OB-cadherin at a detectable level, using standard techniques such as immunocytochemical protocols (e.g., Blaschuk and Farookhi, *Dev. Biol.* 136:564-567, 1989), such as stromal, osteoblast and/or cancer cells).

In general, an agent is an inhibitor of cell adhesion if contact of the test cells with the modulating agent results in a discernible disruption of cell adhesion, when such cells are plated under standard conditions that, in the absence of modulating agent, permit cell adhesion. In the presence of modulating agent (e.g., 1 mg/mL), disruption of cell adhesion may be determined visually within 24 hours, by observing retraction of the cells from one another and the substratum.

Alternatively, cells that do not naturally express OB-cadherin may be used within such assays. Such cells may be stably transfected with a polynucleotide (e.g., a cDNA) encoding OB-cadherin, such that OB-cadherin is expressed on the surface of the cell. Expression of the cadherin may be confirmed by assessing adhesion of the transfected cells, in conjunction with immunocytochemical techniques using antibodies directed against the cadherin of interest. The stably transfected cells that aggregate, as judged by light microscopy, following transfection express sufficient levels of OB-cadherin. Preferred cells for use in such assays include L cells, which do not detectably adhere and do not express any cadherin (Nagafuchi et al., *Nature* 329:341-343, 1987). Following transfection of L cells with a cDNA encoding OB-cadherin, aggregation is observed (see Okazaki et al., *J. Biol. Chem.* 269:12092-98, 1994). Modulating agents detectably inhibit such aggregation.

Transfection of cells for use in cell adhesion assays may be performed using standard techniques and published OB-cadherin sequences. For example, a sequence of OB-cadherin may be found within references cited herein and in the GenBank database at accession number L34056 (human OB cadherin).

By way of example, an assay for evaluating a modulating agent for the ability to inhibit OB-cadherin mediated cell adhesion may employ MDA-231 human breast cancer cells. According to a representative procedure, the cells may be plated at 10-20,000 cells per 35 mm tissue culture flasks containing DMEM with 5% FCS and subcultured periodically (Sommers et al., *Cell Growth Diffn* 2:365-72, 1991).

Cells may be harvested and replated in 35 mm tissue culture flasks containing 1 mm coverslips and incubated until 50-65% confluent (24-36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 2% paraformaldehyde for 30 minutes and then washed three times with PBS. Coverslips can be mounted and viewed by phase contrast microscopy.

In the absence of modulating agent, MDA-231 cells display an epithelial-like morphology and are well attached to the substratum. MDA-231 cells that are treated with modulating agent may assume a round shape and become loosely attached to the substratum within 48 hours of treatment with 1 mg/mL of antimetastatic agent.

Certain modulating agents according to the invention may inhibit angiogenesis. The effect of a particular modulating agent on angiogenesis may generally be determined by evaluating the effect of the agent on blood vessel formation. Such a determination may generally be performed, for example, using a chick chorioallantoic membrane assay (Iruela-Arispe et al., *Molecular Biology of the Cell* 6:327-343, 1995). Briefly, a modulating agent may be embedded in a mesh composed of vitrogen at one or more concentrations (e.g., ranging from about 1 to 100 µg/mesh). The mesh(es) may then be applied to chick chorioallantoic membranes. After 24 hours, the effect of the modulating agent may be determined using computer assisted morphometric analysis. A modulating agent should inhibit angiogenesis by at least 25% at a concentration of 33 µg/mesh.

Certain modulating agents according to the invention may alter the migratory capacity of OB-cadherin-expressing cells. The effect of a particular modulating agent on migratory capacity may generally be determined by evaluating the effect of the agent on migrating cells. Such a determination may generally be performed, for example using a migration assay in which a monolayer of OB-cadherin-expressing cells is subjected to scrape wounding by drawing a fine cell scraper across the monolayer. The cells on each side of the scrape wound may respond by migrating into the wound area and this response can be observed by time-lapse photography. A modulating agent may be added to the cells at the time of scrape wounding. A modulating agent can significantly alter the number of cells that migrate into the wound area and/or the rate of migration.

Certain modulating agents according to the invention may alter the capacity of OB-cadherin-expressing cells to invade an extracellular matrix. The effect of a particular modulating agent on invasive capacity may generally be determined by evaluating the effect of the agent on invading cells. Such a determination may generally be performed, for example using a Boyden Chamber invasion assay. Briefly, OB-cadherin-expressing cells may be incubated in the presence of modulating agents in the upper chamber of a two-chambered Boyden apparatus. The lower chamber of the apparatus would contain culture medium and the two chambers are separated by a membrane coated with a layer of Matrigel. The OB-cadherin-expressing cells may invade the layer of Matrigel and enter the lower chamber. The effect of the modulating agent on the invasive capacity of the OB-cadherin-expressing cells may be determined by quantifying the cells that have passed across the Matrigel onto the lower side of the membrane after membrane fixation and staining. A modulating agent can significantly alter the number of cells that invade the layer of Matrigel and/or the rate of invasion.

Certain modulating agents according to the invention may alter the capacity of OB-cadherin-expressing cells to express growth factors e.g. members of the VEGF family. The effect of a particular modulating agent on regulation of growth factor expression may generally be determined by evaluating the effect of the agent on expression of growth factors by OB-cadherin-expressing cells. Such a determination may generally be performed, for example using an Enzyme Linked ImmunoSorbent Assay (ELISA). Briefly, a modulating agent may be incubated with OB-cadherin-expressing cells after serum-starving for 24 hours. After 16 hours treatment with the modulating agent, the medium supernatents from the cells may be analyzed using a VEGF-A ELISA kit (R&D Systems). The effect of modulating agent on VEGF-A levels may be determined by comparison with a series of known concentrations of VEGF-A ranging from 1000 pg/ml to 0 pg/ml. A modulating agent can significantly alter the levels of VEGF-A secreted by OB-cadherin-expressing cells.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support material, such as a single molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an HAV or RGD sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multi-functional linkers.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds the use of certain specific drugs within the context of the present invention is discussed below.

Modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

For certain embodiments, as discussed herein, a pharmaceutical composition may further comprise a modulator of cell adhesion that is mediated by one or more molecules other than the particular OB-cadherin. Such modulators may generally be prepared as described above, using one or more CAR sequences and/or antibodies thereto. Such compositions are particularly useful for situations in which it is desirable to inhibit cell adhesion mediated by multiple cell adhesion molecules, such as other members of the cadherin gene superfamily such as the classical cadherins (e.g., N-cadherin and E-cadherin); nonclassical cadherins (e.g., cadherin-5, cadherin-6, etc.), integrins; occludin; claudins; N-CAM and/or extracellular matrix proteins such as laminin, fibronectin, collagens, vitronectin, entactin and tenascin, or members of the immunoglobulin superfamily (CEA, PE-CAM, N-CAM, L1 or JAM).

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.002%. Fluid compositions typically contain about 10 ng/ml to 5 mg/ml, preferably from about 10 µg to 2 mg/mL modulating agent. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating a function of OB-cadherin-expressing cells such as adhesion, migration, invasion or regulation of growth factor expression. Such modulation may be performed in vitro and/or in vivo, preferably in a mammal such as a human, using any method that contacts the OB-cadherin-expressing cell with the modulating agent. As noted above, modulating agents for purposes that involve the disruption of OB-cadherin-mediated functions may comprise an OB-cadherin CAR sequence, multiple OB-cadherin CAR sequences in close proximity and/or a substance (such as an antibody or an antigen-binding fragment thereof) that recognizes an OB-cadherin CAR sequence. When it is desirable to also disrupt functions mediated by other adhesion molecules, a modulating agent may additionally comprise one or more CAR sequences bound by such adhesion molecules (and/or antibodies or fragments thereof that bind such sequences), preferably separated from each other and from the OB-cadherin CAR sequence by linkers. As noted above, such linkers may or may not comprise one or more amino acids.

For enhancing cell adhesion, as discussed above, a modulating agent may contain multiple OB-cadherin CAR sequences derived from either a particular OB-cadherin or antibodies (or fragments), preferably separated by linkers, and/or may be linked to a single molecule or to a support material as described above. When it is desirable to also enhance cell adhesion mediated by other adhesion molecules, a modulating agent may additionally comprise one or more CAR sequences bound by such adhesion molecules (and/or antibodies or fragments thereof that bind such sequences), preferably separated from each other and from the OB-cadherin CAR sequence by linker.

Certain methods involving the disruption of cell adhesion as described herein have an advantage over prior techniques in that they block cell adhesion. As described in greater detail below, modulating agents as described herein may also be used to disrupt or enhance cell adhesion in a variety of other contexts. Within each of the methods described herein, one or more modulating agents may generally be administered alone, or within a pharmaceutical composition. In each specific method described herein, as noted above, a targeting agent may be employed to increase the local concentration of modulating agent at the target site.

Within one aspect, methods are provided in which cell adhesion is diminished. In one such aspect, the present invention provides methods for reducing unwanted cellular adhesion in a mammal by administering a modulating agent as described herein. Unwanted cellular adhesion can occur, for example, between tumor cells, between tumor cells and normal cells or between normal cells as a result of surgery, injury, chemotherapy, disease, inflammation or other condition jeopardizing cell viability or function. Certain preferred modulating agents for use within such methods comprise one or more of the OB-cadherin CAR sequences provided herein. In one particularly preferred embodiment, a modulating agent is further capable of disrupting cell adhesion mediated by multiple adhesion molecules. Such an agent may comprise, in addition to one or more OB-cadherin CAR sequences, CAR sequences derived from other cell adhesion molecules, as discussed elsewhere herein, preferably separated from the OB-cadherin CAR sequence via a linker. Alternatively, separate modulators of cell adhesion mediated by other adhesion molecules may be administered in conjunction with the modulating agent(s), either within the same pharmaceutical composition or separately.

Topical administration of the modulating agent(s) is generally preferred, but other means may also be employed. Preferably, a fluid composition for topical administration (comprising, for example, physiological saline) comprises an amount of modulating agent as described above, and more preferably from 10 µg/mL to 1 mg/mL. Creams may generally be formulated as described above. Topical administration in the surgical field may be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration may be used to achieve similar results.

Within certain preferred aspects, the present invention provides methods for treating cancer and metastasis by administering to a mammal or contacting OB-cadherin-expressing cancer cells with one or more modulating agent of the present invention. Essentially any cancer type which expresses OB-cadherin and/or which has a propensity to metastasize may be treated using the inventive modulating agents including, for example, breast cancers, ovarian cancers, leukemias (e.g., B-cell chronic lymphocyte leukemia), prostate cancers, lung cancers, lymphomas, myelomas, carcinomas, bone cancers (e.g., osteosarcomas), rhabdomyosarcomas, neuroblastomas, signet ring cancers of stomach, sarcomas, thyroid cancers, kidney cancers and other cancers derived from soft tissues and muscle.

In certain other preferred embodiments, the modulating agents described herein are used in the treatment of cancers that have either originated in the bone or metastasized to the bone. For example, metastatic bone cancers may be treated using modulating agents described herein by targeting OB-cadherin expressed on the bone cells, and in so doing preventing the growth and/or survival of cancer cells in the bone. Cancers that have a high propensity to metastasize to bone represent preferred targets according to this embodiment, including cancers of the breast, lung, prostate, bladder, thyroid and kidney. In addition, myelomas exhibit similar bone destruction to that observed in many bone metastases and thus may be treated with one or more modulating agents described herein, as OB-cadherin is often expressed in bone where it resides. Other cancers of the immune system, including lymphomas, are often derived from bone marrow and may also be modulated according to the present invention.

In other embodiments, related methods are provided for modulating bone remodeling and/or bone turnover, comprising administering to a mammal and/or contacting OB-cadherin-expressing bone cells one or more OB-cadherin modulating agents described herein.

Bone mass is maintained by the balance of bone formation and bone resorption. Bone matrix consists of inorganic calcium and phosphate salts embedded on an organic backbone. The organic component is generally about 90% type I collagen fibers and 10% noncollagenous proteins and growth factors. This matrix is secreted by bone forming cells or osteoblasts. The action of osteoblasts is balanced by bone resorbing cells or osteoclasts. These cells are located on the surface of the bone and their coordinated actions constantly remodel the bone face. Regulation of bone turnover by such cells is important in the context of bone cancer and metastasis. Bone tumors and metastasis have devastating effects on bone structure because they interfere with the balance between osteoblasts and osteoclasts. Bone metastases are classified as osteolytic (overactive osteoclasts) or osteoblastic (overactive osteoblasts) although many cases have overlapping features of both types of disease. Osteolytic metastasis is the most common form.

Osteolytic metastases are characterized by a bi-directional communication between osteoclasts and tumor cells. The cancer cells produce growth factors that promote the destruction of bone by the osteoclasts. Osteoclasts respond by increasing the rate of destruction of bone matrix, which results in the release of further growth factors that are embedded within the bone matrix. These molecules stimulate the tumor cells to proliferate, and a 'vicious cycle' ensues.

Although osteoblastic lesions are not characterized by radiologically visible bone destruction, this form of the disease is also accompanied by excessive bone resorption that releases growth factors from the organic matrix. The dependence of osteoblastic disease on prior osteolysis suggests that agents that block the vicious cycle of osteolysis, such as modulating agents described herein, can be used in treatments for both types of metastasis. In addition to metastasis, diseases that affect the state of bone turnover, and are capable of being treated with one or more modulating agents described herein, include osteoporosis, Pagets disease, myeloma, androgen therapy for prostate cancer. Another therapeutic use for modulation of bone turnover is to facilitate healing of fractures or implants.

A modulating agent may be administered alone (e.g. via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. In certain embodiments, the tumor is a tumor of the breast, ovary, stomach, prostate or kidney. In general, the amount of agent administered varies depending upon the method of administration and the nature of the cancer, but may vary within the ranges identified above. The effectiveness of the cancer treatment or inhibition of metastasis may be evaluated using well known clinical observations, such as monitoring the level of serum tumor markers (e.g., CEA or PSA).

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

The present invention further provides, in other aspects, methods for modulating TGF-beta synthesis, comprising administering to a mammal and/or contacting OB-cadherin-expressing cells with, one or more OB-cadherin modulating agents described herein. TGF-beta is believed to be a key player in the signaling that occurs between bone cells to regulate bone turnover and between bone and tumor cells. Modulating agents of the present invention may be useful for modulating TGF-beta synthesis, and osteoblast activity, and may therefore be useful for treating diseases or other conditions in which such modulation is desired, such as osteoporosis, Pagets disease, myeloma, androgen therapy for prostate cancer, bone cancer, etc.

The present invention further provides, in other aspects, methods for modulating VEGF expression and/or synthesis, comprising administering to a mammal and/or contacting OB-cadherin-expressing cells with an OB-cadherin modulating agent described herein. As VEGF expression is a stimulator of angiogenesis and lymphangiogenesis, essentially any cancer or other condition where growth is promoted by lymphangiogenesis or angiogenesis may be suitable for treatment with one or more modulating agents described herein. In certain preferred embodiments of this aspect of the invention, methods are provided for modulating VEGF-A and VEGF-D expression and/or synthesis. The VEGF-D isoform is specifically involved in lymphangiogenesis, and OB-cadherin modulates VEGF-D expression when expressed by fibroblasts in vitro (Orlandini and Oliviero 2001 Journal of Biological Chemistry 276 6576-6581). In addition, as demonstrated herein, OB-cadherin-modulating agents have been shown to regulate VEGF-A expression by cancer cells. VEGFs also regulate vascular permeability. In the context of cancer, a reduction in the expression of VEGFs, for example employing one or more modulating agents described herein, may be used to inhibit angiogenesis and/or lymphangiogenesis and/or to slow the progression of tumor growth. This would also slow dissemination of tumor cells and slow progression of metastatic disease, as well as slow the growth of secondary tumors in metastatic disease. Increased vascular permeability caused by changed levels of VEGF isoforms may be used to facilitate drug delivery.

Within further aspects, the present invention provides methods for inhibiting angiogenesis (i.e., the growth of blood vessels from pre-existing blood vessels) in a mammal. Inhibition of angiogenesis may be beneficial, for example, in patients afflicted with diseases such as cancer or arthritis. Preferred modulating agents for inhibition of angiogenesis include those that modulate functions mediated by OB-cadherins. In addition, a modulating agent for use in inhibiting angiogenesis may further comprise a separate CAR sequence from a different cell adhesion molecule, as discussed above, such as the sequence RGD, which is recognized by integrins, the classical cadherin CAR sequence HAV, and/or the occludin CAR sequence LYHY (SEQ ID NO: 301), separated from the OB-cadherin CAR sequence via a linker. Alternatively, a separate modulator of classical cadherin-, integrin- or occludin-mediated cell adhesion may be administered in conjunction with the modulating agent(s), either within the same pharmaceutical composition or separately. The ability of a modulating agent to inhibit angiogenesis may be evaluated as described above.

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

In yet another related aspect, the present invention provides methods for modulating cell survival, such as methods for inducing apoptosis in a cadherin-expressing cell. In general, patients afflicted with cancer may benefit from such treatment. Modulating agents for use within such methods may modulate functions mediated by OB-cadherin and/or other classical and nonclassical cadherin(s). Such agents comprise an OB-cadherin CAR sequence, and may further comprise, for example, a CAR sequence of a different cell adhesion molecule, as discussed above, or an analogue of such a sequence. In one embodiment, the peptide portion(s) of such modulating agents comprise 6-16 amino acids, however it will be appreciated that both shorter and longer modulating agents may also be used. Preferred antibody modulating agents in this context include Fab fragments directed against OB-cadherin and/or a nonclassical or classical cadherin CAR sequence. The Fab fragments may be either incorporated into a modulating agent or within a separate modulator that is administered concurrently. Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

Within a related aspect, the present invention provides methods for treating obesity in a mammal, by using modulating agents that disrupt OB-cadherin function to inhibit adipocyte adhesion or survival. Alternatively, modulating agents that inhibit angiogenesis as described herein may be used to inhibit fat cell growth. Modulating agents as described herein may be administered alone, or in combination with other agents, which may comprise, for example, a CAR sequence from a different cell adhesion molecule, such as DAE, HAV, SHAVSS (SEQ ID NO: 314), AHAVDI (SEQ ID NO: 315), RGD or an analogue of such a sequence. Preferably the peptide portion(s) of such modulating agents comprise 6-16 amino acids. The use of Fab fragments directed against an OB-cadherin, cadherin-5 or N-cadherin CAR sequence is also preferred. A modulating agent may be administered alone (e.g., via the skin) or within a pharmaceutical composition. Injection or topical administration as described above may be preferred. In other instances, the composition may be administered systemically.

In another embodiment, methods are provided for causing the regression of blood vessels for the treatment of conditions such as cancer, psoriasis, arthritis, and age-related macular degeneration. Cancer tumors are solid masses of cells, growing out of control, which require nourishment via blood vessels. The formation of new capillaries is a prerequisite for tumor growth and the emergence of metastases. Administration of the modulating agents described herein may disrupt blood vessels and cause them to regress, thereby providing effective therapy for patients afflicted with diseases such as cancer. Certain preferred modulating agents for use within such methods comprise, in addition to an OB-cadherin CAR sequence, a separate CAR sequence from a different cell adhesion molecule, as described above, such as HAV and RGD, or an analogue of such a sequence. Preferably, the peptide portion(s) of such modulating agents comprise 6-16 amino acids. Preferred antibody modulating agents include Fab fragments directed against the OB-cadherin CAR sequence, with or without Fab fragments directed against one or more other cadherin CAR sequences. The Fab fragments may be either incorporated into a modulating agent or within a separate modulator that is administered concurrently. Administration may be topical, via injection or by other means, and the addition of a targeting agent may be beneficial, particularly when the administration is systemic. Suitable modes of administration and dosages depend upon the location and nature of the vasculature for which disruption of cell adhesion is desired but, in general, dosages may vary as described above. The effectiveness of the cancer treatment or inhibition of metastasis may be evaluated using well known clinical observations such as the level of serum markers (e.g., CEA or PSA). The addition of a targeting agent may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumor to maintain growth and microscopically by an absence of nerves at the periphery of the tumor.

In certain other aspects, the present invention provides methods for enhancing adhesion of OB-cadherin-expressing cells. Within certain embodiments, a modulating agent may be linked to a solid support, resulting in a matrix that comprises multiple modulating agents. Within one such embodiment, the support is a polymeric matrix to which modulating agents and molecules comprising other CAR sequence(s) are attached (e.g., modulating agents and molecules comprising either HAV or RGD sequences may be attached to the same matrix, preferably in an alternating pattern). Such matrices may be used in contexts in which it is desirable to enhance adhesion mediated by multiple cell adhesion molecules. Alternatively, the modulating agent itself may comprise multiple OB-cadherin CAR sequences or antibodies (or fragments thereof), separated by linkers as described above. Either way, the modulating agent(s) function as a "biological glue" to bind multiple nonclassical cadherin-expressing cells within a variety of contexts.

Within one such aspect, modulating agents comprising an OB-cadherin CAR sequence and/or multiple modulating agents linked to a single molecule or support material may be used to facilitate wound healing and/or reduce scar tissue in a mammal. The modulating agents may further comprise CAR sequences from other cell adhesion molecules, as described herein, such as cadherin-5, desmoglein and/or desmocollin CAR sequences. Additionally, other CAR sequences include HAV, SHAVSS (SEQ ID NO: 314), AHAVDI (SEQ ID NO: 315), or an analogue of such a sequence. Preferred antibody modulating agents include Fab fragments directed against either the OB-cadherin CAR sequence and may further comprise Fab fragments directed against nonclassical cadherin or E-cadherin CAR sequences. Modulating agents that are linked to a biocompatible and biodegradable matrix such as cellulose or collagen are particularly preferred. For use within such methods, a modulating agent should have a free amino or hydroxyl group. The modulating agents are generally administered topically to the wound, where they may facilitate closure of the wound and may augment, or even replace, stitches. Similarly, administration of matrix-linked modulating agents may facilitate cell adhesion in skin grafting and prosthetic implants, and may prolong the duration and usefulness of collagen injection. In general, the amount of matrix-linked modulating agent administered to a wound, graft or implant site varies with the severity of the wound and/or the nature of the wound, graft, or implant, but may vary as discussed above. Multi-functional modulating agents comprising an OB-cadherin CAR sequence and further comprising one ore more CAR sequences from another cell adhesion molecules, as described herein, such as a nonclassical cadherin CAR sequence, a classical cadherin CAR sequence (HAV), and/or the CAR sequence bound by certain integrins (RGD) may also be used as potent stimulators of wound healing and/or to reduce scar tissue. Alternatively, one or more separate modulators of classical cadherin- or integrin-mediated cell adhesion may be administered in conjunction with the modulating agent(s), either within the same pharmaceutical composition or separately.

Within another aspect, one or more modulating agents may be linked to the interior surface of a tissue culture plate or other cell culture support, such as for use in a bioreactor. Such linkage may be performed by any suitable technique, as described above. Modulating agents linked in this fashion may generally be used to immobilize cadherin-expressing cells. For example, dishes or plates coated with one or more modulating agents may be used to immobilize cadherin-expressing cells within a variety of assays and screens. Within bioreactors (i.e., systems for large scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of modulating agent(s) may also be used to facilitate the production of specific proteins.

Modulating agents as described herein may be used within a variety of bioreactor configurations. In general, a bioreactor is designed with an interior surface area sufficient to support large numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics; glass and silica.

Within further aspects, the present invention provides methods and kits for preventing pregnancy in a mammal. In general, disruption of OB-cadherin function prevents the adhesion of trophoblasts and their subsequent fusion to form syncitiotrophoblasts, and may also prevent angiogenesis. In one embodiment, one or more modulating agents may be incorporated into any of a variety of well known contraceptive devices, such as sponges suitable for intravaginal insertion (see, e.g., U.S. Pat. No. 5,417,224) or capsules for subdermal implantation. Other modes of administration are possible, however, including transdermal administration, for modulating agents linked to an appropriate targeting agent. Preferred modulating agents for use within such methods include those comprising an OB-cadherin CAR sequence, as described herein, and may further comprise, for example, one or more CAR sequences from a different cell adhesion molecule, as described herein, such as a cadherin-5 CAR sequence, or analogue or mimetic thereof. In addition, other illustrative modulating agents may comprise additional CAR sequences, such as HAV and/or RGD. As noted above, such additional sequences may be separated from the nonclassical CAR sequence via a linker. Alternatively, a separate modulator of classical cadherin- and/or integrin-mediated cell adhesion may be administered in conjunction with the OB-cadherin modulating agent(s), either within the same pharmaceutical composition or separately.

Suitable methods for incorporation into a contraceptive device depend upon the type of device and are well known in the art. Such devices facilitate administration of the modulating agent(s) to the uterine region and may provide a sustained release of the modulating agent(s). In general, modulating agent(s) may be administered via such a contraceptive device at a dosage ranging from 0.1 to 50 mg/kg, although appropriate dosages may be determined by monitoring hCG levels in the urine. hCG is produced by the placenta, and levels of this hormone rise in the urine of pregnant women. The urine hCG levels can be assessed by radio-immunoassay using well known techniques. Kits for preventing pregnancy generally comprise a contraceptive device impregnated with one or more modulating agents.

Alternatively, a sustained release formulation of one or more modulating agents may be implanted, typically subdermally, in a mammal for the prevention of pregnancy. Such implantation may be performed using well known techniques. Preferably, the implanted formulation provides a dosage as described above, although the minimum effective dosage may be determined by those of ordinary skill in the art using, for example, an evaluation of hCG levels in the urine of women.

Other aspects of the present invention provide methods that employ antibodies raised against OB-cadherin CAR sequences for diagnostic and assay purposes. Assays typically involve using an antibody to detect the presence or absence of OB-cadherin (free or on the surface of a cell), or proteolytic fragments containing one or more EC domains in a suitable biological sample, such as tumor or normal tissue biopsies, blood, lymph node, serum or urine samples, or other tissue, homogenate, or extract thereof obtained from a patient.

There are a variety of assay formats known to those of ordinary skill in the art for using an antibody to detect a target molecule in a sample. See, e.g., Harlow and Lane, Antibodies: A Laboratory Manual, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target OB-cadherin, or a proteolytic fragment containing an extracellular domain and encompassing a CAR sequence, and remove it from the remainder of the sample. The bound cadherin may then be detected using a second antibody or reagent that contains a reporter group. Alternatively, a competitive assay may be utilized, in which a cadherin is labeled with a reporter group and allowed to bind to the immobilized antibody after incubation of the antibody with the sample. The extent to which components of the sample inhibit the binding of the labeled cadherin to the antibody is indicative of the reactivity of the sample with the immobilized antibody, and as a result, indicative of the level of the cadherin in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of an OB-cadherin in a sample is a two-antibody sandwich assay. This assay may be performed by first contacting an antibody that has been immobilized on a solid support, commonly the well of a microtiter plate, with the biological sample, such that the OB-cadherin within the sample is allowed to bind to the immobilized antibody (a 30 minute incubation time at room temperature is generally sufficient). Unbound sample is then removed from the immobilized OB-cadherin-antibody complexes and a second antibody (containing a reporter group such as an enzyme, dye, radionuclide, luminescent group, fluorescent group or biotin) capable of binding to a different site on the OB-cadherin is added. The amount of second antibody that remains bound to the solid support is then determined using a method appropriate for the specific reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of cadherin in a sample, using well-known techniques.

The present invention also provides kits for use in such immunoassays. Such kits generally comprise one or more antibodies, as described above. In addition, one or more additional compartments or containers of a kit generally enclose elements, such as reagents, buffers and/or wash solutions, to be used in the immunoassay.

Within further aspects, modulating agents or antibodies (or fragments thereof) may be used to facilitate cell identification and sorting in vitro or imaging in vivo, permitting the selection of cells expressing OB-cadherin (or different OB-cadherin levels). Preferably, the modulating agent(s) or antibodies for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulating agent linked to a fluorescent marker, such as fluorescein, is contacted with the cells, which are then analyzed by fluorescence activated cell sorting (FACS).

Antibodies or fragments thereof may also be used within screens of combinatorial or other nonpeptide-based libraries to identify other compounds capable of modulating OB-cadherin-mediated cell adhesion. Such screens may generally be performed using an ELISA or other method well known to those of ordinary skill in the art that detect compounds with a shape and structure similar to that of the modulating agent. In general, such screens may involve contacting an expression library producing test compounds with an antibody, and detecting the level of antibody bound to the candidate compounds. Compounds for which the antibody has a higher affinity may be further characterized as described herein, to evaluate the ability to modulate OB-cadherin-mediated cell adhesion.

Within other aspects, modulating agents of the invention may be used to remove metastatic cells from a biological sample, such as blood, bone marrow or a fraction thereof. Such removal may be achieved by contacting a biological sample with an antimetastatic agent under conditions and for a time sufficient to permit OB-cadherin expressing cells to bind to the antimetastatic agent. The OB-cadherin expressing cells that have bound to the antimetastatic agent are then separated from the remainder of the sample. To facilitate this removal, an antimetastatic agent may be linked to a solid support. Preferably, the contact results in the reduction of OB-cadherin expressing cells in the sample to less than 1%, preferably less than 0.1%, of the level prior to contact with the antimetastatic agent. The extent to which such cells have been removed may be readily determined by standard methods such as, for example, qualitative and quantitative PCR analysis, immunohistochemistry and FACS analysis. Following removal of metastatic cells, the biological sample may be returned to the patient using standard techniques.

Within other aspects, the present invention provides compositions and methods for diagnosing a cancer, particularly a cancer that expresses OB-cadherin, such as breast, ovarian and prostate cancer, as well as leukemia. Certain methods provided herein employ binding agents, such as antibodies and fragments thereof, that specifically recognize OB-cadherin. Other methods employ one or more polynucleotides capable of hybridizing to a polynucleotide encoding OB-cadherin.

Within certain aspects, the present invention provides methods for determining the presence or absence of a cancer in a patient, comprising the steps of: (a) contacting a biological sample obtained from a patient with a binding agent that specifically binds to OB-cadherin; and (b) detecting in the sample an amount of polypeptide that binds to the binding agent, relative to a predetermined cut-off value, and therefrom determining the presence or absence of a cancer in the patient.

Within further aspects, methods are provided for monitoring the progression of a cancer in a patient, comprising the steps of: (a) contacting a biological sample obtained from a patient at a first point in time with a binding agent that specifically binds to OB-cadherin; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) to the amount detected in step (b) and therefrom monitoring the progression of the cancer in the patient.

Within other aspects, methods are provided for evaluating the metastatic potential of a cancer in a patient, comprising the steps of: (a) contacting a biological sample obtained from a patient afflicted with cancer with a binding agent that specifically binds to OB-cadherin; and (b) detecting in the sample an amount of polypeptide that binds to the binding agent, relative to a predetermined cut-off value, and therefrom evaluating the metastatic potential of the cancer in the patient.

Kits for determining the presence or absence of a cancer in a patient are also provided. Such kits may comprise: (a) an antibody or antigen-binding fragment thereof that specifically binds to an OB-cadherin CAR sequence; and (b) a detection reagent.

The present invention further provides methods for determining the presence or absence of a metastatic cancer in a patient, comprising the steps of: (a) contacting a biological sample obtained from a patient with an oligonucleotide that hybridizes to a polynucleotide encoding OB-cadherin; and (b) detecting in the sample a level of a polynucleotide that hybridizes to the oligonucleotide, relative to a predetermined cut-off value, and therefrom determining the presence or absence of a metastatic cancer in the patient. Within certain embodiments, the amount of mRNA is detected via polymerase chain reaction using, for example, at least one oligonucleotide primer that hybridizes to a polynucleotide that encodes OB-cadherin, or a complement of such a polynucleotide. Within other embodiments, the amount of mRNA is detected using a hybridization technique, employing an oligonucleotide probe that hybridizes to a polynucleotide that encodes OB-cadherin, or a complement of such a polynucleotide. In a preferred embodiment, at least one of the oligonucleotide primers comprises at least about 10 contiguous nucleotides of a DNA molecule encoding OB-cadherin.

In related aspects, methods are provided for monitoring progression of a cancer in a patient, comprising the steps of: (a) contacting a biological sample obtained from a patient with an oligonucleotide that hybridizes to a polynucleotide encoding OB-cadherin; (b) detecting in the sample an amount of polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring progression of a cancer in the patient.

Within other aspects, methods are provided for evaluating the metastatic potential of a cancer in a patient, comprising the steps of: (a) contacting a biological sample obtained from a patient with an oligonucleotide that hybridizes to a polynucleotide encoding OB-cadherin; and (b) detecting in the sample an amount of a polynucleotide that hybridizes to the oligonucleotide, relative to a predetermined cut-off value, and therefrom evaluating the metastatic potential of the cancer in the patient.

In related aspects, diagnostic kits comprising the above oligonucleotide probes or primers are provided.

The following Examples are offered by way of illustration and not by way of limitation.

EXAMPLES

Example 1

Preparation of Representative Modulating Agents

This Example illustrates the solid phase synthesis of representative peptide modulating agents.

The peptides were synthesized on a 431A Applied Biosystems peptide synthesizer using p-Hydroxymethylphenoxymethyl polystyrene (HMP) resin and standard Fmoc chemistry.

After synthesis and deprotection, the peptides were de-salted on a Sephadex G-10 column and lyophilized. The peptides were analyzed for purity by analytical HPLC, and in each case a single peak was observed. Peptides were made as stock solutions at 10 to 25 mg/mL in dimethylsulfoxide (DMSO) or water and stored at −20° C. before use.

Example 2

Disruption of Human Breast Cancer Cell Adhesion

This Example illustrates the ability of a representative linear peptide comprising an OB-cadherin CAR sequence to disrupt human breast epithelial cell adhesion.

MDA-MB-231 human breast cancer cells (Lombardi Cancer Research Center, Washington, D.C.) were used in these experiments. They express OB-cadherin, but not N-cadherin or E-cadherin. The cells were plated (~50,000 cells) on glass coverslips and cultured for 24 hours in DMEM containing 5% serum. Peptides (N-Ac-IFVIDDKSG-NH$_2$ (SEQ ID NO: 17) and H-IFVIDDKSG-OH (SEQ ID NO: 17)) were dissolved in sterile water (10 mg/ml), and 100 μl of each peptide stock solution was added to 1 ml of DMEM containing 5% serum. Control cells had 100 μl of water added to the medium. Cells were monitored by phase contrast microscopy. After 24 hours cells were fixed in formaldehyde. After 24 hours, neither the peptide H-IFVIDDKSG-OH (SEQ ID NO: 17) nor water had an effect on cell morphology (FIG. 3A). The cells treated with either water or H-IFVIDDKSG-OH (SEQ ID NO: 17) remained flattened and well-attached to the substratum. In contrast, the cells treated with N-Ac-IFVIDDKSG-NH$_2$ (SEQ ID NO: 17) rounded up from each other and were not well-attached to the substratum (FIGS. 3A and 3B; arrows indicate rounded cells). These results demonstrate that the peptide N-Ac-IFVIDDKSG-NH$_2$ (SEQ ID NO: 17) interferes with cell adhesion. The amino acid sequence of this peptide is identical to that which is found in the first extracellular domain of OB-cadherin.

Example 3

Detection of OB-Cadherin in Metastatic Ovarian Tumor Cells

This Example illustrates the association between OB-cadherin expression and metastasis in ovarian carcinoma cells.

An RT-PCR approach was employed to assay the presence of OB-cadherin mRNA transcripts in two ovarian cancer cell lines: SKOV3 (a metastatic cell line) and OVCAR3 (a non-invasive cell line). The cDNA was synthesized from 1 μg of total RNA by M-MLV Reverse Transcriptase (Gibco/BRL, Burlington, ON) using random hexamers as primers. PCR was performed using the contents of the first-strand reaction and the OB-cadherin-specific primers and Taq polymerase (Boehringer Mannheim, Laval, Que., Canada). The OB-cadherin-specific primers used were:

```
                                         (SEQ ID NO: 316)
    Forward 5'-ACCAGATGTCTGTATCAGA3';
    and (SEQ ID NO: 317)
    Reverse 5'-GTCTCCTGGTCATCATCTGCA-3'
```

(Munro and Blaschuk, *Biol. Reprod.* 55:822-827, 1996). To confirm the quality of the RNA used, PCR was also performed using primers for the housekeeping gene, hypoxanthine phosphoribosyltransferase (HPRT). The HPRT-specific primers used were:

```
                                         (SEQ ID NO:318)
    Forward 5'-CCTGCTGGATTACATTAAAGCACTG-3';
    and (SEQ ID NO:319)
    Reverse 5'-GTCAAGGGCATATCCAAGAACAAAC-3'
```

(Melton et al., *Proc. Natl. Acad. Sci. USA* 81:2147-2151, 1984). The cycling program was as follows: denaturation at 95° C. for 30 sec.; annealing at 58-60° C. for 45 sec.; polymerization at 72° C. for 1 min.; repeat for 30 cycles. All PCR reactions were performed in parallel with reactions containing no cDNA as a control for contamination of PCR reagents. Products were identified by agarose gel electrophoresis stained with ethidium bromide (Sambrook et al., *Molecular Cloning: A Laboratory Manual*, Cold Spring Harbor Laboratories, Cold Spring Harbor, N.Y., 1989).

Figure 4:
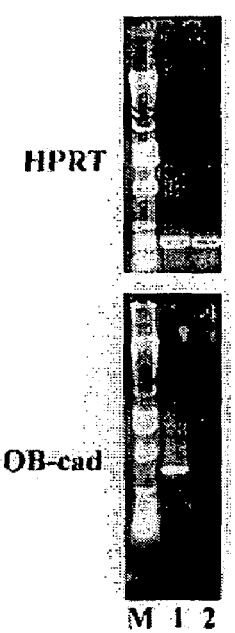
FIG. 4 is a photograph illustrating the results of PCR analysis to detect the presence of OB-cadherin in metastatic human ovarian cancer cells, but not in well-differentiated human ovarian cancer cells. RT-PCR products from two cell lines are shown: SKOV3 in lane 1 and OVCAR3 in lane 2. The primers used were specific for OB-cadherin (OB-cad) and hypoxanthine phosphoribosyltransferase (HPRT) as indicated, with an expected PCR product of 745 bp and 352 bp, respectively. Products were stained with ethidium bromide and resolved by agarose gel electrophoresis. Lane M represents a 1 kb ladder (Gibco/BRL).

The results are presented in FIG. 4, which shows RT-PCR products from SKOV3 (lane 1) and OVCAR3 (lane 2). The primers used are specific for OB-cadherin (OB-cad) and hypoxanthine phosphoribosyltransferase (HPRT) as indicated, with an expected PCR product of 745 bp and 352 bp, respectively. Products were stained with ethidium bromide and resolved by agarose gel electrophoresis, and were all of the expected size. The results indicate that OB-cadherin is expressed by metastatic human ovarian cancer cells, and is not expressed by non-invasive human ovarian cancer cells.

Example 4

Detection of OB-Cadherin in Leukemic Cells

This Example illustrates the expression of OB-cadherin in lymphocytes of leukemia patients.

Figure 5:
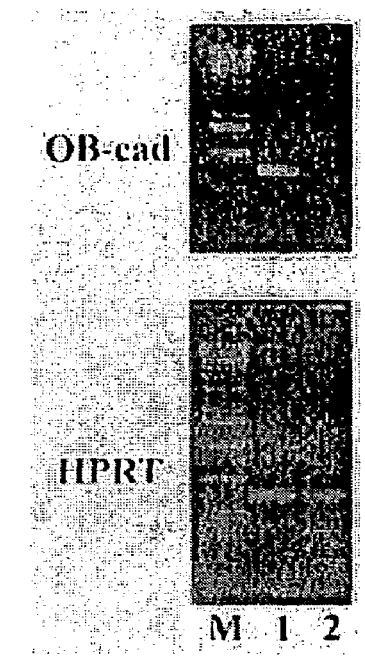
FIG. 5 is a photograph illustrating the results of PCR analysis detecting the presence of OB-cadherin in leukemic cells. RT-PCR products were generated from lymphocytes of a human B-CLL patient (lane 1) and mouse liver (lane 2). The primers used were specific for OB-cadherin (OB-cad, top panel) and hypoxanthine phosphoribosyltransferase (HPRT, bottom panel), with an expected PCR product of 745 bp and 352 bp, respectively. Products were stained with ethidium bromide and resolved by agarose gel electrophoresis. Lane M represents a 1 kb ladder (Gibco/BRL).

The RT-PCR approach described in Example 3 was employed to assay the presence of OB-cadherin mRNA transcripts in lymphocytes prepared from patients with B-cell chronic lymphocytic leukemia (B-CLL). RT-PCR products (shown in FIG. 5) were generated from lymphocytes of a human B-CLL patient (lane 1) and mouse liver (lane 2). The primers used were specific for OB-cadherin (OB-cad, top panel) and hypoxanthine phosphoribosyltransferase (HPRT, bottom panel), with an expected PCR product of 745 bp and 352 bp, respectively. Products were stained with ethidium bromide and resolved by agarose gel electrophoresis, and were all of the expected size. The results indicate that lymphocytes of a leukemia patient express OB-cadherin.

Figure 6:
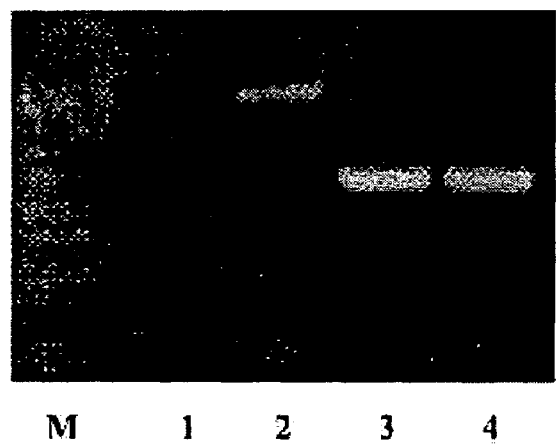
FIG. 6 is a photograph illustrating the results of PCR analysis detecting the presence of OB-cadherin in leukemic cells. RT-PCR products were generated from lymphocytes of a normal human (lanes 1 and 3) and a human B-CLL patient (lanes 2 and 4). The primers used were specific for OB-cadherin (lanes 1 and 2) and hypoxanthine phosphoribosyltransferase (HPRT; lanes 3 and 4), with an expected PCR product of 745 bp and 352 bp, respectively. Products were stained with ethidium bromide and resolved by agarose gel electrophoresis. Lane M represents a 1 kb ladder (Gibco/BRL).

Using the same approach, RT-PCR products (shown in FIG. 6) were generated from peripheral blood lymphocytes from a normal human (lanes 1 and 3) and a human B-CLL patient (lanes 2 and 4). The primers used were specific for OB-cadherin (lanes 1 and 2) and hypoxanthine phosphoribosyltransferase (HPRT; lanes 3 and 4), with an expected PCR product of 745 bp and 352 bp, respectively. Products were stained with ethidium bromide and resolved by agarose gel electrophoresis, and were all of the expected size. The results indicate that lymphocytes of a leukemia patient, but not a normal patient, express OB-cadherin.

Example 5

Detection of OB-Cadherin in Breast Tumor and Metastatic Cells

This Example illustrates the expression of OB-cadherin on primary breast tumor cells and on breast cancer cells that have metastasized to bone.

Paraffin sections (5 microns thick) of primary tumors or bony metastases (Lombardi Cancer Center Histopathology Core) were dewaxed and rehydrated as follows: xylene— three changes for 15 minutes each; absolute ethanol—2 changes for 5 minutes each; 95% ethanol—2 changes for 5 minutes each; 70% ethanol—2 changes for 5 minutes each; three quick rinses in deionized water. The slides were placed in a microwaveable holder and immersed in a pyrex loaf dish containing 1 L 0.01 M citrate buffer. The dish was covered loosely with plastic wrap and placed in a TAPPAN SPEED-wave 1000 microwave and microwaved for 15 minutes on the highest setting. After microwaving, the slides were allowed to cool in the buffer to room temperature.

The slides were then placed into a dish of phosphate buffered saline (PBS) and rinsed two times for 2 minutes each time. Exogenous peroxidases were blocked by placing a solution of 30% peroxide in methanol onto each section for 40 seconds and then rinsing in PBS. Slides were then placed in 150 mm dishes and 10% goat serum (blocking solution) was applied to each section. Moistened kimwipes were placed around the slides and the dish covered and incubated at 37° C. for 15 minutes. While the sections were blocking, affinity purified rabbit anti-OB-cadherin antibody (Zymed, South San Francisco, Calif.) was prepared in PBS to a concentration of 10 μg/ml. Without rinsing, just blotting the excess goat serum from sections, the primary antibody solution was applied to each section (100 micrometers/section), the dish was covered and wrapped in plastic wrap and was placed at 4° C. for 16 hours.

The sections were brought to room temperature and then placed at 37° C. for an additional hour. The slides were then rinsed three times for 2 minutes each time with PBS. Biotinylated goat anti-rabbit secondary antibody (Zymed) was applied to each section and the slides were incubated at 37° C. for 10 minutes. The slides were again rinsed with PBS as above. Streptavidin peroxidase (Zymed) was applied to each section and the slides incubated at 37° C. for 10 minutes. The slides were again rinsed with PBS as stated above.

While in the last PBS rinse, the AEC Chromogen solution was prepared according to the Zymed instructions and 100 μl was applied to each section. The sections were left at room temperature for 10 minutes for the color reaction to develop. The slides were then immersed in deionized water to stop the reaction. Finally the sections were counterstained by placing several drops of Mayers Hematoxylin (Zymed) onto each section for 1 minute. The slides were then rinsed in tap water followed by PBS. The slides were then returned to deionized water and mounted using GVA mount (Zymed).

Figure 7:
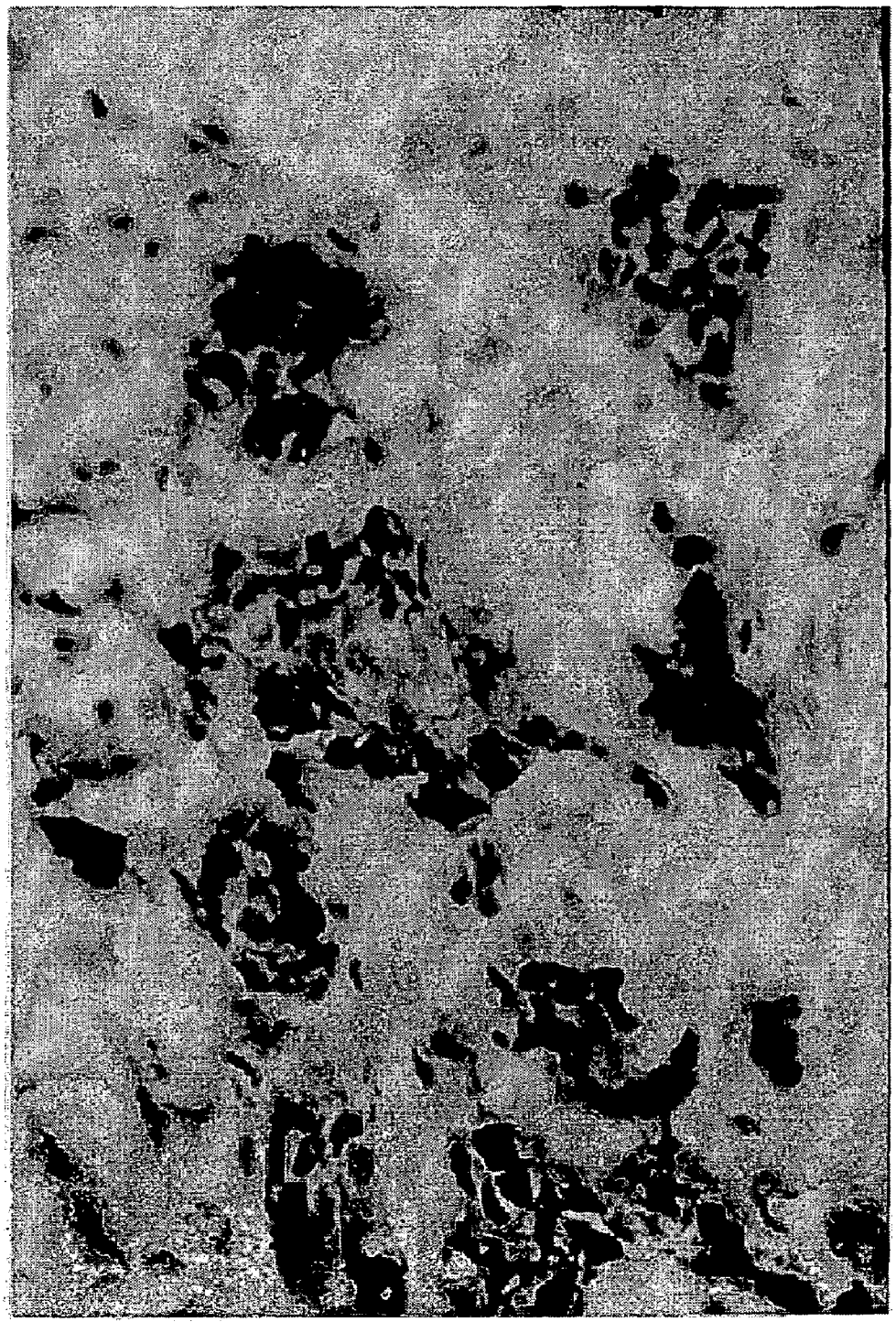
FIG. 7 is a photograph showing the results of immunostaining with affinity purified rabbit anti-OB-cadherin antibody to detect the presence of OB-cadherin on primary breast tumor cells.
Figure 8:
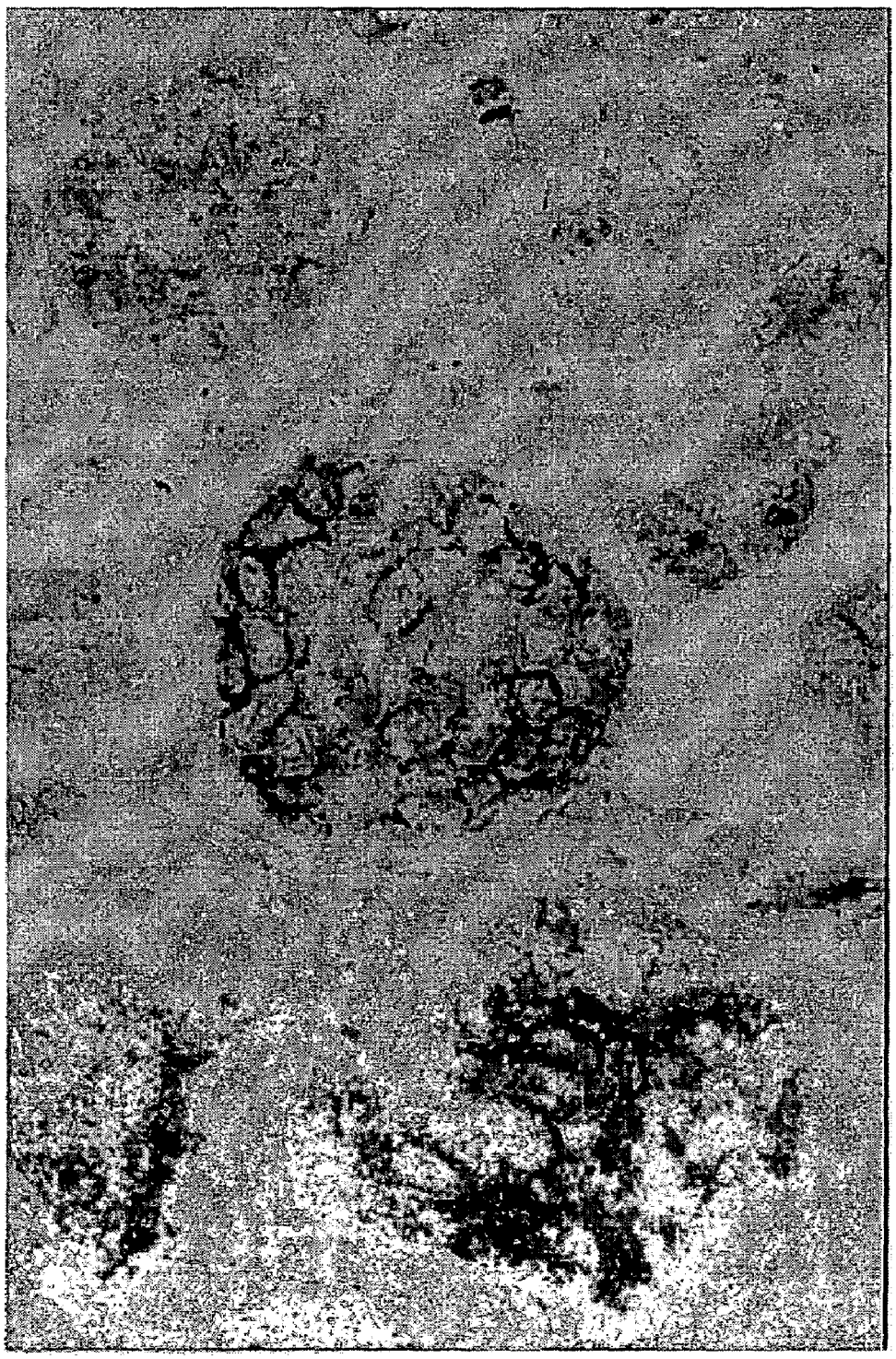
FIG. 8 is a photograph showing the results of immunostaining with affinity purified rabbit anti-OB-cadherin antibody to detect the presence of OB-cadherin on a breast cancer metastatic deposit in the femur.

Results for primary tumor and metastatic deposits are shown in FIGS. 7 and 8. FIG. 7 shows a primary breast tumor. Positive staining was observed on all of the cells at the edge of the tumor nest. OB-cadherin is expressed on all cell surfaces (i.e., expression is not restricted to cell-cell contact sites).

FIG. 8 shows a metastatic deposit in the femur. This deposit arose from the primary tumor shown in FIG. 7. OB-cadherin staining is associated with cell-cell borders in most tumor nests.

These results indicate that breast tumor and metastatic cells express OB-cadherin, and that metastatic cells express OB-cadherin on all cell surfaces. In addition, these results confirm the detection of breast cancer and metastatic cancer based on assays for OB-cadherin expression.

Example 6

Inhibition of Cancer Cell Invasion by OB-Cadherin Modulating Agents

A Boyden chamber invasion assay was performed to evaluate the ability of OB-cadherin modulating agents to inhibit cancer cell invasion. On day 1, Matrigel solution was diluted in $H_2O$ in a 10 cm diameter tissue culture plate to a final concentration of 20 μg/ml. An 8 μm porous membrane was submerged topside down in the matrigel solution and was left at 4° C. overnight. A 175 $cm^2$ flask of low passage number MDA-MB-231 cells was serum-starved overnight. On day 2, following coating with matrigel the membrane was air-dried using appropriate clamps for at least 3 hours. The Boyden chamber was rinsed 3 times with $ddH_2O$ and subsequently dried in the tissue culture hood.

Before assembly of Boyden apparatus, the appropriate peptide or control solutions were prepared. Twice the required concentration was diluted into 250 ul of serum-free DMEM tissue culture medium. Subsequently, the serum-starved MDA-MB-231 cells were washed once with 1×PBS and trypsinized. The cell number per ml was determined using a Coulter counter. As each Boyden chamber well required 10000 cells, 100000 cells were needed for a final volume of 500 μl for each treatment. Therefore, trypsinized cells were re-suspended at a concentration of 100000 cells per 250 μl serum-free DMEM tissue culture medium and subsequently added to the previously prepared 250 ul of peptide solutions.

Figure 9:
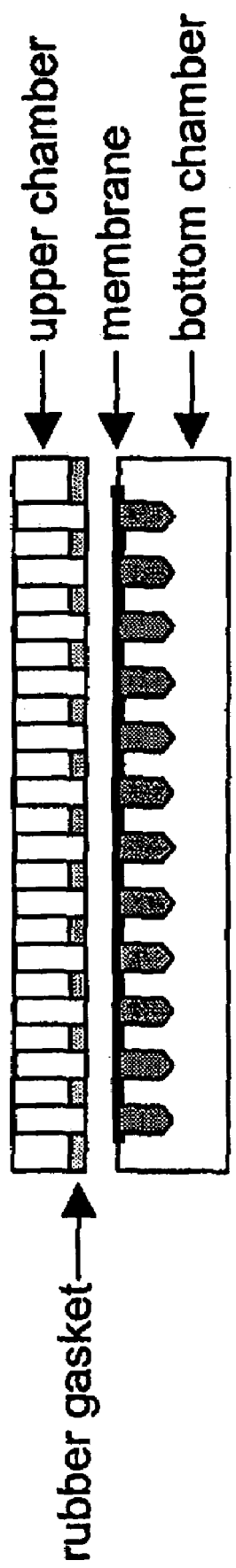
FIG. 9 is an illustration of an apparatus used to evaluate cancer cell invasion properties in response to OB-cadherin modulating agents in a Boyden chamber invasion assay.

Next, the bottom chamber of the Boyden apparatus was loaded with the chemoattractant (15% FBS containing DMEM medium). A meniscus was created that ensured saturation of the membrane with chemoattractant but prevented the chemoattractant from overflowing into neighboring wells. Following the addition of chemoattractant, the air-dried membrane was placed topside up onto the bottom chamber. Then the upper chamber of the Boyden apparatus, with the rubber gasket flush and securely attached to the bottom of the upper chamber, was secured onto the bottom chamber using screws (FIG. 9).

Upon completed assembly of the Boyden apparatus, 50 μl of the pre-prepared peptide-cell or control-cell solutions were loaded into the wells of the top chamber. Each peptide or control treatment was loaded in triplicate and a positive control (no treatment) and negative control (no chemoattractant) were included. Care was taken to avoid air-bubbles that would inhibit invasion of cells. Cells were left to invade for 16 hours at 37° C.

Following the incubation time, 10 ml of DiffQuik fixative were aliquoted into a 10 cm diameter tissue culture plate. The Boyden apparatus was carefully disassembled so that the membrane would remain attached to the inverted top chamber. Using two forceps the membrane was moved from the inverted top chamber into the fixative solution. The membrane was incubated in fixative for 5 minutes at room temperature. After incubation the initially bottom-side up membrane was inverted. The fixative was subsequently poured out and the membrane was incubated in 10 ml of cytoplasm staining solution (DiffQuik) for 3 minutes at room temperature. After removal of dye the membrane was submerged in nuclei staining solution (DiffQuik) for 5 minutes at room temperature. Finally, the membrane was washed twice in ddH$_2$O. The membrane was kept submerged in ddH$_2$O while cells was carefully swiped of the topside of the membrane using cotton tip. The membrane was dried using the appropriate clamps as before. The apparatus was rinsed with distilled water.

The air-dried membrane was dessicated in xylenes for at least 90 minutes before being mounted on a glass slide using Cytoseal 60. The membrane was covered with cover slips and left to dry. For analysis, pictures of each cell invasion spot were taken using an Olympus Vanox microscope at ×2.5 magnification. A focusing reticle served to determine the centre of each cell invasion spot. The pictures of the cells were further analysed using the Metamorph analysis program to determine the number of stained nuclei, hence number of cells, within each picture. Tools within the Metamorph program were employed to ensure discrimination between pores and nuclei.

A summary of the observed results is provided in the table below. Level of activity of the OB-cadherin modulating agents is expressed as peptide concentration resulting in approximately 50% inhibition of cell invasion.

| Name | Sequence | 50% inhibition |
|---|---|---|
| ADH92 | Ac-IFVIDDKSG-NH$_2$ (SEQ ID NO: 17) | >1 mg/ml |
| ADH93 | H-IFVIDDKSG-OH (SEQ ID NO: 17) | ~0.6 mg/ml |
| ADH113 | Ac-CDDKC-NH$_2$ (SEQ ID NO: 57) | >1 mg/ml |
| ADH114 | H-CDDKC-OH (SEQ ID NO: 57) | ~0.6 mg/ml |

Figures 10A, 10B:
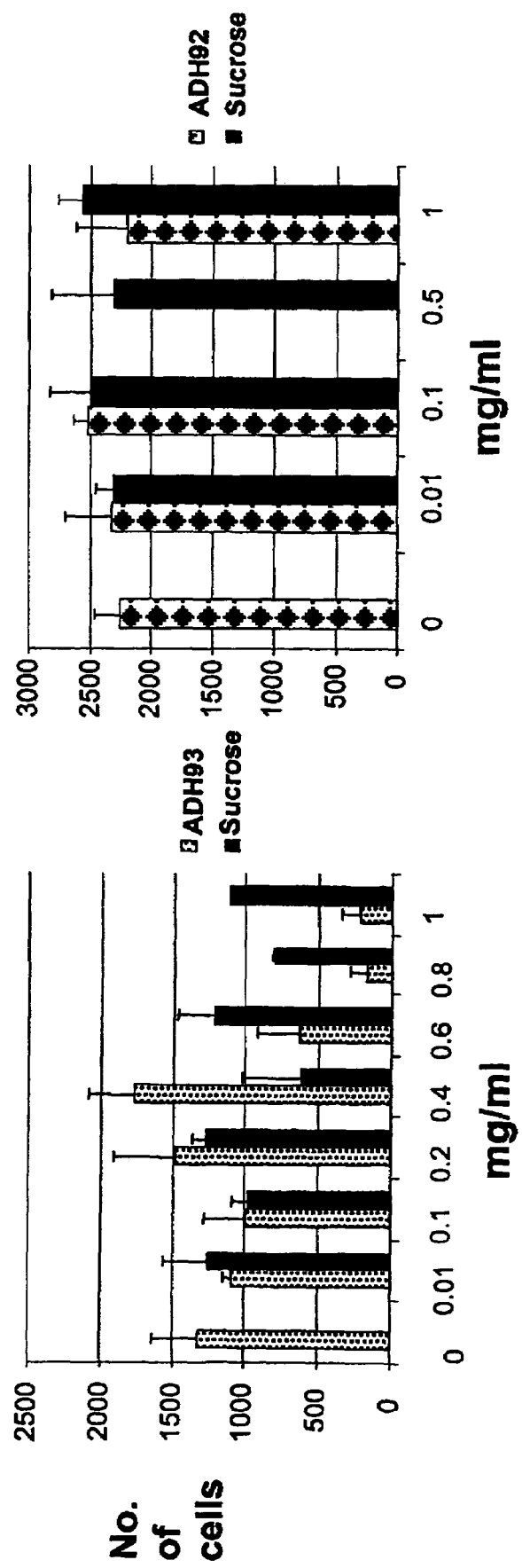
FIGS. 10A-10B show the effects of OB-cadherin modulating agents ADH92 and ADH93 on breast cancer cell invasion through a matrigel-coated membrane.
Figures 11A, 11B:
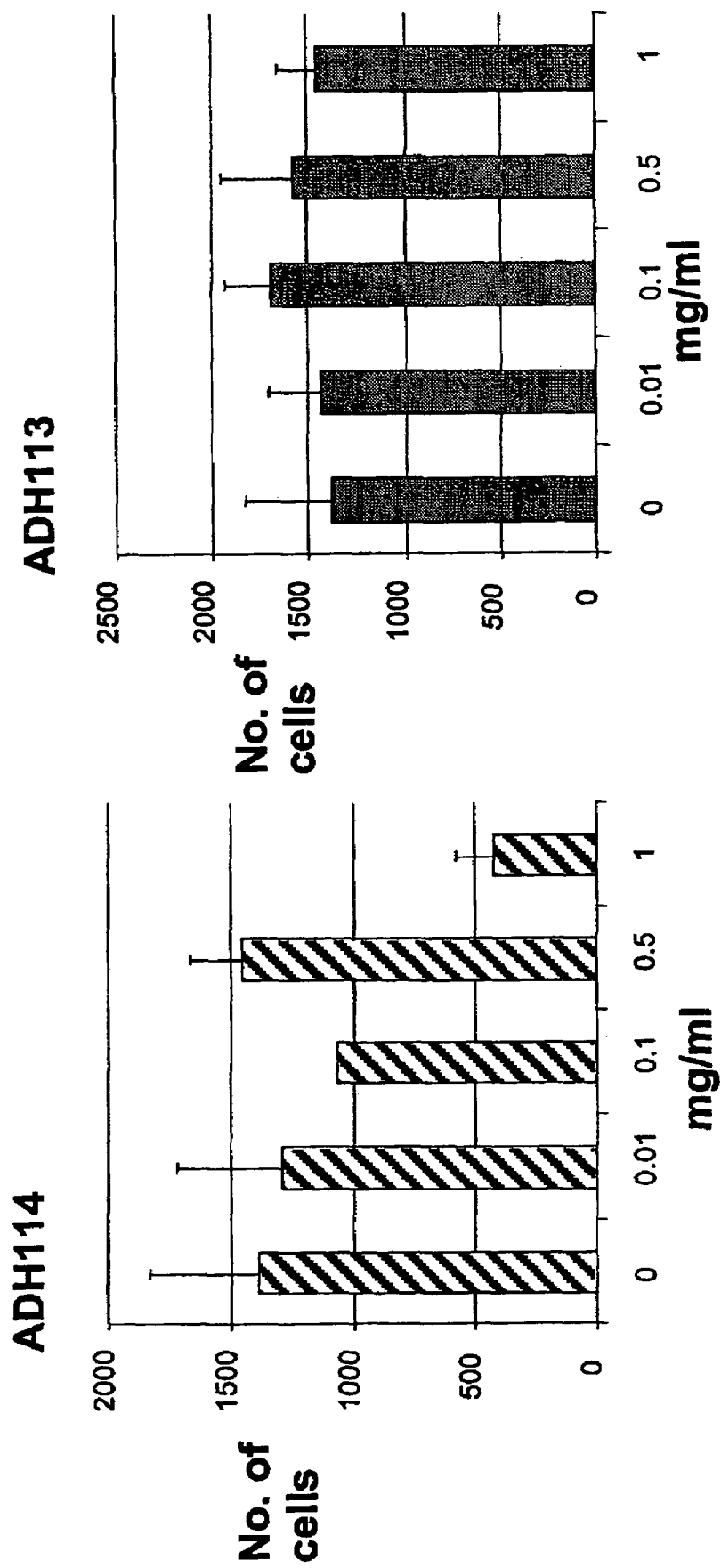
FIGS. 11A-11C show the effects of OB-cadherin modulating agents ADH113 and ADH114 on breast cancer cell invasion through a matrigel-coated membrane.
Figure 11C:
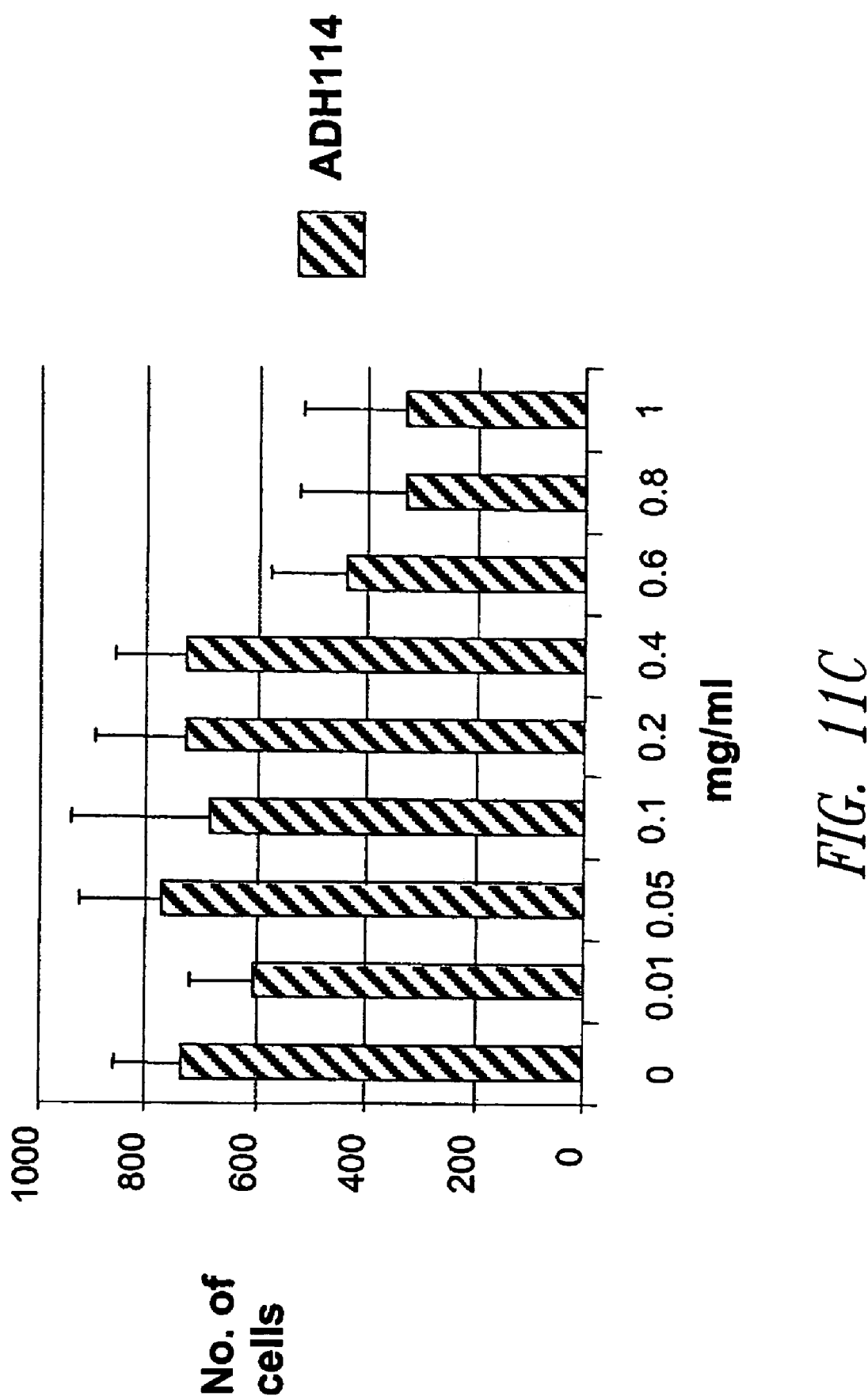

In addition, as shown in FIG. 10, ADH93 inhibited MDA-MB-231 cell invasion through a matrigel-coated membrane at peptide concentrations of >0.6 mg/ml. In contrast, ADH92 did not have an observed effect on cell invasion. The effect of ADH114 and ADH113 are shown in FIG. 11. A marked decrease in the number of cells invading the matrigel-coated membrane was observed using ADH114. An approximately 50% reduction in cell invasion occurred at 0.6 mg/ml peptide concentration and was maintained at higher concentrations. ADH113 did not result in a significant decrease in cell invasion.

The range of peptide concentrations tested revealed ADH93 and ADH114 to inhibit 50% of cell invasion at ~0.6 mg/ml peptide concentration.

In conclusion, the OB-cadherin modulating agents ADH93 and ADH114 were shown to cause a decrease in cell invasion of MDA-MB-231 cells at >0.6 mg/ml concentrations.

Example 7

Modulation of VEGF Expression by OB-Cadherin Modulating Agents

MDA-MB-231 cells were plated at equal numbers. After serum-starving for 24 hours, cells were incubated for 16 hours in the presence of different concentrations of OB-cadherin-modulating agents. The medium supernatants containing the secreted VEGF-A protein were analyzed using the VEGF-A ELISA kit (R&D Systems). An ELISA immunoassay (VEGF-A ELISA kit, R&D Systems) was performed to investigate the relationship between increasing cell density and VEGF-A secretion. The protocol was carried out according to instructions provided with the VEGF-A ELISA kit. MDA-MB-231 cells were plated at increasing cell numbers and left to grow in complete growth medium (DMEM, 5% FBS, 2 mM glutamine) for 24 hours. Prior to performing the experiment the VEGF-A Standard was dissolved using Calibrator Diluent RD5K to produce a stock solution of 2000 pg/ml. The stock solution was used to produce a dilution series where 1000 pg/ml served as the high standard and calibrator diluent RD5K alone served as the zero standard (0 pg/ml).

After removing excess microplate strips from the plate frame, 50 µl of assay diluent RD1W were added to each experimental well. Further, 200 µl of standard, control or sample were added per well in duplicate. Sample solutions consisted of medium supernatants taken from the growing cell cultures. Supernatants were briefly spun down to pellet any solids and the supernatant added to experimental wells. The microplate was covered with the adhesive strip provided and incubated for 2 hours at room temperature. Following incubation the wells were aspirated and washed with 400 µl wash buffer, repeating the process twice to achieve a total of three washes. After the last wash, any remaining wash buffer was removed by aspirating or decanting, before the inverted plate was blotted against clean paper towels.

To each well 200 µl VEGF-A conjugate was added and the microplate covered with a new adhesive strip provided. The microplate was incubated at room temperature for 2 hours. Following incubation, wash steps as previously described were repeated. Addition of 200 µl of Substrate solution to each well was followed by incubation in the dark at room temperature for 20 minutes. Subsequently, 50 µl of Stop solution was added to each well and thoroughly mixed to achieve a uniform color change.

Experimental analysis was carried out through determination of the optical density of each well within 30 minutes, using a microplate reader set to 450 nm. Wavelength correction was set at 540 nm. Duplicate readings for each standard, control and sample were averaged and the average zero standard optical density was subtracted. Using computer software a standard curve was generated. The data was linearized by plotting the log of the VEGF-A concentrations versus the log of the O.D. producing an adequate fit of data.

Incubation in the presence of ADH93 (H-IFVIDDKSG-OH) (SEQ ID NO: 17) at concentrations of 0.2-mg/ml or higher dramatically reduced the secretion of VEGF-A. In contrast, incubation in the presence of ADH92 (Ac-IFVID-DKSG-NH2) (SEQ ID NO: 17) did not substantially alter VEGF-A secretion.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated monoclonal antibody or antigen-binding fragment thereof that specifically binds to the OB-cadherin CAR sequence DDK, wherein the agent is capable of modulating OB-cadherin-mediated cell adhesion.

2. An antibody or antigen-binding fragment thereof according to claim 1, wherein the antibody or antigen-binding-fragment thereof specifically binds to the OB-cadherin CAR sequence selected from the group consisting of DDK, IDDK (SEQ ID NO: 4) DDKS (SEQ ID NO: 5), VIDDK (SEQ ID NO: 6), IDDKS (SEQ ID NO: 7), VIDDKS (SEQ ID NO: 8), DDKSG (SEQ ID NO: 9), IDDKSG (SEQ ID NO: 10), VIDDKSG (SEQ ID NO: 11), FVIDDK (SEQ ID NO: 12), FVIDDKS (SEQ ID NO: 13), FVIDDKSG (SEQ ID NO: 14), IFVIDDK (SEQ ID NO: 15), IFVIDDKS (SEQ ID NO: 16), and IFVIDDKSG (SEQ ID NO: 17).

3. A composition comprising an antibody according to any one of claims 1 or 2 and a physiologically acceptable carrier.

* * * * *